US012723077B2

(12) United States Patent
Liang et al.

(10) Patent No.: US 12,723,077 B2
(45) Date of Patent: Sep. 1, 2026

(54) PILRA ANTIBODIES AND METHODS OF USE THEREOF

(71) Applicant: Alector LLC, South San Francisco, CA (US)

(72) Inventors: Spencer Liang, South San Francisco, CA (US); Samuel Nalle, Pacifica, CA (US); Ling Leung, Foster City, CA (US)

(73) Assignee: Alector LLC, South San Francisco, CA (US)

( * ) Notice: Subject to any disclaimer, the term of this patent is extended or adjusted under 35 U.S.C. 154(b) by 1050 days.

(21) Appl. No.: 17/904,513

(22) PCT Filed: Feb. 17, 2021

(86) PCT No.: PCT/US2021/018354

§ 371 (c)(1),
(2) Date: Aug. 18, 2022

(87) PCT Pub. No.: WO2021/167964

PCT Pub. Date: Aug. 26, 2021

(65) Prior Publication Data

US 2023/0220074 A1 Jul. 13, 2023

Related U.S. Application Data

(60) Provisional application No. 63/075,440, filed on Sep. 8, 2020, provisional application No. 62/978,106, filed on Feb. 18, 2020.

(51) Int. Cl.
*C07K 16/28* (2006.01)
*A61K 39/00* (2006.01)
*A61P 35/00* (2006.01)

(52) U.S. Cl.
CPC .......... *C07K 16/2803* (2013.01); *A61P 35/00* (2018.01); *C07K 16/2827* (2013.01); *A61K 2039/507* (2013.01); *C07K 2317/76* (2013.01)

(58) Field of Classification Search
CPC ................ A61P 35/00; C07K 2317/76; A61K 2039/505
See application file for complete search history.

(56) References Cited

U.S. PATENT DOCUMENTS

| | | | |
|---|---|---|---|
| 5,122,464 | A | 6/1992 | Wilson et al. |
| 5,223,409 | A | 6/1993 | Ladner et al. |
| 5,225,539 | A | 7/1993 | Winter |
| 5,403,484 | A | 4/1995 | Ladner et al. |
| 5,427,908 | A | 6/1995 | Dower et al. |
| 5,516,637 | A | 5/1996 | Huang et al. |
| 5,571,698 | A | 11/1996 | Ladner et al. |
| 5,580,717 | A | 12/1996 | Dower et al. |
| 5,658,727 | A | 8/1997 | Barbas et al. |
| 5,693,780 | A | 12/1997 | Newman et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,807,715 | A | 9/1998 | Morrison et al. |
| 5,821,047 | A | 10/1998 | Garrard et al. |
| 5,965,726 | A | 10/1999 | Pavlakis et al. |
| 5,969,108 | A | 10/1999 | McCafferty et al. |
| 6,174,666 | B1 | 1/2001 | Pavlakis et al. |
| 6,291,664 | B1 | 9/2001 | Pavlakis et al. |
| 6,414,132 | B1 | 7/2002 | Pavlakis et al. |
| 6,794,498 | B2 | 9/2004 | Pavlakis et al. |
| 7,709,226 | B2 | 5/2010 | Foote |
| 9,556,269 | B2 * | 1/2017 | Zarrin ................ C07K 16/2803 |
| 2004/0014194 | A1 | 1/2004 | Beyer et al. |
| 2010/0129347 | A1 | 5/2010 | Arase et al. |
| 2019/0211098 | A1 | 7/2019 | Bhangale et al. |

FOREIGN PATENT DOCUMENTS

| | | | |
|---|---|---|---|
| EP | 2127672 | A1 | 12/2009 |
| WO | WO-8605807 | A1 | 10/1986 |
| WO | WO-8901036 | A1 | 2/1989 |
| WO | WO-9002809 | A1 | 3/1990 |
| WO | WO-9110737 | A1 | 7/1991 |
| WO | WO-9201047 | A1 | 1/1992 |
| WO | WO-9218619 | A1 | 10/1992 |
| WO | WO-9311236 | A1 | 6/1993 |
| WO | WO-9515982 | A2 | 6/1995 |

(Continued)

OTHER PUBLICATIONS

R&D Systems Catalog No. MAB64842. Human PILR-a Antibody; Recombinant monoclonal rabbit IgG clone # 2175B. Revision Feb. 7, 2018. (Year: 2018).*

Edwards, Bryan M., et al. "The remarkable flexibility of the human antibody repertoire; isolation of over one thousand different antibodies to a single protein, BLyS." Journal of molecular biology 334.1 (2003): 103-118. (Year: 2003).*

Sela-Culang, Inbal, Vered Kunik, and Yanay Ofran. "The structural basis of antibody-antigen recognition." Frontiers in immunology 4 (2013): 302. (Year: 2013).*

(Continued)

*Primary Examiner* — Julie Wu
*Assistant Examiner* — Bryan William Heck
(74) *Attorney, Agent, or Firm* — McNeill PLLC

(57) ABSTRACT

The present disclosure provides antibodies and antigen-binding fragments thereof that specifically bind to human PILRA and compositions comprising such antibodies or antigen-binding fragments thereof. In a particular aspect, the antibodies or antigen-binding fragments thereof that specifically bind to human PILRA block binding of PILRA to ligand and/or decrease cell surface PILRA. In further aspects, the antibodies or antigen-binding fragments can be used to treat diseases or conditions associated with myeloid cell dysfunction.

34 Claims, 17 Drawing Sheets

Specification includes a Sequence Listing.

(56) References Cited

FOREIGN PATENT DOCUMENTS

| | | | |
|---|---|---|---|
| WO | WO-9520401 | A1 | 8/1995 |
| WO | WO-9713844 | A1 | 4/1997 |
| WO | WO-2007005874 | A2 | 1/2007 |
| WO | WO-2008084710 | A1 | 7/2008 |
| WO | WO-2009036379 | A2 | 3/2009 |
| WO | WO-2009085920 | A1 | 7/2009 |
| WO | WO-2009102473 | A2 | 8/2009 |
| WO | WO-2010105256 | A1 | 9/2010 |
| WO | WO-2011084357 | A1 | 7/2011 |
| WO | WO-2012009568 | A2 | 1/2012 |
| WO | WO-2012088383 | A2 | 6/2012 |
| WO | WO-2012145493 | A1 | 10/2012 |
| WO | WO-2013079174 | A1 | 6/2013 |
| WO | WO-2019126472 | A1 | 6/2019 |
| WO | WO-2021167964 | A1 | 8/2021 |
| WO | WO-2023028525 | A2 | 3/2023 |

OTHER PUBLICATIONS

Abdiche, Y.N., et al., "Exploring Blocking Assays using Octet, Proteon, and Biacore Biosensors," Analytical Biochemistry 386(2):172-180, Elsevier, United States (2009).
Al-Lazikani, B., et al., "Standard Conformations for the Canonical Structures of Immunoglobulins," Journal of Molecular Biology 273(4):927-948, Elsevier, Netherlands (Nov. 1997).
Ames, R.S., et al., "Conversion of Murine Fabs Isolated From a Combinatorial Phage Display Library to Full Length Immunoglobulins," Journal of Immunological Methods 184(2):177-186, Elsevier, Netherlands (1995).
Bricogne, G., "[23] Bayesian Statistical Viewpoint on Structure Determination: Basic Concepts and Examples," Methods in Enzymology 276:361-423, Academic Press, United States (1997).
Bricogne, G., "Direct Phase Determination by Entropy Maximization and Likelihood Ranking: Status Report and Perspectives," Acta Crystallographica. Section D, Biological Crystallography 49(Pt1):37-60, Wiley-Blackwell, United States (Jan. 1993).
Brinkmann, U., et al., "Phage Display of Disulfide-stabilized Fv Fragments," Journal of Immunological Methods 182(1):41-50, Elsevier, Netherlands (1995).
Burton, D.R. and Barbas, C.F. 3rd., "Human Antibodies From Combinatorial Libraries," Advances in Immunology 57:191-280, Academic Press, United States (1994).
Champe, M., et al., "Monoclonal Antibodies that Block the Activity of Leukocyte Function-Associated Antigen 1 Recognize Three Discrete Epitopes in the Inserted Domain of CD11a," The Journal of Biological Chemistry 270(3):1388-1394, Elsevier Inc. on behalf of American Society for Biochemistry and Molecular Biology, United States (Jan. 1995).
Chayen, N.E., "The Role of Oil in Macromolecular Crystallization," Structure 5(10):1269-1274, Cell Press, United States (Oct. 1997).
Cheung, R.C., et al., "Epitope-specific Antibody Response to the Surface Antigen of Duck Hepatitis B Virus in Infected Ducks," Virology 176(2):546-552, Academic Press, United States (1990).
Chothia, C. and Lesk, A. M., "Canonical Structures for the Hypervariable Regions of Immunoglobulins," Journal of Molecular Biology 196(4):901-917, Elsevier, United Kingdom (Aug. 1987).
Chothia, C., et al., "Structural Repertoire of the Human VH Segments," Journal of Molecular Biology 227(3):799-817, Academic Press, United Kingdom (1992).
Clackson, T., et al., "Making Antibody Fragments using Phage Display Libraries," Nature 352(6336):624-628, Nature Publishing Group, United Kingdom (Aug. 1991).
Cockett, M.I., et al., "High Level Expression of Tissue Inhibitor of Metalloproteinases in Chinese Hamster Ovary Cells Using Glutamine Synthetase Gene Amplification," Biotechnology 8(7):662-667, Nature Publishing Company, United States (Jul. 1990).
Cruts, M., and Broeckhoven, C.V., "Loss of Progranulin Function In Frontotemporal Lobar Degeneration," Trends in Genetics 24(4):186-194, Elsevier Trends Journals, United Kingdom (Mar. 2008).
Cunningham, B.C. and Wells, J.A., "High-resolution Epitope Mapping of hGH-receptor Interactions by Alanine-scanning Mutagenesis," Science 244(4908):1081-1085, American Association for the Advancement of Science, United States (Jun. 1989).
Davidson, E., and Doranz, B. J., "A high-throughput shotgun mutagenesis approach to mapping B-cell antibody epitopes," Immunology 143(1):13-20, American Association of Immunologists, United States (2014).
Foecking, M.K. and Hofstetter, H., "Powerful and Versatile Enhancer-promoter Unit for Mammalian Expression Vectors," Gene 45(1):101-105, Elsevier/North-Holland, Netherlands (1986).
Fournier, N., et al., "FDF03, A Novel Inhibitory Receptor of the Immunoglobulin Superfamily, is Expressed by Human Dendritic and Myeloid Cells," Journal of Immunology 165(3):1197-1209, American Association of Immunologists, United States (Aug. 2000).
Giege, R., et al., "Crystallogenesis of biological macromolecules: facts and perspectives," Acta Crystallographica. Section D, Biological Crystallography 50(Pt4):339-350, Wiley-Blackwell, United States (Jul. 1994).
Hammerling, G.J., et al., "Appendix: Production of Antibody-Producing Hybridomas in the Rodent Systems," in: Monoclonal Antibodies and T-Cell Hybridomas: Perspectives and Technical Advances, pp. 563-587, Elsevier, Netherlands (1981).
Harlow, E., and Lane, D., Chapter 10: Cell Staining, Antibodies: A Laboratory Manual, pp. 386-389, Cold Spring Harbor Laboratory Press, United States (1988).
Hutton, M., et al., "Association of Missense and 5'-splice-site Mutations in Tau With the Inherited Dementia Ftdp-17," Nature 393(6686):702-705 Nature Publishing Group, United Kingdom (Jun. 1998).
International Search Report and Written Opinion for International Application No. PCT/US2021/018354, European Patent Office, Netherlands, mailed on Jun. 7, 2021, 14 pages.
Jones, P.T., et al., "Replacing the Complementarity-determining Regions in a Human Antibody with those from a Mouse," Nature 321(6069):522-525, Nature Publishing Group, United Kingdom (May 1986).
Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (1971).
Kabat, E.A., et al., "Sequences of proteins of immunological interest," 5th Edition, NIH publication No. 91-3242, pp. 1-1137, U.S. Department of Public Health and Human Services, National Institutes of Health, United States (1991).
Kettleborough, C.A., et al., "Isolation of Tumor Cell-specific Single-chain Fv From Immunized Mice Using Phage-antibody Libraries and the Re-construction of Whole Antibodies From These Antibody Fragments, " European Journal of Immunology 24(4):952-958, Wiley-VCH, Germany (1994).
Kim, S.J., et al., "Guided Selection of Human Antibody Light Chains Against TAG-72 Using a Phage Display Chain Shuffling Approach," Journal of Microbiology 45(6):572-577, Microbiological Society of Korea, Korea (2007).
Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (1986).
Kohler, G. and Milstein, C., "Continuous Cultures of Fused Cells Secreting Antibody of Predefined Specificity," Nature 256(5517):495-497, Nature Publishing Group, England (Aug. 1975).
Kuroki, K., et al., "Structural Basis for Simultaneous Recognition of an O-glycan and Its Attached Peptide of Mucin Family by Immune Receptor PILRα," Proceedings of the National Academy of Sciences of the United States of America 111(24):8877-8882, National Academy of Sciences, United States (Jun. 2014).
Kuroki, M., et al., "Biochemical Characterization of 25 Distinct Carcinoembryonic Antigen (CEA) Epitopes Recognized by 57 Monoclonal Antibodies and Categorized Into Seven Groups in Terms of Domain Structure of the CEA Molecule," Hybridoma 11(4):391-407, Mary Ann Liebert, United States (1992).
Kuroki, M., et al., "Determination of Epitope Specificities of a Large Number of Monoclonal Antibodies by Solid-phase Mutual

(56) References Cited

OTHER PUBLICATIONS

Inhibition Assays Using Biotinylated Antigen," Immunological Investigations 21(6):523-538, Informa Healthcare, United Kingdom (1992).
Kuroki, M., et al., "Serological Mapping of the TAG-72 Tumor-Associated Antigen Using 19 Distinct Monoclonal Antibodies," Cancer Research 50(16):4872-4879, American Association for Cancer Research, United States (1990).
Lefranc, M.P., et al., "IMGT, the International ImMunoGeneTics Database," Nucleic Acids Research 27(1):209-212, Oxford University Press, United Kingdom (1999).
Lefranc, M.P., et al., "The IMGT Unique Numbering for Immunoglobulins, T Cell Receptors and Ig-like Domains," The Immunologist 7(4): 132-136, Hogrefe & Huber Publishers, United States (1999).
Maccallum, R.M., et al., "Antibody-antigen Interactions: Contact Analysis and Binding Site Topography," Journal of Molecular Biology 262(5):732-745, Academic Press, United Kingdom (Oct. 1996).
Martin, A. C. R., "Chapter 31: Protein Sequence and Structure Analysis of Antibody Variable Domains" in Antibody Engineering, Kontermann and Dubel, eds., pp. 422-439, Springer-Verlag, Germany (2001).
McPherson, A., "Crystallization of Proteins From Polyethylene Glycol," The Journal of Biological Chemistry 251(20):6300-6303, Elsevier Inc. on behalf of American Society for Biochemistry and Molecular Biology, United States (Oct. 1976).
McPherson, A., "Current Approaches to Macromolecular Crystallization," European Journal of Biochemistry 189(1):1-23, Blackwell Science Ltd, United Kingdom (Apr. 1990).
Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, United Kingdom (1990).
Morel, G.A., et al., "Monoclonal Antibodies to Bovine Serum Albumin: Affinity and Specificity Determinations," Molecular Immunology 25(1):7-15, Pergamon Press, United Kingdom (1988).
Neary, D., et al., "Frontotemporal Lobar Degeneration: A Consensus On Clinical Diagnostic Criteria, " Neurology 51(6):1546-1554, Lippincott Williams & Wilkins, United States (Dec. 1998).
Neumann, M., et al., "TDP-43 Proteinopathy in Frontotemporal Lobar Degeneration and Amyotrophic Lateral Sclerosis Protein Misfolding Diseases Without Amyloidosis," Archives of Neurology 64(10):1388-1394, American Medical Association, United States (Oct. 2007).
Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).
Rader, C., et al., "A Phage Display Approach for Rapid Antibody Humanization: Designed Combinatorial V Gene Libraries," Proceedings of the National Academy of Sciences USA 95(15):8910-8915, National Academy of Sciences, United States (Jul. 1998).
Rathore, N., et al., "Paired Immunoglobulin-like Type 2 Receptor Alpha G78R Variant Alters Ligand Binding and Confers Protection to Alzheimer's Disease," PLOS Genetics 14(11):e1007427, Public Library of Science, United States (Nov. 2018).
Ratnavalli, E., et al., "The Prevalence of Frontotemporal Dementia," Neurology 58(11):1615-1621, Lippincott Williams & Wilkins, United States (Jun. 2002).
Riechmann, L., et al., "Reshaping Human Antibodies for Therapy," Nature 332(6162):323-327, Nature Publishing Group, United Kingdom (Mar. 1988).
Roguska, M.A., et al., "A Comparison of Two Murine Monoclonal Antibodies Humanized by CDR-grafting and Variable Domain Resurfacing," Protein Engineering 9(10):895-904, Oxford University Press, United Kingdom (Oct. 1996).
Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).
Roversi, P., et al., "Modelling Prior Distributions of Atoms for Macromolecular Refinement and Completion," Acta Crystallographica. Section D, Biological Crystallography 56(Pt10):1316-1323, Wiley-Blackwell, United States (Oct. 2000).
Satoh, T., et al., "PILRα Is a Herpes Simplex Virus-1 Entry Co-receptor That Associates with Glycoprotein B; Supplemental Experimental Procedures, Construction of plasmids," Cell 132:S1-S8, (Mar. 2008), Retrieved from URL: (https://www.cell.com/cms/10.1016/j.cell.2008.01.043/attachment/8ae918c2-2f9d-4d53-a0c6-35172ca834c6/mmc1.pdf).
Satoh, T., et al., "PILRα is a Herpes Simplex Virus-1 Entry Co-receptor That Associates With Glycoprotein B," Cell 132(6):935-944, Cell Press, United States (Mar. 2008).
Stahli, C., et al., "Distinction of Epitopes by Monoclonal Antibodies," Methods in Enzymology 92:242-253, Academic Press, United States (1983).
Tramontano, A., et al., "Framework Residue 71 is a Major Determinant of the Position and Conformation of the Second Hypervariable Region in the VH Domains of Immunoglobulins," Journal of Molecular Biology 215(1):175-182, Academic Press, United Kingdom (1990).
Verhoeyen, M., et al., "Reshaping Human Antibodies: Grafting an Antilysozyme Activity," Science 239(4847):1534-1536, American Association for the Advancement of Science, United States (Mar. 1988).
Wagener, C., et al., "Monoclonal Antibodies for Carcinoembryonic Antigen and Related Antigens as a Model System: a Systematic Approach for the Determination of Epitope Specificities of Monoclonal Antibodies.," Journal of Immunology 130(5):2308-2315, American Association of Immunologists, United States (1983).
Wagener, C., et al., "Use of Biotin-Labeled Monoclonal Antibodies and Avidin-Peroxidase Conjugates for the Determination of Epitope Specificities in a Solid-phase Competitive Enzyme Immunoassay," Journal of Immunological Methods 68 (1-2):269-274, Elsevier, Netherlands (1984).
Uniprot, "PILRA—Paired immunoglobin like type 2 receptor alpha—*Macaca fascicularis* (Crab-eating macaque)," retrieved from https://www.uniprot.org/uniprotkb/A0A2K5X997/entry, accessed on Nov. 1, 2022, 6 pages.
International Search Report and Written Opinion for International Application No. PCT/US22/75411, Commissioner for Patents, United States, mailed on Jan. 27, 2023, 15 pages.

* cited by examiner

Tumor volume

Tumor Volume mm$^3$ ± SEM 2500 2000 1500 1000 500 0

5 10 15 25

Dose 1 Dose 2 Dose 3 Dose 4

DPI (Days Post Innoculation)

mIgG1 (13 mpk)

mIgG1 (10 mpk) + anti-PD-L1 (3 mpk)

mPILRA - mIgG1 (10 mpk) + anti-PD-L1 (3 mpk)

Survival

Probability of Survival 100 50 0

20 30 40 50

Days mPILRA-mIgG1 + anti-PD-L1 mIgG1 mIgG1 + anti-PD-L1

SEQUENCE LISTING

```
<160> NUMBER OF SEQ ID NOS: 75

<210> SEQ ID NO 1
<211> LENGTH: 303
<212> TYPE: PRT
<213> ORGANISM: Homo sapiens

<400> SEQUENCE: 1

Met Gly Arg Pro Leu Leu Leu Pro Leu Leu Pro Leu Leu Leu Pro Pro
1               5                   10                  15

Ala Phe Leu Gln Pro Ser Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Thr Ala
    50                  55                  60

Pro Asp Val Arg Ile Ser Trp Arg Arg Gly His Phe His Arg Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
            100                 105                 110

Ser Asn Leu Gln Lys Gln Asp Gln Ser Val Tyr Phe Cys Arg Val Glu
        115                 120                 125

Leu Asp Thr Arg Ser Ser Gly Arg Gln Gln Trp Gln Ser Ile Glu Gly
    130                 135                 140

Thr Lys Leu Ser Ile Thr Gln Ala Val Thr Thr Thr Thr Gln Arg Pro
145                 150                 155                 160

Ser Ser Met Thr Thr Thr Trp Arg Leu Ser Ser Thr Thr Thr Thr Thr
                165                 170                 175
```

-continued

```
Gly Leu Arg Val Thr Gln Gly Lys Arg Arg Ser Asp Ser Trp His Ile
            180                 185                 190

Ser Leu Glu Thr Ala Val Gly Val Ala Val Ala Val Thr Val Leu Gly
        195                 200                 205

Ile Met Ile Leu Gly Leu Ile Cys Leu Leu Arg Trp Arg Arg Arg Lys
    210                 215                 220

Gly Gln Gln Arg Thr Lys Ala Thr Thr Pro Ala Arg Glu Pro Phe Gln
225                 230                 235                 240

Asn Thr Glu Glu Pro Tyr Glu Asn Ile Arg Asn Glu Gly Gln Asn Thr
                245                 250                 255

Asp Pro Lys Leu Asn Pro Lys Asp Asp Gly Ile Val Tyr Ala Ser Leu
            260                 265                 270

Ala Leu Ser Ser Ser Thr Ser Pro Arg Ala Pro Pro Ser His Arg Pro
        275                 280                 285

Leu Lys Ser Pro Gln Asn Glu Thr Leu Tyr Ser Val Leu Lys Ala
    290                 295                 300


<210> SEQ ID NO 2
<211> LENGTH: 307
<212> TYPE: PRT
<213> ORGANISM: Artificial Sequence
<220> FEATURE:
<223> OTHER INFORMATION: Cynomolgus monkey PILRA

<400> SEQUENCE: 2

Met Gly Arg Pro Leu Leu Leu Pro Leu Leu Leu Pro Leu Leu Pro Leu
1               5                   10                  15

Leu Leu Pro Pro Ala Phe Leu Gln Pro Gly Gly Ser Ala Gly Ser Gly
            20                  25                  30

Pro Ser Gly Pro Tyr Gly Val Thr Gln Arg Lys His Leu Ser Ala Pro
        35                  40                  45

Met Gly Gly Ser Val Glu Ile Pro Phe Ser Phe Tyr His Pro Trp Glu
    50                  55                  60

Leu Ala Ala Ala Pro Asn Met Lys Ile Ser Trp Arg Arg Gly Asn Phe
65                  70                  75                  80

His Gly Glu Phe Phe Tyr Arg Thr Arg Pro Ala Phe Ile His Glu Asp
                85                  90                  95

Tyr Ser Asn Arg Leu Leu Leu Asn Trp Thr Glu Gly Gln Asp Arg Gly
            100                 105                 110

Leu Leu Arg Ile Trp Asn Leu Arg Lys Glu Asp Gln Ser Val Tyr Phe
        115                 120                 125

Cys Arg Val Glu Leu Asp Thr Arg Arg Ser Gly Arg Gln Arg Trp Gln
    130                 135                 140

Ser Ile Glu Gly Thr Lys Leu Thr Ile Thr Gln Ala Val Thr Thr Thr
145                 150                 155                 160

Thr Gln Arg Pro Ser Ser Met Thr Thr Thr Arg Arg Pro Ser Ser Ala
                165                 170                 175

Thr Thr Thr Ala Gly Leu Arg Val Thr Gln Gly Lys Arg His Ser Asp
            180                 185                 190

Ser Trp His Leu Ser Leu Lys Thr Ala Val Gly Val Thr Val Ala Val
        195                 200                 205

Ala Val Leu Gly Ile Met Ile Leu Gly Leu Ile Cys Leu Leu Arg Trp
    210                 215                 220

Arg Arg Arg Lys Gly Gln Gln Arg Thr Lys Ala Thr Thr Pro Ala Lys
225                 230                 235                 240
```

-continued

```
Glu Pro Phe Gln Asn Thr Glu Glu Pro Tyr Glu Asn Ile Arg Asn Glu
                245                 250                 255

Gly Gln Asn Thr Asp Pro Lys Pro Asn Pro Lys Asp Asp Gly Ile Val
            260                 265                 270

Tyr Ala Ser Leu Ala Leu Ser Ser Ser Thr Ser Pro Arg Val Pro Pro
        275                 280                 285

Ser His His Pro Leu Lys Ser Pro Gln Asn Glu Thr Leu Tyr Ser Val
    290                 295                 300

Leu Lys Val
305


<210> SEQ ID NO 3
<211> LENGTH: 302
<212> TYPE: PRT
<213> ORGANISM: Artificial Sequence
<220> FEATURE:
<223> OTHER INFORMATION: Murine PILRA

<400> SEQUENCE: 3

Met Ala Leu Leu Ile Ser Leu Pro Gly Gly Thr Pro Ala Met Ala Gln
1               5                   10                  15

Ile Leu Leu Leu Leu Ser Ser Ala Cys Leu His Ala Gly Asn Ser Glu
            20                  25                  30

Arg Ser Asn Arg Lys Asn Gly Phe Gly Val Asn Gln Pro Glu Ser Cys
        35                  40                  45

Ser Gly Val Gln Gly Gly Ser Ile Asp Ile Pro Phe Ser Phe Tyr Phe
    50                  55                  60

Pro Trp Lys Leu Ala Lys Asp Pro Gln Met Ser Ile Ala Trp Arg Trp
65                  70                  75                  80

Lys Asp Phe His Gly Glu Phe Ile Tyr Asn Ser Ser Leu Pro Phe Ile
                85                  90                  95

His Glu His Phe Lys Gly Arg Leu Ile Leu Asn Trp Thr Gln Gly Gln
            100                 105                 110

Thr Ser Gly Val Leu Arg Ile Leu Asn Leu Lys Glu Ser Asp Gln Thr
        115                 120                 125

Arg Tyr Phe Gly Arg Val Phe Leu Gln Thr Thr Glu Gly Ile Gln Phe
    130                 135                 140

Trp Gln Ser Ile Pro Gly Thr Gln Leu Asn Val Thr Asn Ala Thr Cys
145                 150                 155                 160

Thr Pro Thr Thr Leu Pro Ser Thr Thr Ala Ala Thr Ser Ala His Thr
                165                 170                 175

Gln Asn Asp Ile Thr Glu Val Lys Ser Ala Asn Ile Gly Gly Leu Asp
            180                 185                 190

Leu Gln Thr Thr Val Gly Leu Ala Thr Ala Ala Ala Val Phe Leu Val
        195                 200                 205

Gly Val Leu Gly Leu Ile Val Phe Leu Trp Trp Lys Arg Arg Arg Gln
    210                 215                 220

Gly Gln Lys Thr Lys Ala Glu Ile Pro Ala Arg Glu Pro Leu Glu Thr
225                 230                 235                 240

Ser Glu Lys His Glu Ser Val Gly His Glu Gly Gln Cys Met Asp Pro
                245                 250                 255

Lys Glu Asn Pro Lys Asp Asn Asn Ile Val Tyr Ala Ser Ile Ser Leu
            260                 265                 270

Ser Ser Pro Thr Ser Pro Gly Thr Ala Pro Asn Leu Pro Val His Gly
        275                 280                 285
```

-continued

```
Asn Pro Gln Glu Glu Thr Val Tyr Ser Ile Val Lys Ala Lys
    290                 295                 300


<210> SEQ ID NO 4
<211> LENGTH: 7
<212> TYPE: PRT
<213> ORGANISM: Artificial Sequence
<220> FEATURE:
<223> OTHER INFORMATION: hPA-002 Heavy Chain CDR1

<400> SEQUENCE: 4

Thr Phe Gly Met Gly Val Gly
1               5


<210> SEQ ID NO 5
<211> LENGTH: 16
<212> TYPE: PRT
<213> ORGANISM: Artificial Sequence
<220> FEATURE:
<223> OTHER INFORMATION: hPA-002 heavy chain CDR2

<400> SEQUENCE: 5

His Ile Trp Trp Asp Asp Asp Lys Tyr Tyr Asn Pro Ala Leu Lys Ser
1               5                   10                  15


<210> SEQ ID NO 6
<211> LENGTH: 10
<212> TYPE: PRT
<213> ORGANISM: artificial sequence
<220> FEATURE:
<223> OTHER INFORMATION: hPA-002 Heavy chain CDR3

<400> SEQUENCE: 6

Val Glu Asp Tyr Gly Asn Pro Phe Asp Tyr
1               5                   10


<210> SEQ ID NO 7
<211> LENGTH: 11
<212> TYPE: PRT
<213> ORGANISM: artificial sequence
<220> FEATURE:
<223> OTHER INFORMATION: hPA-002 Light Chain  CDR1

<400> SEQUENCE: 7

His Ala Ser Gln Asn Ile His Val Trp Leu Asn
1               5                   10


<210> SEQ ID NO 8
<211> LENGTH: 7
<212> TYPE: PRT
<213> ORGANISM: artificial sequence
<220> FEATURE:
<223> OTHER INFORMATION: hPA-002 Light Chain CDR2

<400> SEQUENCE: 8

Lys Ala Ser Asn Leu His Thr
1               5


<210> SEQ ID NO 9
<211> LENGTH: 9
<212> TYPE: PRT
<213> ORGANISM: artificial sequence
<220> FEATURE:
<223> OTHER INFORMATION: hPA-002 Light Chain CDR3

<400> SEQUENCE: 9

Gln Gln Gly Gln Ser Tyr Pro Leu Thr
```

1 5

<210> SEQ ID NO 10
<211> LENGTH: 7
<212> TYPE: PRT
<213> ORGANISM: Artificial Sequence
<220> FEATURE:
<223> OTHER INFORMATION: hPA-005 Heavy Chain CDR1

<400> SEQUENCE: 10

Thr Phe Gly Met Gly Val Gly
1 5

<210> SEQ ID NO 11
<211> LENGTH: 16
<212> TYPE: PRT
<213> ORGANISM: artificial sequence
<220> FEATURE:
<223> OTHER INFORMATION: hPA-005 Heavy Chain CDR2

<400> SEQUENCE: 11

His Ile Trp Trp Asp Asp Asp Lys Phe Tyr Asn Pro Ala Leu Lys Ser
1 5 10 15

<210> SEQ ID NO 12
<211> LENGTH: 10
<212> TYPE: PRT
<213> ORGANISM: artificial sequence
<220> FEATURE:
<223> OTHER INFORMATION: hPA-005 Heavy Chain CDR3

<400> SEQUENCE: 12

Ile Glu Asp Tyr Gly Ser Tyr Phe Ala Tyr
1 5 10

<210> SEQ ID NO 13
<211> LENGTH: 11
<212> TYPE: PRT
<213> ORGANISM: Artificial Sequence
<220> FEATURE:
<223> OTHER INFORMATION: hPA-005 Light Chain CDR1

<400> SEQUENCE: 13

His Ala Ser Gln Asn Ile His Val Trp Leu Asn
1 5 10

<210> SEQ ID NO 14
<211> LENGTH: 7
<212> TYPE: PRT
<213> ORGANISM: Artificial Sequence
<220> FEATURE:
<223> OTHER INFORMATION: hPA-005 Light Chain CDR2

<400> SEQUENCE: 14

Lys Ala Ser Asn Leu His Thr
1 5

<210> SEQ ID NO 15
<211> LENGTH: 9
<212> TYPE: PRT
<213> ORGANISM: artificial sequence
<220> FEATURE:
<223> OTHER INFORMATION: hPA-005 Light Chain CDR3

<400> SEQUENCE: 15

Gln Gln Gly Gln Ser Tyr Pro Tyr Thr
1 5

-continued

<210> SEQ ID NO 16
<211> LENGTH: 7
<212> TYPE: PRT
<213> ORGANISM: Artificial Sequence
<220> FEATURE:
<223> OTHER INFORMATION: hPA-004 Heavy Chain CDR1

<400> SEQUENCE: 16

Ser Phe Gly Val Ala Val Gly
1               5

<210> SEQ ID NO 17
<211> LENGTH: 16
<212> TYPE: PRT
<213> ORGANISM: artificial sequence
<220> FEATURE:
<223> OTHER INFORMATION: hPA-004 Heavy Chain CDR2

<400> SEQUENCE: 17

His Ile Trp Trp Asp Asp Asp Lys Ser Tyr Asn Pro Ala Leu Lys Ser
1               5                   10                  15

<210> SEQ ID NO 18
<211> LENGTH: 10
<212> TYPE: PRT
<213> ORGANISM: artificial sequence
<220> FEATURE:
<223> OTHER INFORMATION: hPA-004 Heavy Chain CDR3

<400> SEQUENCE: 18

Ile Ala Asp Tyr Gly Asn His Phe Asp Tyr
1               5                   10

<210> SEQ ID NO 19
<211> LENGTH: 11
<212> TYPE: PRT
<213> ORGANISM: artificial sequence
<220> FEATURE:
<223> OTHER INFORMATION: hPA-004 Light Chain CDR1

<400> SEQUENCE: 19

His Ala Ser Gln Asn Ser His Val Trp Leu Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: hPA-004 Light Chain CDR2

<400> SEQUENCE: 20

Lys Ala Ser Asn Leu His Thr
1               5

<210> SEQ ID NO 21
<211> LENGTH: 9
<212> TYPE: PRT
<213> ORGANISM: artificial sequence
<220> FEATURE:
<223> OTHER INFORMATION: hPA-004 Light Chain CDR3

<400> SEQUENCE: 21

Gln Gln Gly Gln Thr Tyr Pro Phe Thr
1               5

<210> SEQ ID NO 22
<211> LENGTH: 7
<212> TYPE: PRT
<213> ORGANISM: Artificial Sequence
<220> FEATURE:
<223> OTHER INFORMATION: hPA-001 Heavy Chain CDR1

<400> SEQUENCE: 22

```
Thr Phe Gly Met Gly Val Gly
1               5
```

<210> SEQ ID NO 23
<211> LENGTH: 16
<212> TYPE: PRT
<213> ORGANISM: artificial sequence
<220> FEATURE:
<223> OTHER INFORMATION: hPA-001 Heavy Chain CDR2

<400> SEQUENCE: 23

```
His Ile Trp Trp Asp Asp Asp Lys Tyr Tyr Asn Pro Ala Leu Lys Ser
1               5                   10                  15
```

<210> SEQ ID NO 24
<211> LENGTH: 10
<212> TYPE: PRT
<213> ORGANISM: artificial sequence
<220> FEATURE:
<223> OTHER INFORMATION: hPA-001 Heavy Chain CDR3

<400> SEQUENCE: 24

```
Ile Glu Asp Tyr Gly Asn Pro Phe Asp Tyr
1               5                   10
```

<210> SEQ ID NO 25
<211> LENGTH: 11
<212> TYPE: PRT
<213> ORGANISM: artificial sequence
<220> FEATURE:
<223> OTHER INFORMATION: hPA-001 Light Chain CDR1

<400> SEQUENCE: 25

```
His Ala Ser Gln Asn Ile His Val Trp Leu Ser
1               5                   10
```

<210> SEQ ID NO 26
<211> LENGTH: 7
<212> TYPE: PRT
<213> ORGANISM: artificial sequence
<220> FEATURE:
<223> OTHER INFORMATION: hPA-001 Light Chain CDR2

<400> SEQUENCE: 26

```
Lys Ala Ser Asn Leu His Thr
1               5
```

<210> SEQ ID NO 27
<211> LENGTH: 9
<212> TYPE: PRT
<213> ORGANISM: artificial sequence
<220> FEATURE:
<223> OTHER INFORMATION: hPA-001 Light Chain CDR3

<400> SEQUENCE: 27

```
Gln Gln Gly Gln Ser Tyr Pro Leu Thr
1               5
```

-continued

```
<210> SEQ ID NO 28
<211> LENGTH: 120
<212> TYPE: PRT
<213> ORGANISM: Artificial Sequence
<220> FEATURE:
<223> OTHER INFORMATION: hPA-002 Variable Heavy Chain

<400> SEQUENCE: 28

Gln Val Thr Leu Gln Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Ser Val Asp Thr Ala Asp Ile Ala Thr Tyr Tyr
                85                  90                  95

Cys Ala Arg Val Glu Asp Tyr Gly Asn Pro Phe Asp Tyr Trp Gly Gln
            100                 105                 110

Gly Thr Thr Leu Thr Val Ser Ser
        115                 120


<210> SEQ ID NO 29
<211> LENGTH: 107
<212> TYPE: PRT
<213> ORGANISM: artificial sequence
<220> FEATURE:
<223> OTHER INFORMATION: hPA-002 Variable Light Chain

<400> SEQUENCE: 29

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile His Val Trp
            20                  25                  30

Leu Asn Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Val Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys
            100                 105


<210> SEQ ID NO 30
<211> LENGTH: 120
<212> TYPE: PRT
<213> ORGANISM: artificial sequence
<220> FEATURE:
<223> OTHER INFORMATION: hPA-005 Variable Heavy Chain

<400> SEQUENCE: 30

Gln Val Ile Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Phe
            20                  25                  30
```

```
Gly Met Gly Val Gly Trp Ile Arg Gln Pro Ser Gly Lys Gly Leu Glu
        35                  40                  45

Ser Leu Ala His Ile Trp Trp Asp Asp Asp Lys Phe Tyr Asn Pro Ala
    50                  55                  60

Leu Lys Ser Arg Leu Thr Ile Ser Lys Asp Thr Ser Lys Ser Gln Val
65                  70                  75                  80

Phe Leu Lys Ile Ala Asn Val Asp Thr Ala Asp Ile Ala Thr Tyr Tyr
                85                  90                  95

Cys Thr Arg Ile Glu Asp Tyr Gly Ser Tyr Phe Ala Tyr Trp Gly Gln
            100                 105                 110

Gly Thr Thr Leu Thr Val Ser Ser
        115                 120


<210> SEQ ID NO 31
<211> LENGTH: 107
<212> TYPE: PRT
<213> ORGANISM: artificial sequence
<220> FEATURE:
<223> OTHER INFORMATION: hPA-005 Variable Light Chain

<400> SEQUENCE: 31

Asp Val Gln Met Asn Gln Ser Pro Ser Ser Leu Ser Ala Ser Leu Gly
1               5                   10                  15

Asp Pro Ile Thr Ile Thr Cys His Ala Ser Gln Asn Ile His Val Trp
            20                  25                  30

Leu Asn Trp Tyr Gln Gln Arg Pro Gly Asn Ile Pro Arg Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105


<210> SEQ ID NO 32
<211> LENGTH: 120
<212> TYPE: PRT
<213> ORGANISM: artificial sequence
<220> FEATURE:
<223> OTHER INFORMATION: hPA-004 Variable Heavy Chain

<400> SEQUENCE: 32

Gln Val Thr Leu Lys Glu Ser Gly Pro Gly Met Leu Gln Pro Ser Gln
1               5                   10                  15

Thr Leu Ser Leu Ala Cys Ser Phe Ser Gly Phe Ser Leu Asn Ser Phe
            20                  25                  30

Gly Val Ala Val Gly Trp Ile Arg Gln Pro Ser Gly Lys Gly Leu Glu
        35                  40                  45

Trp Leu Ala His Ile Trp Trp Asp Asp Asp Lys Ser Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Leu Ala Asn Val Asp Thr Ala Asp Thr Ala Thr Tyr Tyr
                85                  90                  95

Cys Thr Arg Ile Ala Asp Tyr Gly Asn His Phe Asp Tyr Trp Gly Gln
```

100 105 110

Gly Thr Ala Leu Thr Val Ser Ser
115 120

<210> SEQ ID NO 33
<211> LENGTH: 107
<212> TYPE: PRT
<213> ORGANISM: artificial sequence
<220> FEATURE:
<223> OTHER INFORMATION: hPA-004 Variable Light Chain

<400> SEQUENCE: 33

Asp Ile Gln Met Asn Gln Ser Pro Ser Ser Leu Ser Ala Ser Leu Gly
1 5 10 15

Asp Thr Ile Thr Ile Thr Cys His Ala Ser Gln Asn Ser His Val Trp
20 25 30

Leu Ser Trp Tyr Gln Gln Lys Pro Gly Asn Ile Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Gly Phe Thr Leu Thr Ile Ser Gly Leu Gln Pro
65 70 75 80

Glu Asp Ile Ala Thr Tyr Tyr Cys Gln Gln Gly Gln Thr Tyr Pro Phe
85 90 95

Thr Phe Gly Ser Gly Thr Lys Leu Glu Ile Lys
100 105

<210> SEQ ID NO 34
<211> LENGTH: 120
<212> TYPE: PRT
<213> ORGANISM: artificial sequence
<220> FEATURE:
<223> OTHER INFORMATION: hPA-001 Variable Heavy Chain

<400> SEQUENCE: 34

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Thr Thr Phe
20 25 30

Gly Met Gly Val Gly Trp Ile Arg Gln Pro Ser Gly Lys Gly Leu Glu
35 40 45

Trp Leu Ala His Ile Trp Trp Asp Asp Asp Lys Tyr Tyr Asn Pro Ala
50 55 60

Leu Lys Ser Arg Leu Thr Ile Ser Lys Asp Ile Ser Lys Asn Gln Val
65 70 75 80

Phe Leu Lys Ile Ala Asn Val Asp Thr Ala Asp Thr Ala Thr Tyr Tyr
85 90 95

Cys Ala Arg Ile Glu Asp Tyr Gly Asn Pro Phe Asp Tyr Trp Gly Gln
100 105 110

Gly Thr Thr Leu Thr Val Ser Ser
115 120

<210> SEQ ID NO 35
<211> LENGTH: 107
<212> TYPE: PRT
<213> ORGANISM: Artificial Sequence
<220> FEATURE:
<223> OTHER INFORMATION: hPA-001 Variable Light Chain

<400> SEQUENCE: 35

-continued

```
Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile His Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys
            100                 105


<210> SEQ ID NO 36
<211> LENGTH: 30
<212> TYPE: PRT
<213> ORGANISM: artificial sequence
<220> FEATURE:
<223> OTHER INFORMATION: hPA-002 Heavy Chain Framework Region 1

<400> SEQUENCE: 36

Gln Val Thr Leu Gln Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30


<210> SEQ ID NO 37
<211> LENGTH: 14
<212> TYPE: PRT
<213> ORGANISM: artificial sequence
<220> FEATURE:
<223> OTHER INFORMATION: hPA-002 Heavy Chain Framework Region 2

<400> SEQUENCE: 37

Trp Ile Arg Gln Pro Ser Gly Lys Gly Leu Glu Trp Leu Ala
1               5                   10


<210> SEQ ID NO 38
<211> LENGTH: 32
<212> TYPE: PRT
<213> ORGANISM: artificial sequence
<220> FEATURE:
<223> OTHER INFORMATION: hPA-002 Heavy Chain Framework Region 3

<400> SEQUENCE: 38

Arg Leu Thr Ile Ser Lys Asp Thr Ser Lys Asn Gln Val Phe Leu Lys
1               5                   10                  15

Ile Ala Ser Val Asp Thr Ala Asp Ile Ala Thr Tyr Tyr Cys Ala Arg
            20                  25                  30


<210> SEQ ID NO 39
<211> LENGTH: 11
<212> TYPE: PRT
<213> ORGANISM: artificial sequence
<220> FEATURE:
<223> OTHER INFORMATION: hPA-002 Heavy Chain Framework Region 4

<400> SEQUENCE: 39

Trp Gly Gln Gly Thr Thr Leu Thr Val Ser Ser
1               5                   10
```

<210> SEQ ID NO 40
<211> LENGTH: 23
<212> TYPE: PRT
<213> ORGANISM: artificial sequence
<220> FEATURE:
<223> OTHER INFORMATION: hPA-002 Light Chain Framework Region 1

<400> SEQUENCE: 40

Asp Ile Gln Met Asn Gln Ser Pro Ser Ser Leu Ser Ala Ser Leu Gly
1 5 10 15

Asp Thr Ile Thr Ile Thr Cys
20

<210> SEQ ID NO 41
<211> LENGTH: 15
<212> TYPE: PRT
<213> ORGANISM: artificial sequence
<220> FEATURE:
<223> OTHER INFORMATION: hPA-002 Light Chain Framework Region 2

<400> SEQUENCE: 41

Trp Tyr Gln Gln Lys Pro Gly Asn Ile Pro Lys Leu Leu Ile Tyr
1 5 10 15

<210> SEQ ID NO 42
<211> LENGTH: 32
<212> TYPE: PRT
<213> ORGANISM: artificial sequence
<220> FEATURE:
<223> OTHER INFORMATION: hPA-002 Light Chain Framework Region 3

<400> SEQUENCE: 42

Gly Val Pro Ser Arg Phe Ser Gly Ser Gly Ser Gly Thr Gly Phe Thr
1 5 10 15

Val Thr Ile Ser Ser Leu Gln Pro Glu Asp Ile Ala Thr Tyr Tyr Cys
20 25 30

<210> SEQ ID NO 43
<211> LENGTH: 10
<212> TYPE: PRT
<213> ORGANISM: artificial sequence
<220> FEATURE:
<223> OTHER INFORMATION: hPA-002 Light Chain Framework Region 4

<400> SEQUENCE: 43

Phe Gly Ala Gly Thr Lys Leu Glu Leu Lys
1 5 10

<210> SEQ ID NO 44
<211> LENGTH: 30
<212> TYPE: PRT
<213> ORGANISM: Artificial Sequence
<220> FEATURE:
<223> OTHER INFORMATION: hPA-005 Heavy Chain Framework Region 1

<400> SEQUENCE: 44

Gln Val Ile Leu Lys Glu Ser Gly Pro Gly Ile Leu Gln Ser Ser Gln
1 5 10 15

Thr Leu Ser Leu Thr Cys Ser Phe Ser Gly Phe Ser Leu Ser
20 25 30

<210> SEQ ID NO 45
<211> LENGTH: 14
<212> TYPE: PRT

<213> ORGANISM: artificial sequence
<220> FEATURE:
<223> OTHER INFORMATION: hPA-005 Heavy Chain Framework Region 2

<400> SEQUENCE: 45

Trp Ile Arg Gln Pro Ser Gly Lys Gly Leu Glu Ser Leu Ala
1 5 10

<210> SEQ ID NO 46
<211> LENGTH: 32
<212> TYPE: PRT
<213> ORGANISM: artificial sequence
<220> FEATURE:
<223> OTHER INFORMATION: hPA-005 Heavy Chain Framework Region 3

<400> SEQUENCE: 46

Arg Leu Thr Ile Ser Lys Asp Thr Ser Lys Ser Gln Val Phe Leu Lys
1 5 10 15

Ile Ala Asn Val Asp Thr Ala Asp Ile Ala Thr Tyr Tyr Cys Thr Arg
20 25 30

<210> SEQ ID NO 47
<211> LENGTH: 11
<212> TYPE: PRT
<213> ORGANISM: artificial sequence
<220> FEATURE:
<223> OTHER INFORMATION: hPA-005 Heavy Chain Framework Region 4

<400> SEQUENCE: 47

Trp Gly Gln Gly Thr Thr Leu Thr Val Ser Ser
1 5 10

<210> SEQ ID NO 48
<211> LENGTH: 23
<212> TYPE: PRT
<213> ORGANISM: artificial sequence
<220> FEATURE:
<223> OTHER INFORMATION: hPA-005 Light Chain Framework Region 1

<400> SEQUENCE: 48

Asp Val Gln Met Asn Gln Ser Pro Ser Ser Leu Ser Ala Ser Leu Gly
1 5 10 15

Asp Pro Ile Thr Ile Thr Cys
20

<210> SEQ ID NO 49
<211> LENGTH: 15
<212> TYPE: PRT
<213> ORGANISM: artificial sequence
<220> FEATURE:
<223> OTHER INFORMATION: hPA-005 Light Chain Framework Region 2

<400> SEQUENCE: 49

Trp Tyr Gln Gln Arg Pro Gly Asn Ile Pro Arg Leu Leu Ile Tyr
1 5 10 15

<210> SEQ ID NO 50
<211> LENGTH: 32
<212> TYPE: PRT
<213> ORGANISM: artificial sequence
<220> FEATURE:
<223> OTHER INFORMATION: hPA-005 Light Chain Framework Region 3

<400> SEQUENCE: 50

Gly Val Pro Ser Arg Phe Ser Gly Ser Gly Ser Gly Thr Gly Phe Thr
1 5 10 15

Leu Thr Ile Ser Ser Leu Gln Pro Glu Asp Ile Ala Thr Tyr Tyr Cys
20 25 30

<210> SEQ ID NO 51
<211> LENGTH: 10
<212> TYPE: PRT
<213> ORGANISM: artificial sequence
<220> FEATURE:
<223> OTHER INFORMATION: hPA-005 Light Chain Framework Region 4

<400> SEQUENCE: 51

Phe Gly Gly Gly Thr Lys Leu Glu Ile Lys
1 5 10

<210> SEQ ID NO 52
<211> LENGTH: 30
<212> TYPE: PRT
<213> ORGANISM: artificial sequence
<220> FEATURE:
<223> OTHER INFORMATION: hPA-004 Heavy Chain Framework Region 1

<400> SEQUENCE: 52

Gln Val Thr Leu Lys Glu Ser Gly Pro Gly Met Leu Gln Pro Ser Gln
1 5 10 15

Thr Leu Ser Leu Ala Cys Ser Phe Ser Gly Phe Ser Leu Asn
20 25 30

<210> SEQ ID NO 53
<211> LENGTH: 14
<212> TYPE: PRT
<213> ORGANISM: artificial sequence
<220> FEATURE:
<223> OTHER INFORMATION: hPA-004 Heavy Chain Framework Region 2

<400> SEQUENCE: 53

Trp Ile Arg Gln Pro Ser Gly Lys Gly Leu Glu Trp Leu Ala
1 5 10

<210> SEQ ID NO 54
<211> LENGTH: 32
<212> TYPE: PRT
<213> ORGANISM: artificial sequence
<220> FEATURE:
<223> OTHER INFORMATION: hPA-004 Heavy Chain Framework Region 3

<400> SEQUENCE: 54

Arg Leu Thr Ile Ser Lys Asp Thr Ser Lys Asn Gln Val Phe Leu Lys
1 5 10 15

Leu Ala Asn Val Asp Thr Ala Asp Thr Ala Thr Tyr Tyr Cys Thr Arg
20 25 30

<210> SEQ ID NO 55
<211> LENGTH: 11
<212> TYPE: PRT
<213> ORGANISM: artificial sequence
<220> FEATURE:
<223> OTHER INFORMATION: hPA-004 Heavy Chain Framework Region 4

<400> SEQUENCE: 55

Trp Gly Gln Gly Thr Ala Leu Thr Val Ser Ser
1 5 10

<210> SEQ ID NO 56
<211> LENGTH: 23
<212> TYPE: PRT

```
<213> ORGANISM: artificial sequence
<220> FEATURE:
<223> OTHER INFORMATION: hPA-004 Light Chain Framework Region 1

<400> SEQUENCE: 56

Asp Ile Gln Met Asn Gln Ser Pro Ser Ser Leu Ser Ala Ser Leu Gly
1               5                   10                  15

Asp Thr Ile Thr Ile Thr Cys
            20


<210> SEQ ID NO 57
<211> LENGTH: 15
<212> TYPE: PRT
<213> ORGANISM: artificial sequence
<220> FEATURE:
<223> OTHER INFORMATION: hPA-004 Light Chain Framework Region 2

<400> SEQUENCE: 57

Trp Tyr Gln Gln Lys Pro Gly Asn Ile Pro Lys Leu Leu Ile Tyr
1               5                   10                  15


<210> SEQ ID NO 58
<211> LENGTH: 32
<212> TYPE: PRT
<213> ORGANISM: artificial sequence
<220> FEATURE:
<223> OTHER INFORMATION: hPA-004 Light Chain Framework Region 3

<400> SEQUENCE: 58

Gly Val Pro Ser Arg Phe Ser Gly Ser Gly Ser Gly Thr Gly Phe Thr
1               5                   10                  15

Leu Thr Ile Ser Gly Leu Gln Pro Glu Asp Ile Ala Thr Tyr Tyr Cys
            20                  25                  30


<210> SEQ ID NO 59
<211> LENGTH: 10
<212> TYPE: PRT
<213> ORGANISM: artificial sequence
<220> FEATURE:
<223> OTHER INFORMATION: hPA-004 Light Chain Framework Region 4

<400> SEQUENCE: 59

Phe Gly Ser Gly Thr Lys Leu Glu Ile Lys
1               5                   10


<210> SEQ ID NO 60
<211> LENGTH: 30
<212> TYPE: PRT
<213> ORGANISM: artificial sequence
<220> FEATURE:
<223> OTHER INFORMATION: hPA-001 Heavy Chain Framework Region 1

<400> SEQUENCE: 60

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr
            20                  25                  30


<210> SEQ ID NO 61
<211> LENGTH: 14
<212> TYPE: PRT
<213> ORGANISM: artificial sequence
<220> FEATURE:
<223> OTHER INFORMATION: hPA-001 Heavy Chain Framework Region 2

<400> SEQUENCE: 61
```

Trp Ile Arg Gln Pro Ser Gly Lys Gly Leu Glu Trp Leu Ala
1 5 10

<210> SEQ ID NO 62
<211> LENGTH: 32
<212> TYPE: PRT
<213> ORGANISM: artificial sequence
<220> FEATURE:
<223> OTHER INFORMATION: hPA-001 Heavy Chain Framework Region 3

<400> SEQUENCE: 62

Arg Leu Thr Ile Ser Lys Asp Ile Ser Lys Asn Gln Val Phe Leu Lys
1 5 10 15

Ile Ala Asn Val Asp Thr Ala Asp Thr Ala Thr Tyr Tyr Cys Ala Arg
20 25 30

<210> SEQ ID NO 63
<211> LENGTH: 11
<212> TYPE: PRT
<213> ORGANISM: artificial sequence
<220> FEATURE:
<223> OTHER INFORMATION: hPA-001 Heavy Chain Framework Region 4

<400> SEQUENCE: 63

Trp Gly Gln Gly Thr Thr Leu Thr Val Ser Ser
1 5 10

<210> SEQ ID NO 64
<211> LENGTH: 23
<212> TYPE: PRT
<213> ORGANISM: artificial sequence
<220> FEATURE:
<223> OTHER INFORMATION: hPA-001 Light Chain Framework Region 1

<400> SEQUENCE: 64

Asp Ile Gln Met Asn Gln Ser Pro Ser Ser Leu Ser Ala Ser Leu Gly
1 5 10 15

Asp Thr Ile Thr Ile Thr Cys
20

<210> SEQ ID NO 65
<211> LENGTH: 15
<212> TYPE: PRT
<213> ORGANISM: artificial sequence
<220> FEATURE:
<223> OTHER INFORMATION: hPA-001 Light Chain Framework Region 2

<400> SEQUENCE: 65

Trp Tyr Gln Gln Lys Pro Gly Asn Ile Pro Lys Leu Leu Ile Tyr
1 5 10 15

<210> SEQ ID NO 66
<211> LENGTH: 32
<212> TYPE: PRT
<213> ORGANISM: artificial sequence
<220> FEATURE:
<223> OTHER INFORMATION: hPA-001 Light Chain Framework Region 3

<400> SEQUENCE: 66

Gly Val Pro Ser Arg Phe Ser Gly Ser Gly Ser Gly Thr Gly Phe Thr
1 5 10 15

Leu Thr Ile Ser Ser Leu Gln Pro Glu Asp Ile Ala Thr Tyr Tyr Cys
20 25 30

<210> SEQ ID NO 67
<211> LENGTH: 10
<212> TYPE: PRT
<213> ORGANISM: artificial sequence
<220> FEATURE:
<223> OTHER INFORMATION: hPA-001 Light Chain Framework Region 4

<400> SEQUENCE: 67

Phe Gly Ala Gly Thr Lys Leu Glu Leu Lys
1 5 10

<210> SEQ ID NO 68
<211> LENGTH: 227
<212> TYPE: PRT
<213> ORGANISM: Homo sapiens

<400> SEQUENCE: 68

Met Gly Arg Pro Leu Leu Leu Pro Leu Leu Leu Leu Leu Gln Pro Pro
1 5 10 15

Ala Phe Leu Gln Pro Gly Gly Ser Thr Gly Ser Gly Pro Ser Tyr Leu
20 25 30

Tyr Gly Val Thr Gln Pro Lys His Leu Ser Ala Ser Met Gly Gly Ser
35 40 45

Val Glu Ile Pro Phe Ser Phe Tyr Tyr Pro Trp Glu Leu Ala Ile Val
50 55 60

Pro Asn Val Arg Ile Ser Trp Arg Arg Gly His Phe His Gly Gln Ser
65 70 75 80

Phe Tyr Ser Thr Arg Pro Pro Ser Ile His Lys Asp Tyr Val Asn Arg
85 90 95

Leu Phe Leu Asn Trp Thr Glu Gly Gln Glu Ser Gly Phe Leu Arg Ile
100 105 110

Ser Asn Leu Arg Lys Glu Asp Gln Ser Val Tyr Phe Cys Arg Val Glu
115 120 125

Leu Asp Thr Arg Arg Ser Gly Arg Gln Gln Leu Gln Ser Ile Lys Gly
130 135 140

Thr Lys Leu Thr Ile Thr Gln Ala Val Thr Thr Thr Thr Thr Trp Arg
145 150 155 160

Pro Ser Ser Thr Thr Thr Ile Ala Gly Leu Arg Val Thr Glu Ser Lys
165 170 175

Gly His Ser Glu Ser Trp His Leu Ser Leu Asp Thr Ala Ile Arg Val
180 185 190

Ala Leu Ala Val Ala Val Leu Lys Thr Val Ile Leu Gly Leu Leu Cys
195 200 205

Leu Leu Leu Leu Trp Trp Arg Arg Arg Lys Gly Ser Arg Ala Pro Ser
210 215 220

Ser Asp Phe
225

<210> SEQ ID NO 69
<211> LENGTH: 232
<212> TYPE: PRT
<213> ORGANISM: artificial sequence
<220> FEATURE:
<223> OTHER INFORMATION: human IgG1 Fc domain

<400> SEQUENCE: 69

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro

```
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 70
<211> LENGTH: 232
<212> TYPE: PRT
<213> ORGANISM: artificial sequence
<220> FEATURE:
<223> OTHER INFORMATION: mutated human IgG1 Fc

<400> SEQUENCE: 70

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Ser Lys Ala
            100                 105                 110

Phe Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
```

-continued

```
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 71
<211> LENGTH: 232
<212> TYPE: PRT
<213> ORGANISM: artificial sequence
<220> FEATURE:
<223> OTHER INFORMATION: mutated human IgG1 Fc

<400> SEQUENCE: 71

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 72
<211> LENGTH: 229
<212> TYPE: PRT
<213> ORGANISM: artificial sequence
<220> FEATURE:
<223> OTHER INFORMATION: human IgG4 Fc
```

<400> SEQUENCE: 72

Glu Ser Lys Tyr Gly Pro Pro Cys Pro Ser Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 73
<211> LENGTH: 229
<212> TYPE: PRT
<213> ORGANISM: artificial sequence
<220> FEATURE:
<223> OTHER INFORMATION: mutated human IgG4 Fc

<400> SEQUENCE: 73

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

-continued

```
Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 74
<211> LENGTH: 445
<212> TYPE: PRT
<213> ORGANISM: artificial sequence
<220> FEATURE:
<223> OTHER INFORMATION: soluble human PILRA hIgG1 Fc

<400> SEQUENCE: 74

Gln Pro Ser Gly Ser Thr Gly Ser Gly Pro Ser Tyr Leu Tyr Gly Val
1               5                   10                  15

Thr Gln Pro Lys His Leu Ser Ala Ser Met Gly Gly Ser Val Glu Ile
            20                  25                  30

Pro Phe Ser Phe Tyr Tyr Pro Trp Glu Leu Ala Thr Ala Pro Asp Val
        35                  40                  45

Arg Ile Ser Trp Arg Arg Gly His Phe His Gly Gln Ser Phe Tyr Ser
    50                  55                  60

Thr Arg Pro Pro Ser Ile His Lys Asp Tyr Val Asn Arg Leu Phe Leu
65                  70                  75                  80

Asn Trp Thr Glu Gly Gln Lys Ser Gly Phe Leu Arg Ile Ser Asn Leu
                85                  90                  95

Gln Lys Gln Asp Gln Ser Val Tyr Phe Cys Arg Val Glu Leu Asp Thr
            100                 105                 110

Arg Ser Ser Gly Arg Gln Gln Trp Gln Ser Ile Glu Gly Thr Lys Leu
        115                 120                 125

Ser Ile Thr Gln Gly Gln Gln Arg Thr Lys Ala Thr Thr Pro Ala Arg
    130                 135                 140

Glu Pro Phe Gln Asn Thr Glu Glu Pro Tyr Glu Asn Ile Arg Asn Glu
145                 150                 155                 160

Gly Gln Asn Thr Asp Pro Lys Leu Asn Pro Lys Leu His Leu Thr Gln
                165                 170                 175

Ser Thr Ser Gln Pro Pro Ser Pro Gln Glu Pro Pro Glu Arg Asp Pro
            180                 185                 190

Val Leu Cys Leu Lys Gly Leu Thr Asn Gly Gln Pro Ser Gln Asp Ala
        195                 200                 205

Asp Asp Asp Asp Lys Glu Pro Lys Ser Ser Asp Lys Thr His Thr Cys
    210                 215                 220

Pro Pro Cys Pro Ala Pro Glu Leu Leu Gly Gly Pro Ser Val Phe Leu
225                 230                 235                 240
```

-continued

```
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 75
<211> LENGTH: 428
<212> TYPE: PRT
<213> ORGANISM: artificial sequence
<220> FEATURE:
<223> OTHER INFORMATION: PILRA mFc

<400> SEQUENCE: 75

Met Gly Arg Pro Leu Leu Leu Pro Leu Leu Pro Leu Leu Leu Pro Pro
1               5                   10                  15

Ala Phe Leu Gln Pro Ser Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Thr Ala
    50                  55                  60

Pro Asp Val Arg Ile Ser Trp Arg Arg Gly His Phe His Gly Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
            100                 105                 110

Ser Asn Leu Gln Lys Gln Asp Gln Ser Val Tyr Phe Cys Arg Val Glu
        115                 120                 125

Leu Asp Thr Arg Ser Ser Gly Arg Gln Gln Trp Gln Ser Ile Glu Gly
    130                 135                 140

Thr Lys Leu Ser Ile Thr Gln Ala Val Thr Thr Thr Thr Gln Arg Pro
145                 150                 155                 160
```

-continued

```
Ser Ser Met Thr Thr Thr Trp Arg Leu Ser Ser Thr Thr Thr Thr Thr
                165                 170                 175

Gly Leu Arg Val Thr Gln Gly Lys Arg Arg Ser Asp Ser Trp His Ile
            180                 185                 190

Ser Leu Glu Thr Ala Gly Gly Ser Gly Val Pro Arg Asp Cys Gly Cys
        195                 200                 205

Lys Pro Cys Ile Cys Thr Val Pro Glu Val Ser Ser Val Phe Ile Phe
    210                 215                 220

Pro Pro Lys Pro Lys Asp Val Leu Thr Ile Thr Leu Thr Pro Lys Val
225                 230                 235                 240

Thr Cys Val Val Val Asp Ile Ser Lys Asp Asp Pro Glu Val Gln Phe
                245                 250                 255

Ser Trp Phe Val Asp Asp Val Glu Val His Thr Ala Gln Thr Gln Pro
            260                 265                 270

Arg Glu Glu Gln Phe Asn Ser Thr Phe Arg Ser Val Ser Glu Leu Pro
        275                 280                 285

Ile Met His Gln Asp Trp Leu Asn Gly Lys Glu Phe Lys Cys Arg Val
    290                 295                 300

Asn Ser Ala Ala Phe Pro Ala Pro Ile Glu Lys Thr Ile Ser Lys Thr
305                 310                 315                 320

Lys Gly Arg Pro Lys Ala Pro Gln Val Tyr Thr Ile Pro Pro Pro Lys
                325                 330                 335

Glu Gln Met Ala Lys Asp Lys Val Ser Leu Thr Cys Met Ile Thr Asp
            340                 345                 350

Phe Phe Pro Glu Asp Ile Thr Val Glu Trp Gln Trp Asn Gly Gln Pro
        355                 360                 365

Ala Glu Asn Tyr Lys Asn Thr Gln Pro Ile Met Asp Thr Asp Gly Ser
    370                 375                 380

Tyr Phe Ile Tyr Ser Lys Leu Asn Val Gln Lys Ser Asn Trp Glu Ala
385                 390                 395                 400

Gly Asn Thr Phe Thr Cys Ser Val Leu His Glu Gly Leu His Asn His
                405                 410                 415

His Thr Glu Lys Ser Leu Ser His Ser Pro Gly Lys
            420                 425
```

PILRA ANTIBODIES AND METHODS OF USE THEREOF

CROSS REFERENCE TO RELATED APPLICATIONS

This application is a 35 U.S.C. § 371 National Phase Application of International Application No. PCT/US2021/018354, filed Feb. 17, 2021, which claims the benefit of U.S. Provisional Application Nos. 62/978,106, filed Feb. 18, 2020, and 63/075,440, filed Sep. 8, 2020, each of which is hereby incorporated by reference in its entirety.

REFERENCE TO A SEQUENCE LISTING SUBMITTED ELECTRONICALLY VIA EFS-WEB

The content of the electronically submitted sequence listing (Name: 4503_0090002_Seqlisting_ST25.txt; Size: 52,192 bytes; and Date of Creation: Jan. 30, 2023) is incorporated herein by reference in its entirety.

1. FIELD

The present disclosure relates to antibodies that specifically bind to human PILRA, compositions comprising such antibodies, and methods of making and using antibodies that specifically bind to human PILRA.

2. DESCRIPTION OF RELATED ART

Paired immunoglobulin-like type 2 receptor alpha (PILRA) is a cell surface receptor that is expressed on various innate immune cells of the myeloid lineage, such as monocytes, macrophages, microglia (in the CNS), dendritic cells and neutrophils. PILRA is an inhibitory receptor containing an intracellular ITIM domain and an extracellular IgV domain, and its ligands include specific sialylated O-glycosylated proteins. PILRA is also the entry receptor for herpes simplex virus 1 (HSV-1). A naturally occurring allele in the PILRA gene results in a missense variant (G78 to R78) in the encoded PILRA protein. The R78 variant of PILRA is associated with reduced risk of Alzheimer's disease. This variant is also reported to reduce binding of PILRA to several of its ligands by altering access to the sialic acid binding pocket of PILRA. It has been proposed that this variant protects individuals from Alzheimer's disease by reducing inhibitory signaling in microglia and reducing microglial infection during HSV-1 recurrence.

Given the expression and function of PILRA, provided herein are antibodies that specifically bind to human PILRA. Such antibodies may reduce inhibitory signaling of PILRA by blocking the binding of PILRA to ligands and/or by downregulating cell surface PILRA. Such antibodies may be used to activate myeloid cells and to treat diseases in which myeloid cell activation is desired, including cancer and neurodegenerative diseases such as Alzheimer's disease. These and other compositions and methods are provided herein.

3. SUMMARY

Provided herein are isolated antibodies and antigen-binding fragments thereof that specifically bind to human PILRA and methods of use thereof.

In some aspects provided herein, an isolated antibody or antigen-binding fragment thereof that specifically binds to human PILRA blocks binding of PILRA to one or more of its ligands. In some aspects, an isolated antibody or antigen-binding fragment thereof that specifically binds to human PILRA downregulates cell surface PILRA. In some aspects, an isolated antibody or antigen-binding fragment thereof that specifically binds to human PILRA blocks binding of PILRA to one or more of its ligands and PILRA downregulates cell surface PILRA.

In some aspects, the antibody or antigen-binding fragment thereof blocks binding of residue Arg126 of human PILRA (SEQ ID NO:1) to one or more ligands of PILRA.

In some aspects, the antibody or antigen-binding fragment thereof blocks binding of PILRA-Fc to human T-cells by at least 70%, at least 75%, at least 80%, at least 85%, at least 90%, at least 95% or at least 98%.

In some aspects, the antibody or antigen-binding fragment thereof downregulates cell surface PILRA by at least 10%, at least 20%, at least 30%, at least 40%, or at least 50% after 30 minutes at 37° C.

In some aspects, an isolated antibody or antigen-binding fragment thereof that specifically binds to human PILRA comprises the heavy chain variable region (VH) complementarity determining region (CDR) 1, VH CDR2, VH CDR3 and light chain variable region (VL) CDR1, CDR2, and CDR3 sequences of: SEQ ID NOs:4-9, respectively; SEQ ID NOs:10-15, respectively; SEQ ID NOs:16-21, respectively; or SEQ ID NOs:22-27, respectively.

In some aspects, an isolated antibody or antigen-binding fragment thereof competitively inhibits binding of a reference antibody to human PILRA, wherein the reference antibody comprises a heavy chain variable region and a light chain variable region comprising the amino acid sequences of: SEQ ID NOs:28 and 29, respectively; SEQ ID NOs:30 and 31, respectively; SEQ ID NOs:32 and 33, respectively; or SEQ ID NOs:34 and 35, respectively.

In some aspects, an isolated antibody or antigen-binding fragment thereof binds to the same human PILRA epitope as an antibody comprising a heavy chain variable region and a light chain variable region comprising the amino acid sequences of: SEQ ID NOs:28 and 29, respectively; SEQ ID NOs:30 and 31, respectively; SEQ ID NOs:32 and 33, respectively; or SEQ ID NOs:34 and 35, respectively.

In some aspects, an isolated antibody or antigen-binding fragment thereof that specifically binds to human PILRA comprises the VH CDR1, VH CDR2, VH CDR3, VL CDR1, VL CDR2, and VL CDR3 of an antibody selected from the group consisting of hPA-002, hPA-005, hPA-004, or hPA-001. In some aspects, the CDRs are the Kabat-defined CDRs, the Chothia-defined CDRs, the IMGT-defined CDRs, or the AbM-defined CDRs.

In some aspects, the antibody or antigen-binding fragment thereof comprises a VH comprising the amino acid sequence of SEQ ID NO:28, 30, 32, or 34. In some aspects, the antibody or antigen-binding fragment thereof comprises a VL comprising the amino acid sequence of SEQ ID NO:29, 31, 33, or 35.

In some aspects, the antibody or antigen-binding fragment comprises a heavy chain variable region and a light chain variable region comprising the amino acid sequences of: SEQ ID NOs:28 and 29, respectively; SEQ ID NOs:30 and 31, respectively; SEQ ID NOs:32 and 33, respectively; or SEQ ID NOs:34 and 35, respectively. In some aspects, an antibody or antigen-binding fragment thereof that specifically binds to human PILRA is a humanized form or an antibody that comprises a heavy chain variable region and a light chain variable region comprising the amino acid sequences of: SEQ ID NOs:28 and 29, respectively; SEQ ID NOs:30 and 31, respectively; SEQ ID NOs:32 and 33, respectively; or SEQ ID NOs:34 and 35, respectively In some aspects, an isolated antibody or antigen-binding fragment thereof that specifically binds to human PILRA comprises a heavy chain variable region and a light chain variable region, wherein the heavy chain variable region comprises the amino acid sequence of SEQ ID NO:28, 30, 32, or 34.

In some aspects, an isolated antibody or antigen-binding fragment thereof that specifically binds to human PILRA comprises a heavy chain variable region and a light chain variable region, wherein the light chain variable region comprises the amino acid sequence of SEQ ID NO:29, 31, 33, or 35.

In some aspects of the antibodies or antigen-binding fragments thereof provided herein that downregulate cell surface PILRA, the downregulation is dose-dependent.

In some aspects of the antibodies or antigen-binding fragments thereof provided herein that block binding of PILRA to one or more of its ligands, the antibody or antigen-binding fragment thereof blocks binding of residue Arg126 of human PILRA (SEQ ID NO:1) to one or more ligands of PILRA.

In some aspects of the antibodies or antigen-binding fragments thereof provided herein that block binding of PILRA to one or more of its ligands, the blocking is dose-dependent.

In some aspects, the antibody or antigen-binding fragment thereof activates myeloid cells. In some aspects, the antibody or antigen-binding fragment thereof promotes myeloid cell differentiation. In some aspects, the antibody or antigen-binding fragment thereof increases MIP1b production by myeloid cells. In some aspects, the antibody or antigen-binding fragment thereof blocks binding of PILRA to NPDC1. In some aspects, the activation of myeloid cells, the promotion of myeloid cell differentiation, the increase in MIP1b production, and/or the blocking of ligand binding is dose-dependent.

In some aspects, the antibody or antigen-binding fragment thereof binds to cynomolgus monkey PILRA. In some aspects, the antibody or antigen-binding fragment thereof does not bind to human PILRB. In some aspects, the antibody or antigen-binding fragment thereof binds to the extracellular domain of human PILRA. In some aspects, the antibody or antigen-binding fragment thereof binds to an epitope in amino acids 20-197 of SEQ ID NO:1.

In some aspects, antibody 2175B does not competitively inhibit binding of the antibody or antigen-binding fragment thereof to human PILRA.

In some aspects, the antibody or antigen-binding fragment comprises a heavy chain constant region and a light chain constant region. In some aspects, the heavy chain constant region is an isotype selected from the group consisting of human $IgG_1$, $IgG_2$, $IgG_3$, and $IgG_4$ isotypes. In some aspects, the antibody or antigen-binding fragment comprises an Fc domain that is engineered to reduce effector function.

In some aspects, the antibody or antigen-binding fragment comprises a heavy chain constant region and a light chain constant region, wherein the heavy chain constant region is a human $IgG_1$ heavy chain constant region, and wherein the light chain constant region is a human IgGκ light chain constant region.

In some aspects, the antibody or antigen-binding fragment is a monoclonal antibody. In some aspects, the antibody or antigen-binding fragment thereof is a murine, chimeric, humanized, or human antibody or antigen-binding fragment thereof.

In some aspects, the antibody or antigen-binding fragment is a full length antibody. In some aspects, the antibody or antigen binding fragment is an antigen binding fragment. In some aspects, the antigen binding fragment is a Fab, Fab', $F(ab')_2$, single chain Fv (scFv), disulfide linked Fv, V-NAR domain, IgNar, intrabody, IgGΔCH2, minibody, $F(ab')_3$, tetrabody, triabody, diabody, single-domain antibody, DVD-Ig, Fcab, $mAb^2$, $(scFv)_2$, or scFv-Fc.

In some aspects, the antibody or antigen-binding fragment thereof of any one of claims 1-34, further comprising a detectable label.

In some aspects provided herein, an isolated polynucleotide comprises a nucleic acid molecule encoding the heavy chain variable region or heavy chain of an antibody or antigen-binding fragment thereof provided herein. In some aspects, the nucleic acid molecule encodes the VH of SEQ ID NO:28, 30, 32, or 34.

In some aspects, an isolated polynucleotide comprises a nucleic acid molecule encoding the light chain variable region or light chain of an antibody or antigen-binding fragment thereof provided herein. In some aspects, the nucleic acid molecule encodes the VL of SEQ ID NO:29, 31, 33, or 35.

In some aspects, an isolated polynucleotide comprises a nucleic acid molecule encoding the heavy chain variable region or heavy chain of an antibody or antigen-binding fragment thereof provided herein and the light chain variable region or light chain of the antibody or antigen-binding fragment thereof.

In some aspects provided herein, an isolated vector comprises a polynucleotide provided herein.

In some aspects provided herein, a host cell comprises (a) a polynucleotide provided herein, (b) a vector provided herein, or (c) a first vector comprising a light chain variable region or light chain-encoding polynucleotide provided herein and a second vector comprising a heavy chain variable region or heavy chain-encoding polynucleotide provided herein. In some aspects, the host cell is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

In some aspects provided herein, a method of producing an antibody or antigen-binding fragment thereof that binds to human PILRA comprises culturing a host cell provided herein so that the nucleic acid molecule is expressed and the antibody or antigen-binding fragment thereof is produced. In some aspects, the method further comprises isolating the antibody or antigen-binding fragment thereof from the culture.

In some aspects provided herein, an isolated antibody or antigen-binding fragment thereof that specifically binds to human PILRA is encoded by a polynucleotide provided herein or is produced by a method provided herein.

In some aspects provided herein, a pharmaceutical composition comprises an antibody or antigen-binding fragment provided herein and a pharmaceutically acceptable excipient.

In some aspects provided herein, a method for downregulating cell surface PILRA comprises contacting a cell expressing PILRA on its surface with an antibody or antigen-binding fragment thereof provided herein or a pharmaceutical composition provided herein.

In some aspects, a method for inhibiting binding of PILRA to a PILRA ligand comprises contacting PILRA with an antibody or antigen-binding fragment thereof provided herein or a pharmaceutical composition provided herein in the presence of the PILRA ligand, optionally wherein the PILRA and/or the PILRA ligand is expressed on a cell. In some aspects, the PILRA ligand is NPDC1. In some aspects, the PILRA ligand is expressed on a T cell.

In some aspects, a method for increasing myeloid cell activation comprises contacting the myeloid cell with an antibody or antigen-binding fragment thereof provided herein or a pharmaceutical composition provided herein. In some aspects, the myeloid cell activation is Fc receptor-mediated.

In some aspects, a method for promoting myeloid cell differentiation comprises contacting the myeloid cell with an antibody or antigen-binding fragment thereof provided herein or a pharmaceutical composition provided herein.

In some aspects, a method for increasing myeloid cell production of MIP1b comprises contacting the myeloid cell with an antibody or antigen-binding fragment thereof provided herein or a pharmaceutical composition provided herein.

In some aspects, the contacting is in vitro. In some aspects, the contacting is in a subject.

In some aspects, a method of treating cancer in a patient comprises administering to the patient a therapeutically effective amount of an antibody or antigen-binding fragment thereof provided herein or a pharmaceutical composition provided herein. In some aspects, the cancer is a solid tumor in which myeloid cells have infiltrated the tumor microenvironment. In some aspects, the cancer is selected from glioblastoma, head and neck cancer, kidney cancer (optionally wherein the kidney cancer is kidney clear cell cancer), pancreatic cancer, and breast cancer. In some aspects, the method further comprises administering an antagonist of an inhibitory immune checkpoint molecule. In some aspects, the immune checkpoint molecule is PD-1 or PD-L1. In some aspects, the antagonist of PD-1 is an anti-PD-1 antibody or antibody fragment thereof. In some aspects, the anti-PD-1 antibody or antigen-binding fragment thereof is selected from the group consisting of nivolumab, pembrolizumab, MEDI-0680 (AMP-514), camrelizumab (SHR-1210), tislelizumab (BGB-A317), and spartalizumab (NPVPDR001, NVS240118, PDR001). In some aspects, the antagonist of PD-L1 is an anti-PD-L1 antibody or antigen-binding fragment thereof. In some aspects, the anti-PD-L1 antibody or antigen-binding fragment thereof is selected from the group consisting of atezolizumab, durvalumab (MEDI4736), BMS-936559, MSB0010718C and rHigM12B7. In some aspects, the antibody or antigen-binding fragment thereof that specifically binds to human PILRA and the antagonist of the inhibitory immune checkpoint molecule are administered simultaneously. In some aspects, the antibody or antigen-binding fragment thereof that specifically binds to human PILRA and the antagonist of the inhibitory immune checkpoint molecule are administered sequentially.

In some aspects, a method of treating a disease or condition in which myeloid cells are dysfunctional or deficient in a patient comprises administering to the patient a therapeutically effective amount of an antibody or antigen-binding fragment thereof provided herein or a pharmaceutical composition provided herein. In some aspects, the disease or condition is a neurodegenerative disease. In some aspects, the neurodegenerative disease is Alzheimer's disease. In some aspects, the patient carries the G78 variant of PILRA.

In some aspects, a method of activating the innate immune system in a patient comprises administering to the patient an effective amount of an antibody or antigen-binding fragment thereof provided herein or a pharmaceutical composition provided herein.

In some aspects, a method for detecting PILRA in a sample comprises contacting the sample with an antibody or antigen-binding fragment thereof provided herein or a pharmaceutical composition provided herein. In some aspects, the sample is obtained from a human subject. In some aspects, the sample is a cancer sample.

4. BRIEF DESCRIPTION OF THE FIGURES

Figure 13:
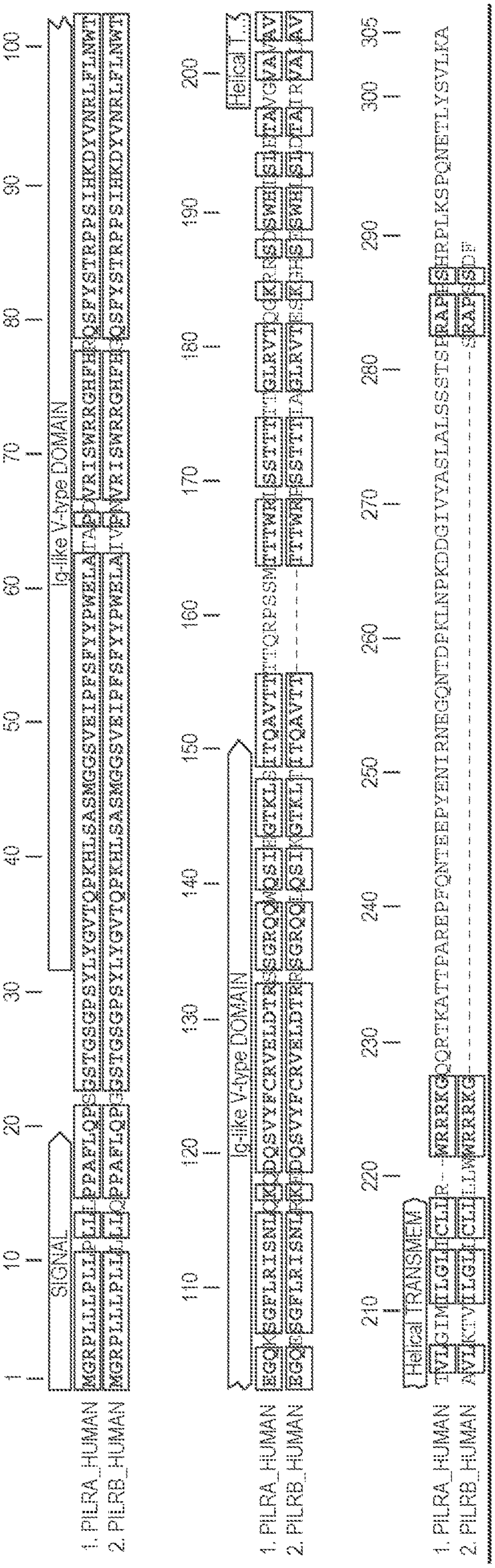

FIG. 13 provides an alignment of the human PILRA (SEQ ID NO:1) and human PILRB (SEQ ID NO:68) protein sequences.

Figure 14A:
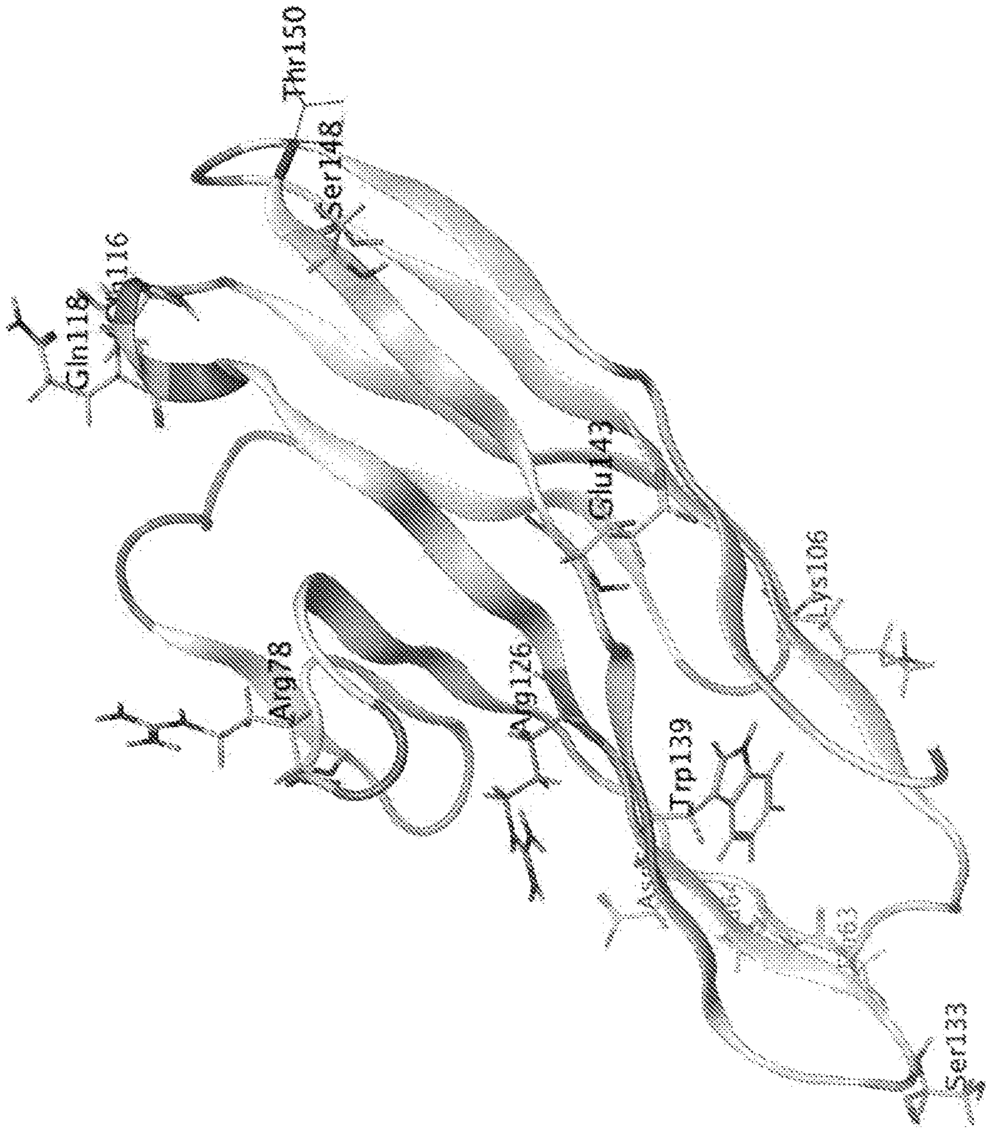
Figure 14B:
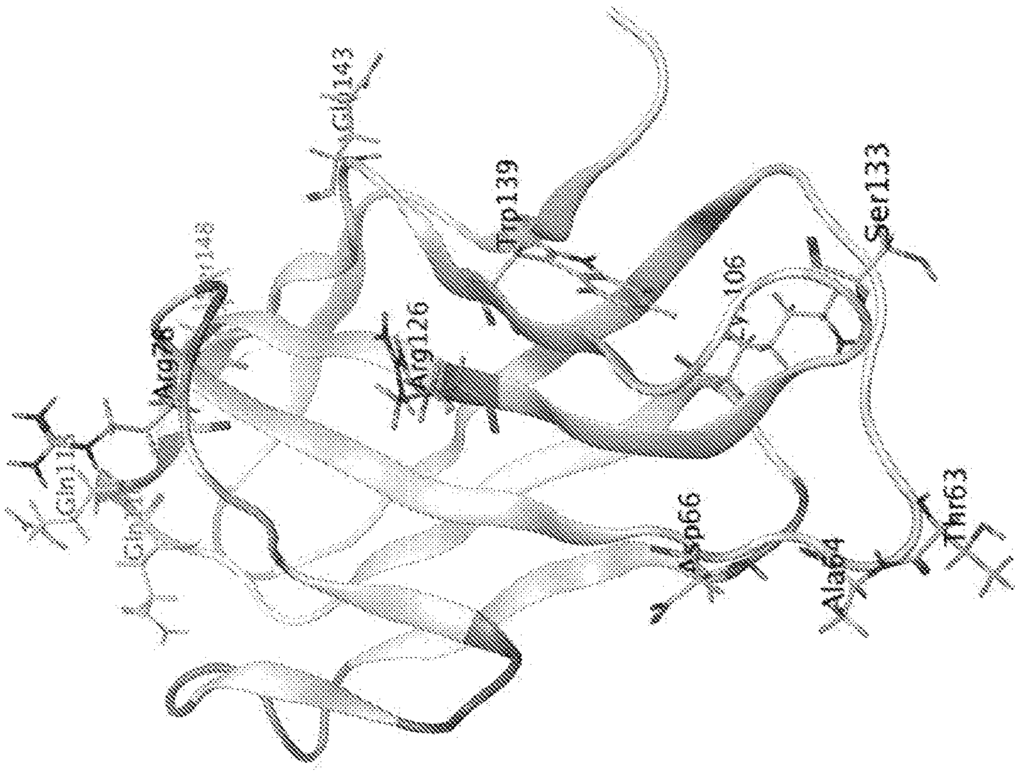

FIGS. 14A and 14B provide schematics of PILRA (amino acids 32-150 with Met added to the N-terminus) structure (based on Kuroki et al. PNAS 111: 877-8882 (2014); structure code 3WV0) with amino acids that differ from PILRB labeled.

5. DETAILED DESCRIPTION

Provided herein are antibodies (e.g., monoclonal antibodies) and antigen-binding fragments thereof that specifically bind to PILRA, e.g., human PILRA. Anti-human PILRA antibodies and antigen-binding fragments thereof can, for example, block binding of human PILRA to ligand and/or downregulate cell surface human PILRA. Exemplary anti-human PILRA antibodies are provided herein that demonstrate these activities. Blocking binding of human PILRA to ligand and/or downregulating cell surface human PILRA reduces inhibitory signaling by PILRA, resulting in activation and differentiation of myeloid cells. These activities may promote anti-tumor immunity and counteract the mechanisms of neurodegenerative diseases, such as Alzheimer's disease and other diseases associated with dysfunctional microglia.

Also provided are isolated nucleic acids (polynucleotides), such as complementary DNA (cDNA), encoding such antibodies and antigen-binding fragments thereof. Further provided are vectors (e.g., expression vectors) and cells (e.g., host cells) comprising nucleic acids (polynucleotides) encoding such antibodies and antigen-binding fragments thereof. Also provided are methods of making such antibodies and antigen-binding fragments thereof.

In other aspects, provided herein are methods for using such antibodies, for example, to modulate PILRA activity. PILRA activity can be modulated, for example, by altering the binding of PILRA to one or more of its ligands. In some aspects, anti-human PILRA antibodies provided herein are used to block the binding of human PILRA to ligand and/or to downregulate cell surface human PILRA.

In further aspects, anti-human PILRA antibodies provided herein are used to activate myeloid cells, such as macrophages, monocytes, dendritic cells, neutrophils, and microglia, in vitro or in vivo. In further aspects, anti-human PILRA antibodies provided herein are used to treat diseases in which myeloid cells are dysfunctional or deficient, e.g., diseases in which myeloid cell activation, myeloid cell differentiation, or activation of the innate immune system is desired. In some aspects, such diseases include, but are not limited to cancer and neurodegenerative diseases such as Alzheimer's disease. In particular, the R78 variant of PILRA, which is reported to reduce binding of PILRA to several of its ligands, is associated with reduced risk of Alzheimer's disease. Therefore, in some aspects, anti-human PILRA antibodies that reduce PILRA function (e.g., by blocking the binding of PILRA to ligand and/or downregulating cell surface human PILRA) would be useful for treating Alzheimer's disease. Related compositions (e.g., pharmaceutical compositions), kits, and methods are also provided.

5.1 Terminology

As used herein, the term "PILRA" refers to mammalian PILRA polypeptides including, but not limited to, native PILRA polypeptides and isoforms of PILRA polypeptides. "PILRA" encompasses full-length, unprocessed PILRA polypeptides as well as forms of PILRA polypeptides that result from processing within the cell. As used herein, the term "human PILRA" refers to a polypeptide comprising the amino acid sequence of SEQ ID NO:1; naturally occurring variants of SEQ ID NO:1, including but not limited to variants thereof in which either G or R is present at position 78 of SEQ ID NO:1; and processed forms of SEQ ID NO:1, including but not limited to SEQ ID NO:1 lacking its signal peptide, e.g., from amino acids 1-19 of SEQ ID NO:1. A "PILRA polynucleotide," "PILRA nucleotide," or "PILRA nucleic acid" refers to a polynucleotide encoding any PILRA, including those described above.

The term "antibody" means an immunoglobulin molecule that recognizes and specifically binds to a target, such as a protein, polypeptide, peptide, carbohydrate, polynucleotide, lipid, or combinations of the foregoing (e.g., a glycoprotein), through at least one antigen recognition site within the variable region of the immunoglobulin molecule. As used herein, the term "antibody" encompasses polyclonal antibodies, monoclonal antibodies, chimeric antibodies, humanized antibodies, human antibodies, and any other immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked, part of a fusion protein, or conjugated to other molecules such as toxins, radioisotopes, etc.

The term "antibody fragment" refers to a portion of an antibody. An "antigen-binding fragment," "antigen-binding domain," or "antigen-binding region," refers to a portion of an antibody that binds to an antigen. An antigen-binding fragment can contain the antigenic determining regions of an antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-PILRA antibody," "PILRA antibody" and "antibody that binds to PILRA" refer to an antibody that is capable of binding PILRA with sufficient affinity such that the antibody is useful as a diagnostic, a therapeutic, and/or as a modulator of PILRA activity. The extent of binding of an anti-PILRA antibody to an unrelated, non-PILRA protein can be less than about 10% of the binding of the antibody to PILRA as measured, e.g., by a radioimmunoassay (RIA). An anti-PILRA antibody can bind exclusively to PILRA and not to PILRB, or an anti-PILRA antibody can bind to PILRA and to PILRB.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, a "monoclonal" antibody or antigen-binding fragment thereof refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In some aspects, the variable region is a human variable region. In some aspects, the variable region comprises rodent or murine CDRs and human framework regions (FRs). In some aspects, the variable region is a primate (e.g., non-human primate) variable region. In some aspects, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In some aspects, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

As used herein, the term "constant region" or "constant domain" are interchangeable and have the meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In some aspects, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In some aspects, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementarity determining regions (CDRs) are replaced by residues from the CDRs of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). The humanized antibody or antigen-binding fragment thereof can be further modified by the substitution of additional residues either in the Fv framework region and/or within the replaced non-human residues to refine and optimize the specificity, affinity, and/or capability of the antibody or antigen-binding fragment thereof. In general, the humanized antibody or antigen-binding fragment thereof will comprise VH and VL that comprise substantially all of at least one, and typically two or three, of the CDR regions that correspond to the non-human immunoglobulin, whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some aspects, a "humanized antibody" is a resurfaced antibody.

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation rate constant of, e.g., an antibody or antigen-binding fragment thereof from an antigen. The $k_{on}$ and $k_{off}$ can be determined by techniques known to one of ordinary skill in the art, such as BIAcore© or KinExA.

A antibody that is "blocking" or that "blocks" or that is "inhibitory" of that "inhibits" is an antibody that reduces or inhibits (partially or completely) binding of its target protein to one or more ligands when the antibody is bound to the target protein, and/or that reduces or inhibits (partially or completely) one or more activities or functions of the target protein when the antibody is bound to the target protein.

An antibody that "downregulates" its target protein reduces expression of the target protein on the cell surface.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some aspects, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., alanine scanning or other site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Crystals of an antibody or antigen-binding fragment thereof and its antigen can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

A PILRA antibody that "binds to the same epitope" as a reference PILRA antibody refers to an antibody that contacts the same PILRA amino acid residues as the reference PILRA antibody. The ability of a PILRA antibody to bind to the same epitope as a reference PILRA antibody is determined using peptide scanning mutagenesis or high throughput alanine scanning mutagenesis (see Davidson and Doranz, 2014 Immunology 143, 13-20). In the latter methodology, a comprehensive mutation library of PILRA, or a portion thereof (e.g., the extracellular domain), can be generated by mutating each individual amino acid residue to alanine (or if the amino acid residue is alanine, then to another residue such as serine) and testing each mutant for binding to an anti-PILRA antibody or antigen binding fragment thereof. Amino acids that are required for binding, and therefore are epitope residues, are identified by loss of immunoreactivity.

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails complementarity between the antigen binding domain and the epitope. Accordingly, an antibody that "specifically binds" to human PILRA (e.g., SEQ ID NO:1) may also bind to PILRA from other species (e.g., cynomolgus monkey PILRA) and/or PILRA proteins produced from other human alleles, but the extent of binding to an un-related, non-PILRA protein (e.g., other immunomodulatory proteins containing ITIM domains) is less than about 10% of the binding of the antibody to PILRA as measured, e.g., by a radioimmunoassay (RIA).

An antibody is said to "competitively inhibit" binding of a reference antibody to a given epitope if it preferentially binds to that epitope or an overlapping epitope such that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in some aspects, the polypeptides can occur as single chains or associated chains.

As used herein, the term "host cell" can be any type of cell, e.g., a primary cell, a cell in culture, or a cell from a cell line. In some aspects, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer," "administering," "administration," and the like, as used herein, refer to methods that may be used to deliver a drug, e.g., an anti-human PILRA antibody or antigen-binding fragment thereof, to the desired site of biological action. Administration techniques that can be employed with the agents and methods described herein are found in e.g., Goodman and Gilman, *The Pharmacological Basis of Therapeutics*, current edition, Pergamon; and Remington's, Pharmaceutical Sciences, current edition, Mack Publishing Co., Easton, Pa.

As used herein, the terms "subject" and "patient" are used interchangeably. The subject can be a mammal such as a non-human animal (e.g., cow, pig, horse, cat, dog, rat, mouse, monkey or other primate, etc.). In some aspects, the subject is a cynomolgus monkey. In some aspects, the subject is a human.

The term "therapeutically effective amount" refers to an amount of a drug, e.g., an anti-human PILRA antibody or antigen-binding fragment thereof, effective to treat a disease or condition in a subject. In the case of cancer, the therapeutically effective amount of the drug can reduce the number of cancer cells; reduce the tumor size or burden; inhibit (i.e., slow to some extent and in some aspects, stop) cancer cell infiltration into peripheral organs; inhibit (i.e., slow to some extent and in some aspects, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. To the extent the drug can prevent growth and/or kill existing cancer cells, it can be cytostatic and/or cytotoxic.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In some aspects, a subject is successfully "treated" for cancer according to the methods provided herein if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

The terms "cancer" and "cancerous" refer to or describe the physiological condition in mammals in which a population of cells are characterized by unregulated cell growth. Such cancers can include solid tumors, e.g., solid tumors in which myeloid cells (monocytes, macrophages, dendritic cells, granulocytes, neutrophils, microglia or other innate immune cells) have infiltrated the tumor microenvironment. Examples of such cancers include, but are not limited to, glioblastoma, head and neck cancer, kidney cancer (e.g., kidney clear cell cancer), pancreatic cancer, and breast cancer. The cancer can be a "PILRA-positive cancer." This term refers to a cancer comprising cells (e.g., myeloid cells that have infiltrated the cancer) that express PILRA mRNA or protein. The cancer can be a cancer with "increased PILRA" mRNA or protein This refers to a cancer that has more PILRA (e.g., on myeloid cells that have infiltrated the cancer) than a healthy version of the same tissue.

As used in the present disclosure and claims, the singular forms "a," "an," and "the" include plural forms unless the context clearly dictates otherwise.

It is understood that wherever aspects are described herein with the language "comprising," otherwise analogous aspects described in terms of "consisting of" and/or "consisting essentially of" are also provided. In this disclosure, "comprises," "comprising," "containing" and "having" and the like can mean "includes," "including," and the like; "consisting essentially of" or "consists essentially of" are open-ended, allowing for the presence of more than that which is recited so long as basic or novel characteristics of that which is recited is not changed by the presence of more than that which is recited, but excludes prior art aspects.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of up to 10% above and down to 10% below the value or range remain within the intended meaning of the recited value or range. It is understood that wherever aspects are described herein with the language "about" or "approximately" a numeric value or range, otherwise analogous aspects referring to the specific numeric value or range are also provided.

Any compositions or methods provided herein can be combined with one or more of any of the other compositions and methods provided herein.

5.2 Antibodies

In one aspect, provided herein are antibodies (e.g., monoclonal antibodies, such as chimeric, humanized, or human antibodies) and antigen-binding fragments thereof which specifically bind to PILRA, such as human, murine or cynomolgus monkey PILRA. In a specific aspect, provided herein are antibodies (e.g., monoclonal antibodies, such as chimeric, humanized, or human antibodies) and antigen-binding fragments thereof which specifically bind to human PILRA. The amino acid sequences of human, cynomolgus monkey, and murine PILRA are known in the art and also provided herein as represented by SEQ ID NOs:1-3 respectively.

```
Human PILRA:
                                          (SEQ ID NO: 1)
MGRPLLLPLLPLLLPPAFLQPSGSTGSGPSYLYGVTQPKHLSASMGGSVE

IPFSFYYPWELATAPDVRISWRRGHFHRQSFYSTRPPSIHKDYVNRLFLN

WTEGQKSGFLRISNLQKQDQSVYFCRVELDTRSSGRQQWQSIEGTKLSIT

QAVTTTTQRPSSMTTTWRLSSTTTTTGLRVTQGKRRSDSWHISLETAVGV

AVAVTVLGIMILGLICLLRWRRRKGQQRTKATTPAREPFQNTEEPYENIR

NEGQNTDPKLNPKDDGIVYASLALSSSTSPRAPPSHRPLKSPQNETLYSV

LKA
```

In some aspects it is contemplated that the above human PILRA sequence lacks its signal sequence. For example, a human PILRA sequence can comprise amino acids 20-303 of SEQ ID NO:1. The above human PILRA sequence (SEQ ID NO:1) represents a variant sequence in which arginine (R) is present at position 78, and is encoded by an allele associated with protection from Alzheimer's disease. In some aspects, a variant PILRA sequence is contemplated in which position 78 is occupied by a glycine (G). Other features of human PILRA, as shown in SEQ ID NO:1, include an extracellular domain (ECD) from about amino acid 20-197, with an IgV domain from about amino acid 32-150, and ITIM motifs from about amino acid 267-272 and 296-301.

```
Cynomolgus monkey PILRA:
                                          (SEQ ID NO: 2)
MGRPLLLPLLLPLLPLLLPPAFLQPGGSAGSGPSGPYGVTQRKHLSAPMG

GSVEIPFSFYHPWELAAAPNMKISWRRGNFHGEFFYRTRPAFIHEDYSNR

LLLNWTEGQDRGLLRIWNLRKEDQSVYFCRVELDTRRSGRQRWQSIEGTK

LTITQAVTTTTQRPSSMTTTRRPSSATTTAGLRVTQGKRHSDSWHLSLKT

AVGVTVAVAVLGIMILGLICLLRWRRRKGQQRTKATTPAKEPFQNTEEPY

ENIRNEGQNTDPKPNPKDDGIVYASLALSSSTSPRVPPSHHPLKSPQNET

LYSVLKV
```

In some aspects it is contemplated that the above cynomolgus monkey PILRA sequence lacks its signal sequence. For example, a cynomolgus monkey PILRA sequence can comprise amino acids 24-307 of SEQ ID NO:2.

```
Murine PILRA
                                          (SEQ ID NO: 3)
MALLISLPGGTPAMAQILLLLSSACLHAGNSERSNRKNGFGVNQPESCSG

VQGGSIDIPFSFYFPWKLAKDPQMSIAWRWKDFHGEFIYNSSLPFIHEHF

KGRLILNWTQGQTSGVLRILNLKESDQTRYFGRVFLQTTEGIQFWQSIPG

TQLNVTNATCTPTTLPSTTAATSAHTQNDITEVKSANIGGLDLQTTVGLA

TAAAVFLVGVLGLIVFLWWKRRRQGQKTKAEIPAREPLETSEKHESVGHE

GQCMDPKENPKDNNIVYASISLSSPTSPGTAPNLPVHGNPQEETVYSIVK

AK
```

In some aspects it is contemplated that the above murine PILRA sequence lacks its signal sequence. For example, a murine PILRA sequence can comprise amino acids 32-302 of SEQ ID NO:3.

In some aspects, an antibody or antigen-binding fragment thereof described herein binds to human PILRA (e.g., SEQ ID NO:1 or amino acids 20-303 of SEQ ID NO: 1, or either of the foregoing sequences in which R or G is at position 78). In some aspects, an antibody or antigen-binding fragment thereof binds to human PILRA and cynomolgus monkey PILRA (e.g., SEQ ID NO:2 or amino acids 24-307 of SEQ ID NO:2). In some aspects, an antibody or antigen-binding fragment thereof binds to human PILRA but does not bind to cynomolgus monkey PILRA (e.g., SEQ ID NO:2 or amino acids 24-307 of SEQ ID NO:2). In some aspects, an antibody or antigen-binding fragment thereof binds to human PILRA but does not bind to murine PILRA (e.g., SEQ ID NO:3 or amino acids 32-302 of SEQ ID NO:3). In some aspects, an antibody or antigen-binding fragment thereof binds to human PILRA (and optionally to cynomolgus monkey PILRA) and to human PILRB (e.g., SEQ ID NO:68, as shown below, or amino acids 20-227 of SEQ ID NO:68). In some aspects, an antibody or antigen-binding fragment thereof binds to human PILRA (and optionally to cynomolgus monkey PILRA), but does not bind human PILRB.

The sequence of human PILRB is provided below as SEQ ID NO:68.

(SEQ ID NO: 68)

MGRPLLLPLLLLLQPPAFLQPGGSTGSGPSYLYGVTQPKHLSASMGGSVE

IPFSFYYPWELAIVPNVRISWRRGHFHGQSFYSTRPPSIHKDYVNRLFLN

WTEGQESGFLRISNLRKEDQSVYFCRVELDTRRSGRQQLQSIKGTKLTIT

QAVTTTTTWRPSSTTTIAGLRVTESKGHSESWHLSLDTAIRVALAVAVLK

TVILGLLCLLLLWWRRRKGSRAPSSDF

In some aspects it is contemplated that the above human PILRB sequence lacks its signal sequence. For example, a human PILRB sequence can comprise amino acids 20-227 of SEQ ID NO:68. An alignment of the amino acid sequences of human PILRA and human PILRB is provided in FIG. 13. The following amino acids of PILRA differ from those in PILRB: P11 (in signal sequence), L14 (in signal sequence), S22 (in signal sequence), T63, A64, D66, R78, K106, Q116, Q118, S133, W139, E143, S148, T156-M163, L169, T175, T176, Q182, G183, R185, R186, D188, 1192, and E195.

In some aspects an antibody or antigen-binding fragment thereof described herein binds to the extracellular domain of human PILRA (amino acids 20-197 of SEQ TD NO: 1).

In some aspects, an antibody or antigen-binding fragment thereof described herein binds to human PILRA and comprises the six CDRs of an antibody listed in Tables 1 and 2 (i.e., the three VH CDRs of the antibody listed in Table 1 and the three VL CDRs of the same antibody listed in Table 2).

TABLE 1

| VH CDR Amino Acid Sequences [1] | | | |
|---|---|---|---|
| Antibody | VH CDR1 (SEQ ID NO:) | VH CDR2 (SEQ ID NO:) | VH CDR3 (SEQ ID NO:) |
| hPA-002 | TFGMGVG (SEQ ID NO: 4) | HIWWDDDKYYNPALKS (SEQ ID NO: 5) | VEDYGNPFDY (SEQ ID NO: 6) |
| hPA-005 | TFGMGVG (SEQ ID NO: 10) | HIWWDDDKFYNPALKS (SEQ ID NO: 11) | IEDYGSYFAY (SEQ ID NO: 12) |
| hPA-004 | SFGVAVG (SEQ ID NO: 16) | HIWWDDDKSYNPALKS (SEQ ID NO: 17) | IADYGNHFDY (SEQ ID NO: 18) |
| hPA-001 | TFGMGVG (SEQ ID NO: 22) | HIWWDDDKYYNPALKS (SEQ ID NO: 23) | IEDYGNPFDY (SEQ ID NO: 24) |

[1] The VH CDRs in Table 1 are determined according to Kabat.

TABLE 2

| VL CDR Amino Acid Sequences [2] | | | |
|---|---|---|---|
| Antibody | VL CDR1 (SEQ ID NO:) | VL CDR2 (SEQ ID NO:) | VL CDR3 (SEQ ID NO:) |
| hPA-002 | HASQNIHVWLN (SEQ ID NO: 7) | KASNLHT (SEQ ID NO: 8) | QQGQSYPLT (SEQ ID NO: 9) |
| hPA-005 | HASQNIHVWLN (SEQ ID NO: 13) | KASNLHT (SEQ ID NO: 14) | QQGQSYPYT (SEQ ID NO: 15) |
| hPA-004 | HASQNSHVWLS (SEQ ID NO: 19) | KASNLHT (SEQ ID NO: 20) | QQGQTYPFT (SEQ ID NO: 21) |
| hPA-001 | HASQNIHVWLS (SEQ ID NO: 25) | KASNLHT (SEQ ID NO: 26) | QQGQSYPLT (SEQ ID NO: 27) |

[2] The VL CDRs in Table 2 are determined according to Kabat.

In some aspects, an antibody or antigen-binding fragment thereof described herein binds to human PILRA and comprises the VH of an antibody listed in Table 3.

TABLE 3

Variable Heavy Chain (VH) Amino Acid Sequences

| Antibody | VH Amino Acid Sequence (SEQ ID NO) |
|---|---|
| hPA-002 | QVTLQESGPGILQPSQTLSLTCSFSGFSLSTFGMGVGWIRQPSGKGLE WLAHIWWDDDKYYNPALKSRLTISKDTSKNQVFLKIASVDTADIATY YCARVEDYGNPFDYWGQGTTL (SEQ ID NO: 28) |
| hPA-005 | QVILKESGPGILQSSQTLSLTCSFSGFSLSTFGMGVGWIRQPSGKGLES LAHIWWDDDKFYNPALKSRLTISKDTSKSQVFLKIANVDTADIATYY CTRIEDYGSYFAYWGQGTTLTVSS (SEQ ID NO: 30) |
| hPA-004 | QVTLKESGPGMLQPSQTLSLACSFSGFSLNSFGVAVGWIRQPSGKGLE WLAHIWWDDDKSYNPALKSRLTISKDTSKNQVFLKLANVDTADTAT YYCTRIADYGNHFDYWGQGTALTVSS (SEQ ID NO: 32) |
| hPA-001 | QVTLKESGPGILQPSQTLSLTCSFSGFSLTTFGMGVGWIRQPSGKGLE WLAHIWWDDDKYYNPALKSRLTISKDISKNQVFLKIANVDTADTAT YYCARIEDYGNPFDYWGQGTTLTVSS (SEQ ID NO: 34) |

In some aspects, an antibody or antigen-binding fragment thereof described herein binds to human PILRA and comprises the VL of an antibody listed in Table 4.

TABLE 4

Variable Light Chain (VL) Amino Acid Sequences

| Antibody | VL Amino Acid Sequence (SEQ ID NO) |
|---|---|
| hPA-002 | DIQMNQSPSSLSASLGDTITITCHASQNIHVWLNWYQQKPGNIPKLLI YKASNLHTGVPSRFSGSGSGTGFTVTISSLQPEDIATYYCQQGQSYPL TFGAGTKLELK (SEQ ID NO: 29) |
| hPA-005 | DVQMNQSPSSLSASLGDPITITCHASQNIHVWLNWYQQRPGNIPRLLI YKASNLHTGVPSRFSGSGSGTGFTLTISSLQPEDIATYYCQQGQSYPY TFGGGTKLEIK (SEQ ID NO: 31) |
| hPA-004 | DIQMNQSPSSLSASLGDTITITCHASQNSHVWLSWYQQKPGNIPKLLI YKASNLHTGVPSRFSGSGSGTGFTLTISGLQPEDIATYYCQQGQTYPF TFGSGTKLEIK (SEQ ID NO: 33) |
| hPA-001 | DIQMNQSPSSLSASLGDTITITCHASQNIHVWLSWYQQKPGNIPKLLIY KASNLHTGVPSRFSGSGSGTGFTLTISSLQPEDIATYYCQQGQSYPLTF GAGTKLELK (SEQ ID NO: 35) |

In some aspects, an antibody or antigen-binding fragment thereof described herein binds to human PILRA and comprises the VH and the VL of an antibody listed in Tables 3 and 4 (i.e., the VH of the antibody listed in Table 3 and the VL of the same antibody listed in Table 4).

In some aspects, an antibody or antigen-binding fragment thereof described herein binds to human PILRA and comprises one, two, three or all of the VH framework regions of an antibody listed in Table 5.

TABLE 5

VH FR Amino Acid Sequences [3]

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| hPA-002 | QVTLQESGPGILQP SQTLSLTCSFSGFS LS (SEQ ID NO: 36) | WIRQPSGKGLE WLA (SEQ ID NO: 37) | RLTISKDTSKNQVFL KIASVDTADIATYY CAR (SEQ ID NO: 38) | WGQGTTLT VSS (SEQ ID NO: 39) |
| hPA-005 | QVILKESGPGILQS SQTLSLTCSFSGFS LS (SEQID NO: 44) | WIRQPSGKGLE SLA (SEQ ID NO: 45) | RLTISKDTSKSQVFL KIANVDTADIATYY CTR (SEQ ID NO: 46) | WGQGTTLT VSS (SEQ ID NO: 47) |
| hPA-004 | QVTLKESGPGMLQ PSQTLSLACSFSGF SLN (SEQ ID NO: 52) | WIRQPSGKGLE WLA (SEQ ID NO: 53) | RLTISKDTSKNQVFL KLANVDTADTATY YCTR (SEQ ID NO: 54) | WGQGTALT VSS (SEQ ID NO: 55) |

TABLE 5-continued

| VH FR Amino Acid Sequences [3] | | | | |
|---|---|---|---|---|
| Anti-body | VH FR1 (SEQ ID NO:) | VH FR2 (SEQ ID NO:) | VH FR3 (SEQ ID NO:) | VH FR4 (SEQ ID NO:) |
| hPA-001 | QVTLKESGPGILQP SQTLSLTCSFSGFS LT (SEQ ID NO: 60) | WIRQPSGKGLE WLA (SEQ ID NO: 61) | RLTISKDISKNQVFL KIANVDTADTATYY CAR (SEQ ID NO: 62) | WGQGTTLT VSS (SEQ ID NO: 63) |

[3] The VH framework regions described in Table 5 are determined based upon the boundaries of the Kabat numbering system for CDRs. In other words, the VH CDRs are determined by Kabat and the framework regions are the amino acid residues surrounding the CDRs in the a variable region in the format FR1, CDR1, FR2, CDR2, FR3, CDR3, and FR4.

In some aspects, an antibody or antigen-binding fragment thereof described herein binds to human PILRA and comprises one, two, three or all of the VL framework regions of an antibody listed in Table 6.

TABLE 6

| VL FR Amino Acid Sequences [4] | | | | |
|---|---|---|---|---|
| Anti-body | VL FR1 (SEQ ID NO:) | VL FR2 (SEQ ID NO:) | VL FR3 (SEQ ID NO:) | VL FR4 (SEQ ID NO:) |
| hPA-002 | DIQMNQSPSSLSAS LGDTITITC (SEQ ID NO: 40) | WYQQKPGNIP KLLIY (SEQ ID NO: 41) | GVPSRFSGSGSGT GFTVTISSLQPEDI ATYYC (SEQ ID NO: 42) | FGAGTKLEL K (SEQ ID NO: 43) |
| hPA-005 | DVQMNQSPSSLSA SLGDPITITC (SEQ ID NO: 48) | WYQQRPGNIPR LLIY (SEQ ID NO: 49) | GVPSRFSGSGSGT GFTLTISSLQPEDI ATYYC (SEQ ID NO: 50) | FGGGTKLEI K (SEQ ID NO: 51) |
| hPA-004 | DIQMNQSPSSLSAS LGDTITITC (SEQ ID NO: 56) | WYQQKPGNIP KLLIY (SEQ ID NO: 57) | GVPSRFSGSGSGT GFTLTISGLQPEDI ATYYC (SEQ ID NO: 58) | FGSGTKLEIK (SEQ ID NO: 59) |
| hPA-001 | DIQMNQSPSSLSAS LGDTITITC (SEQ ID NO: 64) | WYQQKPGNIP KLLIY (SEQ ID NO: 65) | GVPSRFSGSGSGT GFTLTISSLQPEDI ATYYC (SEQ ID NO: 66) | FGAGTKLEL K (SEQ ID NO: 67) |

[4] The VL framework regions described in Table 6 are determined based upon the boundaries of the Kabat numbering system for CDRs. In other words, the VL CDRs are determined by Kabat and the framework regions are the amino icid residues surrounding the CDRs in the variable region in the format FR1, CDR1, FR2, CDR2, FR3, CDR3, and FR4.

In some aspects, an antibody or antigen-binding fragment thereof described herein binds to human PILRA and comprises the four VH framework regions and the four VL framework regions of an antibody listed in Tables 5 and 6 (i.e., the four VH framework regions of the antibody listed in Table 5 and the four VL framework regions of the same antibody listed in Table 6.)

In certain aspects, an antibody or antigen-binding fragment thereof described herein may be described by its VL domain alone, or its VH domain alone, or by its 3 VL CDRs alone, or its 3 VH CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antibodies and antigen-binding fragments thereof that specifically bind to human PILRA and comprise the Chothia VH and VL CDRs of an antibody listed in Tables 3 and 4. In some aspects, antibodies or antigen-binding fragments thereof that specifically bind to human PILRA comprise one or more CDRs, in which the Chothia and Kabat CDRs have the same amino acid sequence. In some aspects, provided herein are antibodies and antigen-binding fragments thereof that specifically bind to human PILRA and comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In some aspects, provided herein are antibodies and antigen-binding fragments thereof that specifically bind to human PILRA and comprise the IMGT VH and VL CDRs of an antibody listed in Tables 3 and 4, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in Antibody Engineering, Kontermann and Dubel, eds., Chapter 31, pp. 422-439, Springer-Verlag, Berlin (2001). In some aspects, provided herein are antibodies or antigen-binding fragments thereof that specifically bind to human PILRA and comprise VH and VL CDRs of an antibody listed in Tables 3 and 4 as determined by the method in MacCallum R M et al.

In certain aspects, the CDRs of an antibody or antigen-binding fragment thereof can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.). In some aspects, provided herein are antibodies or antigen-binding fragments thereof that specifically bind to human PILRA and comprise VH and VL CDRs of an antibody listed in Tables 3 and 4 as determined by the AbM numbering scheme.

In some aspects, provided herein are antibodies that comprise a heavy chain and a light chain. With respect to the heavy chain, in some aspects, the heavy chain of an antibody described herein can be an alpha (α), delta (δ), epsilon (ε), gamma (γ) or mu (μ) heavy chain. In some aspects, the heavy chain of an antibody described can comprise a human alpha (α), delta (δ), epsilon (ε), gamma (γ) or mu (μ) heavy chain. In some aspects, an antibody described herein, which immunospecifically binds to human PILRA, comprises a heavy chain wherein the amino acid sequence of the VH domain comprises an amino acid sequence set forth in Table 3 and wherein the constant region of the heavy chain comprises the amino acid sequence of a human gamma (γ) heavy chain constant region. In some aspects, an antibody described herein, which immunospecifically binds to human PILRA, comprises a heavy chain wherein the amino acid sequence of the VH domain comprises an amino acid sequence set forth in Table 3 and wherein the constant region of the heavy chain comprises the amino acid sequence of an IgG1 heavy chain constant region. In some aspects, an antibody described herein, which immunospecifically binds to human PILRA, comprises a heavy chain wherein the amino acid sequence of the VH domain comprises an amino acid sequence set forth in Table 3 and wherein the constant region of the heavy chain comprises the amino acid sequence of an IgG2 (e.g., IgG2a or IgG2b) heavy chain constant region. In some aspects, an antibody described herein, which immunospecifically binds to human PILRA, comprises a heavy chain wherein the amino acid sequence of the VH domain comprises an amino acid sequence set forth in Table 3 and wherein the constant region of the heavy chain comprises the amino acid sequence of an IgG4 heavy chain constant region. In some aspects, an antibody described herein, which immunospecifically binds to human PILRA, comprises a heavy chain wherein the amino acid sequence of the VH domain comprises a sequence set forth in Table 3, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

With respect to the light chain, in some aspects, the light chain of an antibody described herein is a kappa light chain. In some aspects, the light chain of an antibody described herein is a lambda light chain. In some aspects, the light chain of an antibody described herein is a human kappa light chain or a human lambda light chain.

In some aspects, an antibody described herein, which immunospecifically binds to a human PILRA, comprises a light chain wherein the amino acid sequence of the VL domain comprises a sequence set forth in Table 4, and wherein the constant region of the light chain comprises the amino acid sequence of a human kappa light chain constant region. In some aspects, an antibody described herein, which immunospecifically binds to human PILRA, comprises a light chain wherein the amino acid sequence of the VL domain comprises a sequence set forth in Table 4, and wherein the constant region of the light chain comprises the amino acid sequence of a human lambda light chain constant region. In some aspects, an antibody described herein, which immunospecifically binds to human PILRA, comprises a light chain wherein the amino acid sequence of the VL domain comprises a sequence set forth in Table 4, and wherein the constant region of the light chain comprises the amino acid sequence of a human kappa or lambda light chain constant region. Non-limiting examples of human constant region sequences have been described in the art, e.g., see U.S. Pat. No. 5,693,780 and Kabat E A et al., (1991) supra.

In some aspects, an antibody described herein, which immunospecifically binds to human PILRA comprises a VH domain and a VL domain comprising the amino acid sequence of any of the anti-human PILRA antibodies described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In some aspects, an antibody described herein, which immunospecifically binds to human PILRA comprises a VH domain and a VL domain comprising the amino acid sequences of any of the anti-human PILRA antibodies described herein, and wherein the constant regions comprise the amino acid sequences of the constant regions of an IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule. In some aspects, the constant regions comprise the amino acid sequences of the constant regions of a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule.

Non-limiting examples of human constant regions are described in the art, e.g., see Kabat E A et al., (1991) supra.

Exemplary Fc Domains

In some aspects, an anti-PILRA antibody, and in particular, an anti-human PILRA antibody as provided herein, may comprise an Fc domain. In some aspects, the Fc domain is a human IgG1, IgG2, IgG3, and/or IgG4 isotype.

In certain aspects, the Fc domain has an IgG1 isotype. In some aspects, an anti-PILRA antibody contains a murine IgG1 Fc domain. In some aspects, an anti-human PILRA antibody contains a human IgG1 Fc domain (hIgG1), e.g., as provided in SEQ ID NO:69.

```
                                           (SEQ ID NO: 69)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPG
```

In some aspects, the human IgG1 Fe domain of an anti-human PILRA antibody binds an activating Fc receptor. In certain aspects, the activating Fc receptor is selected from any one or more of FcγRI, FcγRIIa and IIc, and FcγRIIIa and IIIb.

In some aspects, the human IgG1 Fc domain of an anti-human PILRA antibody does not bind or has reduced binding to FcγRIII(CD16) and/or C1q. In some aspects, the human IgG1 Fc domain of an anti-human PILRA antibody has reduced antibody-dependent cellular cytotoxicity (ADCC) and/or complement binding activity, respectively, which in each case may reduce undesired killing of cells, e.g., myeloid cells, to which the anti-PILRA antibody binds. The above effects may be achieved by certain amino acid modifications, e.g., the "NSLF" mutations, in which a human IgG1 Fc domain contains the mutations N325S and L328F (by EU numbering of the IgG1 Fc domain), as shown, e.g., in SEQ ID NO:70. In another aspect, the human IgG1 Fc domain comprises a mutation corresponding to K322A (EU numbering), e.g., as provided in SEQ ID NO:71.

```
                                           (SEQ ID NO: 70)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN
```

-continued

```
GKEYKCKVSSKAFPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

                                           (SEQ ID NO: 71)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCAVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

Exemplary modifications to the human IgG1 Fc domain are listed below in Table 7.

TABLE 7

| Exemplary modifications to the human IgG1 Fc domain<br>Mutation (EU numbering scheme) |
|---|
| N325S and L328F ("NSLF") |
| S267E and L328F ("SELF") |
| P331S ("PS") |
| P331S and E430G ("PSEG") |
| K322A |
| L234A, L235A, and P331S ("LALAPS") (Substantially abolishes Fc binding to FcR) |

In certain aspects of an anti-PILRA antibody provided herein, the Fe domain has an IgG2 isotype. In some aspects, an anti-PILRA antibody contains a murine IgG2 Fc domain, e.g., murine IgG2a (mIgG2a). In some aspects, an anti-human PILRA antibody contains a human IgG2 Fc domain (hIgG2). In some aspects, the human IgG2 Fc domain of an anti-human PILRA antibody binds an activating Fc receptor. In certain aspects, the activating Fc receptor is selected from any one or more of FcγRI, FcγRIIa and IIc, and FcγRIIIa and IIIb.

In certain aspects of an anti-PILRA antibody provided herein, the Fc domain has an IgG4 isotype. In some aspects, an anti-human PILRA antibody contains a human IgG4 Fc domain (hIgG4), e.g., as provided in SEQ ID NO:72. In some aspects, the human IgG4 Fc region of the anti-human PILRA antibody binds an activating Fc receptor. In certain aspects, the activating Fc receptor is selected from any one or more of FcγRI, FcγRIIa and IIc, and FcγRIIIa and IIIb. In certain aspects, the human IgG4 Fc region comprises a mutation corresponding to S228P (by EU numbering), e.g., as provided in SEQ ID NO:73.

```
                                           (SEQ ID NO: 72)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

                                           (SEQ ID NO: 73)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL
```

-continued

VKGFYPSDIAVEWESNGQPENNYKTTPPVLDSDGSFFLYSRLTVDKSRWQ

EGNVFSCSVMHEALHNHYTQKSLSLSLGK

In some aspects, any of the constant region mutations or modifications described herein can be introduced into one or both heavy chain constant regions of an antibody or antigen-binding fragment thereof described herein having two heavy chain constant regions.

In some aspects, an antibody or antigen-binding fragment thereof described herein, which immunospecifically binds to human PILRA, comprises a heavy chain and a light chain, wherein (i) the heavy chain comprises a VH domain comprising the VH CDR1, VH CDR2, and VH CDR3 amino acid sequences of an antibody listed in Table 1 (e.g., SEQ ID NOs:4-6, 10-12, 16-18, or 22-24); (ii) the light chain comprises a VL domain comprising the VL CDR1, VL CDR2, and VL CDR3 amino acid sequences of the same antibody listed in Table 2 (e.g., SEQ ID NOs:7-9, 13-15, 19-21, or 25-27); (iii) the heavy chain further comprises a constant heavy chain domain comprising the amino acid sequence of the constant domain of a human IgG1 heavy chain; and (iv) the light chain further comprises a constant light chain domain comprising the amino acid sequence of the constant domain of a human kappa light chain.

In some aspects, an antibody or antigen-binding fragment thereof described herein, which immunospecifically binds to human PILRA, comprises a heavy chain and a light chain, wherein (i) the heavy chain comprises a VH domain comprising the amino acid sequence of an antibody listed in Table 3 (e.g., SEQ ID NO:28, 30, 32, or 34); (ii) the light chain comprises a VL domain comprising the amino acid sequence of the same antibody listed in Table 4 (e.g., SEQ ID NO:29, 31, 33, or 35); (iii) the heavy chain further comprises a constant heavy chain domain comprising the amino acid sequence of the constant domain of a human IgG1 heavy chain; and (iv) the light chain further comprises a constant light chain domain comprising the amino acid sequence of the constant domain of a human kappa light chain.

In some aspects, an antibody or antigen-binding fragment thereof described herein, which immunospecifically binds to human PILRA, comprises framework regions (e.g., framework regions of the VH domain and/or VL domain) that are human framework regions or derived from human framework regions. Non-limiting examples of human framework regions are described in the art, e.g., see Kabat E A et al., (1991) supra). In some aspects, an antibody or antigen-binding fragment thereof described herein comprises framework regions (e.g., framework regions of the VH domain and/or VL domain) that are primate (e.g., non-human primate) framework regions or derived from primate (e.g., non-human primate) framework regions.

In some aspects, an antibody or antigen-binding fragment thereof described herein, which immunospecifically binds to human PILRA, comprises one, two, three or four VH framework regions (FRs) having the amino acid sequences described herein for an antibody set forth in Table 5, supra (e.g., SEQ ID NOs:36-39, 44-47, 52-55, or 60-63). In some aspects, an antibody or antigen-binding fragment thereof described herein, which immunospecifically binds to human PILRA, comprises one, two, three or four VL framework regions (FRs) having the amino acid sequences described herein for an antibody set forth in Table 6, supra (e.g., SEQ ID NOs:40-43, 48-51, 56-59, or 64-67). In some aspects, an antibody or antigen-binding fragment thereof described herein, which immunospecifically binds to human PILRA, comprises one, two, three or four VH framework regions having the amino acid sequences described herein for an antibody set forth in Table 5, supra, and one, two, three or four VL framework regions having the amino acid sequences described herein for the same antibody set forth in Table 6, supra (e.g., (i) SEQ ID NOs:36-39, 44-47, 52-55, or 60-63 and (ii) SEQ ID NOs40-43, 48-51, 56-59, or 64-67).

Antibody Activities

In some aspects, an antibody or antigen-binding fragment thereof described herein, which immunospecifically binds to human PILRA, downregulates cell-surface PILRA. An anti-human PILRA antibody that downregulates PILRA would have the effect of decreasing inhibitory signaling that would otherwise result from engagement of cell surface PILRA with its ligand.

In some aspects, an antibody or antigen-binding fragment thereof described herein, which immunospecifically binds to human PILRA, downregulates cell-surface PILRA (e.g., human PILRA that is ectopically expressed on 293 cells), as compared to the level of cell-surface PILRA in the absence of the antibody or fragment or in the presence of a control antibody or fragment. In some aspects, cell-surface PILRA is downregulated by at least 10%, at least 20%, at least 30%, at least 40%, or at least 50% in the presence of the anti-human PILRA antibody after 30 minutes at 37° C., as compared to the level of cell surface PILRA in the absence of the antibody or fragment or in the presence of a control antibody or fragment after 30 minutes at 37° C. In some aspects, cell-surface PILRA is downregulated by about 10% to about 50% in the presence of the anti-human PILRA antibody after 30 minutes at 37° C., as compared to cell surface PILRA in the absence of the antibody or fragment or in the presence of a control antibody or fragment after 30 minutes at 37° C. In some aspects, cell surface PILRA is downregulated by at least 30%, at least 40%, at least 50%, or at least 60% in the presence of the anti-human PILRA antibody after 2 hours at 37° C., e.g., as compared to the level of cell surface PILRA in the absence of the antibody or fragment or in the presence of a control antibody or fragment after 2 hours at 37° C. In some aspects, cell-surface PILRA is downregulated by about 30% to about 60% in the presence of the anti-human PILRA antibody after 2 hours at 37° C., e.g., as compared to the level of cell surface PILRA in the absence of the antibody or fragment or in the presence of a control antibody or fragment after 2 hours at 37° C. The percent downregulation can be calculated, for example, by normalizing the levels of cell surface PILRA detected after incubation at the indicated time points on ice versus 37° C., in the presence or absence of anti-human PILRA antibody, or in the presence of anti-human PILRA antibody or a control antibody.

Downregulation can be measured, for example, using the assay disclosed in Example 8. Downregulation can be measured, for example, by incubating sialidase-treated 293 cells ectopically expressing human PILRA with anti-human PILRA antibody or with no antibody or control antibody (e.g., for 30 minutes at 37° C.) and detecting cell surface human PILRA. Cell surface human PILRA can be detected, for example, using FACS. The downregulation can be dependent on the dose of anti-human PILRA antibody.

In some aspects, an antibody or antigen-binding fragment thereof described herein, which immunospecifically binds to human PILRA, blocks binding of PILRA-Fc to human T-cells. An anti-human PILRA antibody that binds to PILRA-Fc and blocks binding of PILRA-Fc to T-cells is presumed to be blocking binding of PILRA-Fc to a PILRA ligand on T-cells. An antibody with this activity would likewise be expected to function in blocking the binding of endogenous PILRA to a PILRA ligand, thereby suppressing the inhibitory signaling of endogenous PILRA.

In some aspects, an antibody or antigen-binding fragment thereof described herein, which immunospecifically binds to human PILRA, blocks binding of PILRA-Fc to human T-cells by at least 70%, e.g., as compared to the binding of PILRA-Fc to human T-cells in the absence of the antibody or fragment or in the presence of a control antibody or fragment. In some aspects, an antibody or antigen-binding fragment thereof described herein, which immunospecifically binds to human PILRA, blocks binding of PILRA-Fc to human T-cells by at least 75%, e.g., as compared to the binding of PILRA-Fc to human T-cells in the presence of a control antibody. In some aspects, an antibody or antigen-binding fragment thereof described herein, which immunospecifically binds to human PILRA, blocks binding of PILRA-Fc to human T-cells by at least 80%, e.g., as compared to the binding of PILRA-Fc to human T-cells in the absence of the antibody or fragment or in the presence of a control antibody or fragment. In some aspects, an antibody or antigen-binding fragment thereof described herein, which immunospecifically binds to human PILRA, blocks binding of PILRA-Fc to human T-cells by at least 85%, e.g., as compared to the binding of PILRA-Fc to human T-cells in the absence of the antibody or fragment or in the presence of a control antibody or fragment. In some aspects, an antibody or antigen-binding fragment thereof described herein, which immunospecifically binds to human PILRA, blocks binding of PILRA-Fc to human T-cells by at least 90%, e.g., as compared to the binding of PILRA-Fc to human T-cells in the absence of the antibody or fragment or in the presence of a control antibody or fragment. In some aspects, an antibody or antigen-binding fragment thereof described herein, which immunospecifically binds to human PILRA, blocks binding of PILRA-Fc to human T-cells by at least 95%, e.g., as compared to the binding of PILRA-Fc to human T-cells in the absence of the antibody or fragment or in the presence of a control antibody or fragment. In some aspects, an antibody or antigen-binding fragment thereof described herein, which immunospecifically binds to human PILRA, blocks binding of PILRA-Fc to human T-cells by 100%, e.g., as compared to the binding of PILRA-Fc to human T-cells in the absence of the antibody or fragment or in the presence of a control antibody or fragment. In some aspects, an antibody or antigen-binding fragment thereof described herein, which immunospecifically binds to human PILRA, blocks binding of PILRA-Fc to human T-cells by about 70% to about 95%, or by about 70% to about 98%, e.g., as compared to the binding of PILRA-Fc to the human T-cells in the presence of a control antibody or fragment. In some aspects, an antibody or antigen-binding fragment thereof described herein, which immunospecifically binds to human PILRA, blocks binding of PILRA-Fc to human T-cells by about 80% to about 95% e.g., as compared to the binding of PILRA-Fc to human T-cells in the presence of a control antibody or fragment.

Blocking of binding can be measured, for example, using the assay disclosed in Example 7. Blocking of binding can be measured, for example, by incubating an anti-human PILRA antibody or antigen-binding fragment thereof with about 5 μg/ml PILRA Fc for 30 min at 4° C., then adding human T cells for 30 min at 4° C., washing the cells and detecting bound PILRA Fc. The bound PILRA Fc can be detected, for example, using flow cytometry. The blocking of binding can be dependent on the dose of anti-human PILRA antibody.

In some aspects, an antibody or antigen-binding fragment thereof described herein, which immunospecifically binds to human PILRA, blocks binding of PILRA to one or more PILRA ligands. PILRA ligands include glycosylated proteins, such as those with PTPXP, PTPXXP, PXTPXP, or PXTPXXP motif Exemplary ligands include COLEC12, NPDC1, CLEC4G, and PIANP, as well as the HSV-1 glycoprotein B. Amino acid Arg126 in PILRA (SEQ ID NO:1), is well known to be essential for sialic acid interaction (see e.g., Rathore et al., PLOS Genetics 14: e1007427 (2018)), and amino acids Arg78, Trp139, and Glu143, which differ from the corresponding amino acids in PILRB (see FIG. 13), are located in proximity to Arg126 (about 9.17 Å, about 4.40 Å, and about 12.40 Å, respectively) (see FIGS. 14A and B). Additional amino acids that diverge between human PILRA and human PILRB that are in the crystal structure provided in FIGS. 14A and 14B are T63, A64, D66, K106, Q116, Q118, S133, and S148.

In some aspects, an anti-human PILRA antibody that blocks binding of PILRA to one or more of its ligands can be identified by testing the ability of the antibody to block binding of PILRA-Fc to one or more PILRA ligands, wherein such ligand is expressed in a soluble form or expressed on a cell surface. In some aspects, an anti-human PILRA antibody that blocks binding of PILRA to one or more of its ligands can be identified by testing the ability of the antibody to block binding of cells expressing cell surface PILRA to one or more PILRA ligands, wherein such ligand is expressed in a soluble form or expressed on a cell surface.

In some aspects, an antibody or antigen-binding fragment thereof described herein, which immunospecifically binds to human PILRA, blocks binding of PILRA-Fc to one or more PILRA ligands (including but not limited to those provided above), e.g., as compared to the binding in the absence of the antibody or fragment or in the presence of a control antibody or fragment. Blocking of binding can be measured, for example, using the assay disclosed in Example 5. Blocking of binding can be measured, for example, by incubating cells expressing PILRA (e.g., for about 30 min at about 4° C.), with about 5 μg/ml of the ligand, incubating again (e.g., for about 30 min at about 4° C.), washing the cells and detecting bound ligand. The bound ligand can be detected, for example, using flow cytometry. The blocking of binding can be dependent on the dose of anti-human PILRA antibody.

In some aspects, an antibody or antigen-binding fragment thereof described herein, which immunospecifically binds to human PILRA, activates myeloid cells (e.g., macrophages (such as "M1" macrophages), microglia, dendritic cells, neutrophils, granulocytes and other myeloid-derived cells such as myeloid-derived suppressor cells ("MDSCs")). By activating myeloid cells, an anti-human PILRA antibody is capable of activating the innate immune system, e.g., which can promote an anti-tumor response and, in the case of microglia, can promote an environment in the CNS that counteracts neurodegenerative conditions.

In some aspects, an antibody or antigen-binding fragment thereof described herein, which immunospecifically binds to human PILRA, activates myeloid cells (such as those described above), as compared to the activation of myeloid cells in the absence of the antibody or fragment or in the presence of a control antibody or fragment. The assay disclosed in Example 2 or 3 can be used to assess activation of myeloid cells (e.g., MDSCs). Activation of myeloid cells (e.g., MDSCs) can be assessed, for example, by detecting the amount of MIP1b produced by the cells in the presence of an anti-human PILRA antibody or antigen-binding fragment thereof compared to activation in the absence of the antibody or fragment or in the presence of a control antibody or fragment. The activation of the myeloid cells (e.g., MDSCs) can be dependent on the dose of anti-human PILRA antibody.

In some aspects, an antibody or antigen-binding fragment thereof described herein, which immunospecifically binds to human PILRA, promotes differentiation of myeloid cells (e.g., promotes differentiation of monocytes into macrophages (such as "M1" macrophages) or dendritic cells, or promotes differentiation of other myeloid precursors into microglia, dendritic cells, neutrophils and other myeloid-derived cells such as myeloid-derived suppressor cells ("MDSCs")). By promoting the differentiation of myeloid cells, an anti-human PILRA antibody is capable of activating the innate immune system, e.g., which can promote an anti-tumor response (e.g., through M1 macrophages in the tumor microenvironment) and, in the case of microglia, can promote an environment in the CNS that counteracts neurodegenerative conditions.

In some aspects, an antibody or antigen-binding fragment thereof described herein, which immunospecifically binds to human PILRA, promotes differentiation of myeloid cells (such as those described above), compared to the differentiation of the myeloid cells in the absence of the antibody or fragment or in the presence of a control antibody or fragment. The assay disclosed in Example 2 can be used to assess differentiation of myeloid cells (e.g., MDSCs). Differentiation of myeloid cells (e.g., MDSCs) can be assessed, for example, by detecting the amount of $CD14^{lo}$ $CD86^{hi}$ cells in the presence of an anti-human PILRA antibody or antigen-binding fragment thereof compared to differentiation in the absence of the antibody or fragment or in the presence of a control antibody or fragment. The differentiation of the myeloid cells (e.g., MDSCs) can be dependent on the dose of anti-human PILRA antibody.

Antibodies that Bind Same Epitope/Competitively Inhibit

In another aspect, provided herein are antibodies or antigen-binding fragments thereof that bind to the same epitope of human PILRA as an antibody or antigen-binding fragment thereof described herein (e.g., hPA-002, hPA-005, hPA-004, or hPA-001).

In another aspect, provided herein are antibodies or antigen-binding fragments thereof that bind to an overlapping epitope of human PILRA as an antibody or antigen-binding fragment thereof described herein (e.g., hPA-002, hPA-005, hPA-004, or hPA-001). Antibodies that have overlapping epitopes contact at least one or more of the same amino acid residues of PILRA.

Competitive binding assays can be used to determine whether two antibodies bind to overlapping epitopes. Competitive binding can be determined in an assay in which an immunoglobulin to be tested inhibits specific binding of a reference antibody to a common antigen, such as PILRA (e.g., human PILRA). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., PILRA such as human PILRA) bound to a solid surface or cells bearing such antigen, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In some aspects, a competitive binding assay is performed using surface plasmon resonance (BIAcore®), e.g., by an 'in tandem approach' such as that described by Abdiche Y N et al., (2009) Analytical Biochem 386: 172-180, whereby PILRA antigen is immobilized on the chip surface, for example, a CM5 sensor chip and the anti-PILRA antibodies are then run over the chip. To determine if an antibody or antigen-binding fragment thereof competitively inhibits binding of an anti-PILRA antibody described herein, the anti-PILRA antibody is first run over the chip surface to achieve saturation and then the potential, competing antibody is added. Binding of the competing antibody or antigen-binding fragment thereof can then be determined and quantified relative to a non-competing control.

In some aspects, a Fortebio Octet competitive binding is used to determine that a PILRA antibody or antigen-binding fragment thereof competitively inhibits the binding of another PILRA antibody or antigen-binding fragment thereof to PILRA.

In another aspect, provided herein are antibodies that competitively inhibit (e.g., in a dose dependent manner) an antibody or antigen-binding fragment thereof described herein (e.g., hPA-002, hPA-005, hPA-004, or hPA-001) from binding to human PILRA, as determined using assays known to one of skill in the art or described herein (e.g., ELISA competitive assays, or suspension array or surface plasmon resonance assay). An antibody that "competitively inhibits" may also be referred to as an antibody that "competes for binding" to a reference antibody.

In specific aspects, provided herein is an antibody or antigen-binding fragment which competitively inhibits (e.g., in a dose dependent manner) binding of an antibody to human PILRA, wherein the antibody comprises a VH domain having the amino acid sequence set forth in SEQ ID NO:28, and a VL domain having the amino acid sequence set for the in SEQ ID NO:29.

In specific aspects, provided herein is an antibody or antigen-binding fragment which competitively inhibits (e.g., in a dose dependent manner) binding of an antibody to human PILRA, wherein the antibody comprises a VH domain having the amino acid sequence set forth in SEQ ID NO:30, and a VL domain having the amino acid sequence set for the in SEQ ID NO:31.

In specific aspects, provided herein is an antibody or antigen-binding fragment which competitively inhibits (e.g., in a dose dependent manner) binding of an antibody to human PILRA, wherein the antibody comprises a VH domain having the amino acid sequence set forth in SEQ ID NO:32, and a VL domain having the amino acid sequence set for the in SEQ ID NO:33.

In specific aspects, provided herein is an antibody or antigen-binding fragment which competitively inhibits (e.g., in a dose dependent manner) binding of an antibody to human PILRA, wherein the antibody comprises a VH domain having the amino acid sequence set forth in SEQ ID NO:34, and a VL domain having the amino acid sequence set for the in SEQ ID NO:35.

In some aspects, provided herein is an antibody or antigen-binding fragment that binds to human PILRA and does not competitively inhibit binding of 2175B to human PILRA.

Antigen Binding Fragments

In some aspects, an antigen-binding fragment of an anti-PILRA antibody described herein, such as an anti-human PILRA antibody, is provided. Exemplary antigen-binding fragments include but are not limited to Fab, Fab', F(ab')2, and scFv, wherein the Fab, Fab', F(ab')2, or scFv comprises a heavy chain variable region sequence and a light chain variable region sequence of an anti-human PILRA antibody as described herein. A Fab, Fab', F(ab')2, or scFv can be produced by any technique known to those of skill in the art, including, but not limited to, those discussed in Section 5.3, infra. In some aspects, an antigen-binding fragment, such as a Fab, Fab', F(ab')2, or scFv, further comprises a moiety that extends the half-life of the antibody in vivo. The moiety is also termed a "half-life extending moiety." Any moiety known to those of skill in the art for extending the half-life of a an antigen-binding fragment, such as a Fab, Fab', F(ab')2, or scFv, in vivo can be used. For example, the half-life extending moiety can include an Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In some aspects, an antigen-binding fragment, such as an Fab, Fab', F(ab')2, or scFv, can be modified by the addition of one or more C-terminal amino acids for attachment of the half-life extending moiety. In some aspects the half-life extending moiety is polyethylene glycol or human serum albumin. In some aspects, an antigen-binding fragment, such as a Fab, Fab', F(ab')2, or scFv, is fused to a Fc region.

An anti-PILRA antibody (such as an anti-human PILRA antibody) or antigen-binding fragment thereof can be fused or conjugated (e.g., covalently or noncovalently linked) to a detectable label or substance. Examples of detectable labels or substances include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin. Such labeled antibodies or antigen-binding fragments thereof can be used to detect PILRA (e.g., human PILRA) protein. See, e.g., Sections 5.4 and 5.5, infra.

5.3 Antibody Production

Antibodies and antigen-binding fragments thereof that immunospecifically bind to human PILRA can be produced by any method known in the art for the synthesis of antibodies and antigen-binding fragments, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates); Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a certain aspect, provided herein is a method of making an antibody or antigen-binding fragment which immunospecifically binds to human PILRA comprising culturing a cell or host cell described herein (e.g., a cell or a host cell comprising polynucleotides encoding an antibody or antigen-binding fragment thereof described herein). In a certain aspect, provided herein is a method of making an antibody or antigen-binding fragment thereof which immunospecifically binds to human PILRA comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In some aspects, the cell is an isolated cell. In some aspects, the encoding polynucleotides have been introduced into the cell. In some aspects, the method further comprises the step of purifying the antibody or antigen-binding fragment obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G& Milstein C (1975) Nature 256: 495. Examples of yeast-based presentation methods that can be employed to select and generate the antibodies described herein include those disclosed in, for example, WO2009/036379A2; WO2010/105256; and WO2012/009568, each of which is herein incorporated by reference in its entirety.

In some aspects, a monoclonal antibody or antigen-binding fragment is an antibody or antigen-binding fragment produced by a clonal cell (e.g., hybridoma or host cell producing a recombinant antibody or antigen-binding fragment), wherein the antibody or antigen-binding fragment immunospecifically binds to human PILRA as determined, e.g., by ELISA or other antigen-binding assays known in the art or in the Examples provided herein. In some aspects, a monoclonal antibody or antigen-binding fragment thereof can be a chimeric or a humanized antibody or antigen-binding fragment thereof. In some aspects, a monoclonal antibody or antigen-binding fragment thereof can be a Fab fragment or a F(ab')2 fragment. Monoclonal antibodies or antigen-binding fragments thereof described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of a tetrameric antibody molecule and contains the complete light chain paired with the VH and CH1 domains of the heavy chain. A F(ab')2 fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that binds to a particular antigen can be selected or identified with antigen, e.g., using labeled antigen or antigen bound or captured to a solid surface or bead. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

A humanized antibody or antigen-binding fragment thereof can be selected from any class of immunoglobulins, including IgM, IgG, IgD, IgA and IgE, and any isotype, including IgG1, IgG2, IgG3 and IgG4.

5.3.1 Polynucleotides

In certain aspects, provided herein are polynucleotides comprising a nucleotide sequence encoding an antibody or antigen-binding fragment thereof described herein or a domain thereof (e.g., a variable light chain region and/or variable heavy chain region) that immunospecifically binds to human PILRA, and vectors, e.g., vectors comprising such polynucleotides for recombinant expression in host cells (e.g., *E. coli* and mammalian cells).

In particular aspects, provided herein are polynucleotides comprising nucleotide sequences encoding antibodies or antigen-binding fragments thereof, which immunospecifically bind to human PILRA and comprise an amino acid sequence as described herein, as well as antibodies or antigen-binding fragments that compete with such antibodies or antigen-binding fragments for binding to a human PILRA (e.g., in a dose-dependent manner), or which bind to the same epitope as that of such antibodies or antigen-binding fragments.

Also provided herein is a polynucleotide comprising a nucleotide sequence encoding a polypeptide comprising a sequence selected from the group consisting of SEQ ID NOs:28-35. In some aspects, an antibody or antigen-binding fragment thereof comprising the polypeptide immunospecifically binds to human PILRA.

Also provided herein are kits, vectors, or host cells comprising (i) a first polynucleotide comprising a nucleotide sequence encoding SEQ ID NO:28 and (ii) a second polynucleotide comprising a nucleotide sequence encoding SEQ ID NO:29. Also provided herein are kits, vectors, or host cells comprising (i) a first polynucleotide comprising a nucleotide sequence encoding SEQ ID NO:30 and (ii) a second polynucleotide comprising a nucleotide sequence encoding SEQ ID NO:31. Also provided herein are kits, vectors, or host cells comprising (i) a first polynucleotide comprising a nucleotide sequence encoding SEQ ID NO:32 and (ii) a second polynucleotide comprising a nucleotide sequence encoding SEQ ID NO:33. Also provided herein are kits, vectors, or host cells comprising (i) a first polynucleotide comprising a nucleotide sequence encoding SEQ ID NO:34 and (ii) a second polynucleotide comprising a nucleotide sequence encoding SEQ ID NO:35. In a kit comprising such first and second polynucleotides, the first and second polynucleotides can be in the same vector or can be in different vectors. In a host cell comprising such first and second polynucleotides, the first and second polynucleotides can in the same vector or can be in different vectors.

In some aspects, provided herein are polynucleotides comprising a nucleotide sequence encoding three VH domain CDRs, e.g., a polypeptide containing VH CDR1, VH CDR2, and VH CDR3 of any one of antibodies described herein (e.g., see Table 1), e.g., wherein the three VH domain CDRs are in the context of a VH. In some aspects, provided herein are polynucleotides comprising a nucleotide sequence encoding three VL domain CDRs, e.g., a polypeptide containing VL CDR1, VL CDR2, and VL CDR3 of any one of antibodies described herein (e.g., see Table 2)), e.g., wherein the three VL domain CDRs are in the context of a VL. In some aspects, provided herein are polynucleotides (or combinations of polynucleotides) comprising a nucleotide sequence encoding an anti-human PILRA antibody or antigen-binding fragment thereof comprising (i) three VH domain CDRs, e.g., a polypeptide containing VH CDR1, VH CDR2, and VH CDR3 of any one of antibodies described herein (e.g., see Table 1) e.g., wherein the three VH domain CDRs are in the context of a VH and (ii) three VL domain CDRs, e.g., a polypeptide containing VL CDR1, VL CDR2, and VL CDR3 of any one of antibodies described herein (e.g., see Table 2) e.g., wherein the three VL domain CDRs are in the context of a VL.

In some aspects, provided herein are polynucleotides comprising a nucleotide sequence encoding an anti-human PILRA antibody or an antigen-binding fragment thereof or a fragment thereof comprising a VH domain, e.g., containing FR1-CDR1-FR2-CDR2-FR3-CDR3-FR4, comprising an amino acid sequence described herein (e.g., see Tables 1 and 5, e.g., the VH CDRs and VH FRs of a particular antibody identified by name in the tables). In some aspects, provided herein are polynucleotides comprising a nucleotide sequence encoding an anti-human PILRA antibody or antigen-binding fragment thereof or a fragment thereof comprising a VL domain, e.g., containing FR1-CDR1-FR2-CDR2-FR3-CDR3-FR4, comprising an amino acid sequence described herein (e.g., see Tables 2 and 6, e.g., the VL CDRs and VL FRs of a particular antibody identified by name in the Tables).

In some aspects, a polynucleotide comprises a nucleic acid sequence encoding a heavy chain variable region (e.g., a VH comprising the amino acid sequence of SEQ ID NO:28, 30, 32, or 34) and a heavy chain constant region, e.g., a human gamma (γ) heavy chain constant region.

In some aspects, a polynucleotide comprises a nucleic acid sequence encoding a light chain variable region (e.g., a VL comprising the amino acid sequence of SEQ ID NO:29, 31, 33, or 35) and a light chain constant region, e.g., a human lambda or kappa light chain constant region.

Also provided herein are polynucleotides encoding an anti-human PILRA antibody or antigen-binding fragment thereof described herein or a domain thereof that are optimized, e.g., by codon/RNA optimization, replacement with heterologous signal sequences, and elimination of mRNA instability elements. Methods to generate optimized nucleic acids encoding an anti-human PILRA antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate chimeric and humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In some aspects, the polynucleotide is a cDNA or a DNA lacking one more endogenous introns. In some aspects, a polynucleotide is a non-naturally occurring polynucleotide. In some aspects, a polynucleotide is recombinantly produced. In some aspects, the polynucleotides are isolated. In some aspects, the polynucleotides are substantially pure. In some aspects, a polynucleotide is purified from natural components.

5.3.2 Cells and Vectors

In certain aspects, provided herein are vectors (e.g., expression vectors) comprising polynucleotides comprising nucleotide sequences encoding anti-human PILRA antibodies and antigen-binding fragments thereof or a domain thereof for recombinant expression in host cells, preferably in mammalian cells. Also provided herein are cells, e.g. host cells, comprising such vectors for recombinantly expressing anti-human PILRA antibodies or antigen-binding fragments thereof described herein (e.g., human or humanized antibodies or antigen-binding fragments thereof). In some aspects, provided herein are methods for producing an antibody or antigen-binding fragments thereof described herein, comprising expressing such antibody or antigen-binding fragment thereof in a host cell.

In some aspects, recombinant expression of an antibody or antigen-binding fragment thereof or domain thereof described herein (e.g., a heavy or light chain described herein) that specifically binds to human PILRA involves construction of an expression vector containing a polynucleotide that encodes the antibody or antigen-binding fragment thereof or domain thereof. Once a polynucleotide encoding an antibody or antigen-binding fragment thereof or domain thereof (e.g., heavy or light chain variable domain) described herein has been obtained, the vector for the production of the antibody or antigen-binding fragment thereof can be produced by recombinant DNA technology using techniques well known in the art. Thus, methods for preparing a protein by expressing a polynucleotide containing an antibody or antigen-binding fragment thereof or domain thereof (e.g., light chain or heavy chain) encoding nucleotide sequence are described herein. Methods which are well known to those skilled in the art can be used to construct expression vectors containing antibody or antigen-binding fragment thereof or domain thereof (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment thereof described herein, a heavy or light chain, a heavy or light chain variable domain, or a heavy or light chain CDR, operably linked to a promoter. Such vectors can, for example, include the nucleotide sequence encoding the constant region of the antibody or antigen-binding fragment thereof (see, e.g., International Publication Nos. WO 86/05807 and WO 89/01036; and U.S. Pat. No. 5,122,464), and variable domains of the antibody or antigen-binding fragment thereof can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody or antigen-binding fragment thereof described herein (e.g., an antibody or antigen-binding fragment thereof comprising the six CDRs, the VH, the VL, the VH and the VL, the heavy chain, the light chain, or the heavy and the light chain of hPA-002, hPA-005, hPA-004, or hPA-001) or a domain thereof (e.g., the VH, the VL, the VH and the VL, the heavy chain, or the light chain of hPA-002, hPA-005, hPA-004, or hPA-001). Thus, provided herein are host cells containing a polynucleotide encoding an antibody or antigen-binding fragment thereof described herein (e.g., an antibody or antigen-binding fragment thereof comprising the six CDRs, the VH, the VL, the VH and the VL, the heavy chain, the light chain, or the heavy and the light chain of hPA-002, hPA-005, hPA-004, or hPA-001) or a domain thereof (e.g., the VH, the VL, the VH and the VL, the heavy chain, or the light chain of hPA-002, hPA-005, hPA-004, or hPA-001), operably linked to a promoter for expression of such sequences in the host cell. In some aspects, for the expression of double-chained antibodies or antigen-binding fragments thereof, vectors encoding both the heavy and light chains, individually, can be co-expressed in the host cell for expression of the entire immunoglobulin, as detailed below. In some aspects, a host cell contains a vector comprising a polynucleotide encoding both the heavy chain and light chain of an antibody described herein (e.g., the heavy and the light chain of hPA-002, hPA-005, hPA-004, or hPA-001), or a domain thereof (e.g., the VH and the VL of hPA-002, hPA-005, hPA-004, or hPA-001). In some aspects, a host cell contains two different vectors, a first vector comprising a polynucleotide encoding a heavy chain or a heavy chain variable region of an antibody or antigen-binding fragment thereof described herein, and a second vector comprising a polynucleotide encoding a light chain or a light chain variable region of an antibody described herein (e.g., an antibody comprising the six CDRs of hPA-002, hPA-005, hPA-004, or hPA-001), or a domain thereof. In some aspects, a first host cell comprises a first vector comprising a polynucleotide encoding a heavy chain or a heavy chain variable region of an antibody or antigen-binding fragment thereof described herein, and a second host cell comprises a second vector comprising a polynucleotide encoding a light chain or a light chain variable region of an antibody or antigen-binding fragment thereof described herein (e.g., an antibody or antigen-binding fragment thereof comprising the six CDRs of hPA-002, hPA-005, hPA-004, or hPA-001). In some aspects, a heavy chain/heavy chain variable region expressed by a first cell associated with a light chain/light chain variable region of a second cell to form an human PILRA antibody or antigen-binding fragment thereof described herein (e.g., antibody or antigen-binding fragment thereof comprising the six CDRs of hPA-002, hPA-005, hPA-004, or hPA-001). In some aspects, provided herein is a population of host cells comprising such first host cell and such second host cell.

In some aspects, provided herein is a population of vectors comprising a first vector comprising a polynucleotide encoding a light chain/light chain variable region of an anti-human PILRA antibody or antigen-binding fragment thereof described herein, and a second vector comprising a polynucleotide encoding a heavy chain/heavy chain variable region of an anti-human PILRA antibody or antigen-binding fragment thereof described herein (e.g., antibody or antigen-binding fragment thereof comprising the CDRs of hPA-002, hPA-005, hPA-004, or hPA-001). Alternatively, a single vector can be used which encodes, and is capable of expressing, both heavy and light chain polypeptides.

A variety of host-expression vector systems can be utilized to express antibodies and antigen-binding fragments thereof described herein (e.g., an antibody or antigen-binding fragment thereof comprising the CDRs of hPA-002, hPA-005, hPA-004, or hPA-001) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some aspects, cells for expressing antibodies and antigen-binding fragments thereof described herein (e.g., an antibody or antigen-binding fragment thereof comprising the CDRs of hPA-002, hPA-005, hPA-004, or hPA-001) are CHO cells, for example CHO cells from the CHO GS System™ (Lonza). In some aspects, cells for expressing antibodies described herein are human cells, e.g., human cell lines. In some aspects, a mammalian expression vector is pOptiVEC™ or pcDNA3.3. In some aspects, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In some aspects, antibodies or antigen-binding fragments thereof described herein are produced by CHO cells or NS0 cells.

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In some aspects, anti-human PILRA antibodies or antigen-binding fragments thereof described herein (e.g., an antibody or antigen-binding fragment thereof comprising the CDRs of hPA-002, hPA-005, hPA-004, or hPA-001) are produced in mammalian cells, such as CHO cells.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In some aspects, an antibody or antigen-binding fragment thereof described herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in some aspects, a preparation of an antibody or antigen-binding fragment thereof described herein is substantially free of cellular material and/or chemical precursors.

5.4 Pharmaceutical Compositions

Provided herein are compositions comprising an anti-PILRA antibody (such as an anti-human PILRA antibody) or antigen-binding fragment thereof, as described herein. In some aspects, the antibody or antigen-binding fragment thereof having the desired degree of purity is present in a formulation comprising, e.g., a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed. Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In some aspects, a pharmaceutical composition comprises an anti-human PILRA antibody or antigen-binding fragment thereof as described herein, and a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Pharmaceutical compositions described herein are, in some aspects, for use as a medicament. The compositions to be used for in vivo administration can be sterile. This is readily accomplished by filtration through, e.g., sterile filtration membranes.

A pharmaceutical composition described herein can be used to exert a biological effect(s) in vivo or in vitro. For example, a pharmaceutical composition described herein can be used to activate myeloid cells, promote differentiation of myeloid cells, inhibit binding of PILRA to one or more of its ligands and/or to cells expressing such ligands (e.g., T cells), and/or downregulate cell surface PILRA.

A pharmaceutical compositions described herein can be used to treat a disease or condition, such as a disease or condition that would be alleviated by activating myeloid cells, promoting the differentiation of myeloid cells, inhibiting the binding of PILRA to one or more of its ligands and/or to cells expressing such ligands (e.g., T cells), and/or downregulating cell surface PILRA. A pharmaceutical composition described herein can be used to treat a disease or condition in which myeloid cells are dysfunctional (e.g., hypoactive) or deficient, e.g., a disease or condition in which myeloid cell activation or differentiation is desired, or in which activation of the innate immune system is desired.

In some aspects, a pharmaceutical composition provided herein is used to treat diseases or conditions such as cancer. Examples of cancers that can be treated as provided herein include solid tumors, e.g., solid tumors in which myeloid cells (monocytes, macrophages, dendritic cells, granulocytes, neutrophils, microglia (in the CNS) or other innate immune cells) have infiltrated the tumor microenvironment. Examples of such cancers that can be treated by the pharmaceutical compositions provided herein include, but are not limited to, glioblastoma, head and neck cancer, kidney cancer (e.g., kidney clear cell cancer), pancreatic cancer, and breast cancer. Other cancers include, but are not limited to, ovarian cancer, sarcoma, colorectal cancer, lung cancer, melanoma, bladder cancer, liver cancer and uterine cancer. In some aspects, a cancer is a hematopoietic cancer, such as a leukemia, lymphoma, or myeloma. In some aspects, a cancer may be an early stage cancer or a late stage cancer. In some aspects, a cancer is a primary tumor. In some aspects, a cancer is a metastatic tumor at a second site derived from any of the above types of cancer. In some aspects, a cancer is a PILRA-positive cancer. In some aspects, a cancer is a cancer with increased PILRA (e.g. increased PILRA mRNA and/or increased PILRA protein).

In some aspects, a pharmaceutical composition provided herein is used to treat a neurodegenerative disease. In some aspects, the neurodegenerative disease is characterized by dysfunctional (e.g., hypoactive) or deficient myeloid cells, such as microglia. In some aspects, the neurodegenerative disease is an immune-mediated neurodegenerative disease. In some aspects, the neurodegenerative disease is selected from Alzheimer's disease, dementia, frontotemporal dementia (FTD), vascular dementia, mild cognitive impairment, Parkinson's disease, amyotrophic lateral sclerosis (ALS), Huntington's disease, Tauopathy disease, multiple sclerosis, immune-mediated neuropathies (such as neuropathic pain), Nasu-Hakola disease, pediatric-onset leukoencephalopathy, adult-onset leukoencephalopathy with axonal spheroids and pigmented glia (ALSP), and limbic-predoninant age-related TDP43 encephalopathy (LATE).

In some aspects, a pharmaceutical composition provided herein is used to inhibit HSV-1 infection. In some aspects, a pharmaceutical composition provided herein is used to inhibit HSV-1 reoccurance.

5.5 Uses and Methods

In various aspects, provided herein are in vitro and in vivo methods of using anti-human PILRA antibodies or antigen-binding fragments thereof as described herein, or pharmaceutical compositions thereof as described herein. In one aspect, a method of activating a myeloid cell is provided, the method comprising exposing the cell to an anti-human PILRA antibody or antigen-binding fragment thereof, or pharmaceutical composition thereof. In another aspect, a method of promoting differentiation of a myeloid cell is provided, the method comprising exposing the cell to an anti-human PILRA antibody or antigen-binding fragment thereof, or pharmaceutical composition thereof. In another aspect, a method of inhibiting binding of PILRA to one or more of its ligands is provided, the method comprising contacting PILRA with an anti-human PILRA antibody or antigen-binding fragment thereof, or pharmaceutical composition thereof, in the presence of one or more of its ligands. Exemplary ligands include glycosylated proteins, such as those with a PTPXP, PTPXXP, PXTPXP, or PXTPXXP motif Exemplary ligands include, e.g., COLEC12, NPDC1, CLEC4G, and PIANP, as well as the HSV-1 glycoprotein B. In certain aspects, PILRA and/or the one or more of its ligands are expressed on cells. In another aspect, a method of downregulating cell surface PILRA is provided, the method comprising exposing a cell expressing PILRA on its surface to an anti-human PILRA antibody or antigen-binding fragment thereof, or pharmaceutical composition thereof.

5.5.1 Therapeutic Uses and Methods

In some aspects, provided herein are methods for increasing myeloid cell activation in a subject (e.g., a human subject) in need thereof, comprising administering to the subject an anti-human PILRA antibody or antigen-binding fragment thereof as described herein, or a pharmaceutical composition thereof as described herein. In some aspects, provided herein are methods for promoting myeloid cell differentiation in a subject (e.g., a human subject) in need thereof, comprising administering to the subject an anti-human PILRA antibody or antigen-binding fragment thereof as described herein, or a pharmaceutical composition thereof as described herein.

In some aspects, methods are provided in which an anti-human PILRA antibody or antigen-binding fragment thereof as described herein, or pharmaceutical composition as described herein, is administered to a subject (e.g., a human subject) in need thereof to inhibit interaction of PILRA with one or more of its ligands (e.g., NPDC1) in the subject. In some aspects, methods are provided in which an anti-human PILRA antibody or antigen-binding fragment thereof as described herein, or pharmaceutical composition thereof as described herein, is administered to a subject (e.g., a human subject) in need thereof to downregulate cell surface PILRA in the subject.

In some aspects, the anti-human PILRA antibody or antigen-binding fragment thereof, or pharmaceutical composition thereof, is administered to achieve any two or more of the above effects.

In some aspects, provided herein are methods of treating a disease or condition that would be alleviated by activating myeloid cells, promoting the differentiation of myeloid cells, inhibiting the binding of PILRA to one or more of its ligands and/or downregulating cell surface PILRA. Such methods can comprise administering an anti-human PILRA antibody or antigen-binding fragment thereof as described herein, or a pharmaceutical composition thereof as described herein, to a patient (e.g., a human patient) in need thereof.

In some aspects, provided herein are methods of treating a disease or condition in which myeloid cells are dysfunctional (e.g., hypoactive) or deficient, e.g., a disease or condition in which myeloid cell activation or differentiation is desired, or in which activation of the innate immune system is desired. Such methods can comprise administering an anti-human PILRA antibody or antigen-binding fragment thereof as described herein, or a pharmaceutical composition thereof as described herein, to a patient (e.g., a human patient) in need thereof. A disease or condition in which myeloid cells are dysfunctional may include cancer or neurodegenerative diseases, as further described herein.

In some aspects, provided herein are methods of treating cancer. A method of treating cancer can comprise administering an anti-human PILRA antibody or antigen-binding fragment thereof as described herein, or a pharmaceutical composition thereof as described herein, to a patient (e.g., a human patient) in need thereof. In some aspects, provided herein are methods of treating cancer, wherein the cancer is a solid tumor. Solid tumors include those in which myeloid cells (monocytes, macrophages, dendritic cells, granulocytes, neutrophils, microglia (in the CNS) or other innate immune cells) have infiltrated the tumor microenvironment. Examples of such cancers that can be treated as provided herein include, but are not limited to, glioblastoma, head and neck cancer, kidney cancer (e.g., kidney clear cell cancer), pancreatic cancer, and breast cancer. Other cancers include, but are not limited to, ovarian cancer, sarcoma, colorectal cancer, lung cancer, melanoma, bladder cancer, liver cancer, and uterine cancer.

In some aspects, a cancer to be treated by the methods of the present disclosure includes, without limitation, a hematopoietic cancer, such as a leukemia, lymphoma, or myeloma. In some aspects, a cancer to be treated by the methods of the present disclosure may be an early stage cancer or a late stage cancer. In some aspects, a cancer may be a primary tumor. In some aspects, a cancer may be a metastatic tumor at a second site derived from any of the above types of cancer.

In some aspects, a cancer to be treated by the methods of the present disclosure is a PILRA-positive cancer. In some aspects, a cancer to be treated by the methods of the present invention is a cancer with increased PILRA (e.g. increased PILRA mRNA and/or increased PILRA protein).

In some aspects, a method of treating a cancer is provided, wherein the method comprises administering an anti-human PILRA antibody or antigen-binding fragment thereof, or pharmaceutical composition thereof, and wherein the method further comprises administering an antagonist of an inhibitory immune checkpoint molecule. In some aspects, the inhibitory checkpoint molecule is PD-1 (programmed cell death protein-1) or its ligand PD-L1 (programmed death ligand-1). In some aspects, an antagonist of PD-1 is an antibody to PD-1. PD-1 antibodies include, for example, OPDIVO (nivolumab), KEYTRUDA (pembrolizumab), MEDI-0680 (AMP-514; WO2012/145493), camrelizumab (SHR-1210), tislelizumab (BGB-A317), or spartalizumab (NPVPDR001, NVS240118, PDR001). A recombinant protein composed of the extracellular domain of PD-L2 (B7-DC) lused to the Fc portion of IgG1, called AMP-224, can also be used to antagonize the PD-1 receptor. In some aspects, an antagonist of PD-L1 is an antibody to PD-L1. PD-L1 antibodies include, for example, TECENTRIQ (atezolizumab), durvalumab (MEDI4736), BMS-936559 (WO2007/005874), MSB0010718C (WO2013/79174) or rHigM12B7. In some aspects, an anti-human PILRA antibody or antigen-binding fragment thereof, or pharmaceutical composition thereof, is administered in combination with radiation therapy and/or a chemotherapeutic agent.

In some aspects, provided herein are methods of inhibiting HSV-1 infection and/or HSV-1 reoccurance. A method of inhibiting HSV-1 infection and/or reoccurance can comprise administering an anti-human PILRA antibody or antigen-binding fragment thereof as described herein, or a pharmaceutical composition thereof as described herein, to a patient (e.g., a human patient) in need thereof.

In some aspects, provided herein are methods of treating a neurodegenerative disease. A method of treating a neurodegenerative disease can comprise administering an anti-human PILRA antibody or antigen-binding fragment thereof as described herein, or a pharmaceutical composition thereof as described herein, to a patient (e.g., a human patient) in need thereof. In some aspects, the neurodegenerative disease is characterized by dysfunctional (e.g., hypoactive) or deficient myeloid cells, such as microglia. Microglia are innate immune cells that reside specifically in the brain and that function as macrophages, clearing debris and dead neurons through the process of phagocytosis and providing other supportive functions for maintaining brain health. In some aspects, the patient has symptoms of a neurodegenerative disease, and an anti-human PILRA antibody or antigen-binding fragment thereof as described herein, or a pharmaceutical composition thereof as described herein, is administered to treat the neurodegenerative disease. In some aspects, the patient is at risk of developing a neurodegenerative disease, and the anti-human PILRA antibody, antigen-binding fragment, or pharmaceutical composition is administered to reduce risk, slow onset, or prevent the neurodegenerative disease.

In some aspects, the neurodegenerative disease is an immune-mediated neurodegenerative disease. In some aspects, the neurodegenerative disease is selected from Alzheimer's disease, dementia, frontotemporal dementia (FTD), vascular dementia, mild cognitive impairment, Parkinson's disease, amyotrophic lateral sclerosis (ALS), Huntington's disease, Tauopathy disease, multiple sclerosis (MS), immune-mediated neuropathies (such as neuropathic pain), Nasu-Hakola disease, pediatric-onset leukoencephalopathy, adult-onset leukoencephalopathy with axonal spheroids and pigmented glia (ALSP), and limbic-predominant age-related TDP43 encephalopathy (LATE).

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier. Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some aspects, administering an anti-human PILRA antibody or antigen-binding fragment thereof as provided herein, or a pharmaceutical composition thereof as provided herein, can prevent, reduce the risk, and/or treat Alzheimer's disease. In some aspects, administering the anti-human PILRA antibody, antigen-binding fragment or pharmaceutical composition may modulate one or more PILRA activities in an individual having Alzheimer's disease.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some aspects, administering an anti-human PILRA antibody or antigen-binding fragment thereof as provided herein, or a pharmaceutical composition thereof as provided herein, can prevent, reduce the risk, and/or treat dementia. In some aspects, administering the anti-human PILRA antibody, antigen-binding fragment or pharmaceutical composition may modulate one or more PILRA activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

In some aspects, administering an anti-human PILRA antibody or antigen-binding fragment thereof as provided herein, or a pharmaceutical composition thereof as provided herein, of the present disclosure, can prevent, reduce the risk, and/or treat FTD. In some aspects, administering the anti-human PILRA antibody, antigen-binding fragment or pharmaceutical composition may modulate one or more PILRA activities in an individual having FTD.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some aspects, administering an anti-human PILRA antibody or antigen-binding fragment thereof as provided herein, or a pharmaceutical composition thereof as provided herein, can prevent, reduce the risk, and/or treat Parkinson's disease. In some aspects, administering the anti-human PILRA antibody, antigen-binding fragment or pharmaceutical composition may modulate one or more PILRA activities in an individual having Parkinson's disease.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

In some aspects, administering an anti-human PILRA antibody or antigen-binding fragment thereof as provided herein, or a pharmaceutical composition thereof as provided herein, can prevent, reduce the risk, and/or treat ALS. In some aspects, administering the anti-human PILRA antibody, antigen-binding fragment or pharmaceutical composition may modulate one or more PILRA activities in an individual having amyotrophic lateral sclerosis.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some aspects, administering an anti-human PILRA antibody or antigen-binding fragment thereof as provided herein, or a pharmaceutical composition thereof as provided herein, can prevent, reduce the risk, and/or treat Huntington's disease (HD). In some aspects, administering the anti-human PILRA antibody, antigen-binding fragment or pharmaceutical composition may modulate one or more PILRA activities in an individual having Huntington's disease.

Tauopathy Disease

Tauopathy diseases, or Tauopathies, are a class of neurodegenerative disease caused by aggregation of the microtubule-associated protein tau within the brain. Alzheimer's disease (AD) is the most well-known tauopathy disease and involves an accumulation of tau protein within neurons in the form of insoluble neurofibrillary tangles (NFTs). Other tauopathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some aspects, administering an anti-human PILRA antibody or antigen-binding fragment thereof as provided herein, or a pharmaceutical composition thereof as provided herein, can prevent, reduce the risk, and/or treat a tauopathy disease. In some aspects, administering the anti-human PILRA antibody, antigen-binding fragment or pharmaceutical composition may modulate one or more PILRA activities in an individual having a tauopathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoffs phenomenon, which is an exacerbation of extant symptoms due to an exposure to higher than usual ambient temperatures; and Lhermitte's sign, which is an electrical sensation that runs down the back when bending the neck.

In some aspects, administering an anti-human PILRA antibody or antigen-binding fragment thereof as provided herein, or a pharmaceutical composition thereof as provided herein, can prevent, reduce the risk, and/or treat MS. In some aspects, administering the anti-human PILRA antibody, antigen-binding fragment or pharmaceutical composition may modulate one or more PILRA activities in an individual having MS.

Administration and Dosing

An anti-human PILRA antibody or antigen-binding fragment thereof as provided herein, or a pharmaceutical composition thereof as provided herein, can be administered by any suitable means, including parenteral, intrapulmonary, intranasal, intratumoral, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some aspects, the administration is intravenous administration. In some aspects, the administration is subcutaneous.

The appropriate dosage and dosing regimen of an anti-human PILRA antibody or antigen-binding fragment thereof as provided herein, or a pharmaceutical composition thereof as provided herein, when used alone or in combination with one or more other additional therapeutic agents, will depend on the disease to be treated, the severity and course of the disease, the route of administration and other factors.

In some aspects, provided herein is an antibody or antigen-binding fragment thereof or pharmaceutical composition provided herein for use as a medicament.

In some aspects, provided herein is an antibody or antigen-binding fragment thereof or pharmaceutical composition provided herein, for use in a method for the treatment of cancer. In some aspects, provided herein is an antibody or antigen-binding fragment thereof or pharmaceutical composition provided herein, for use in a method for the treatment of cancer in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for the treatment of a neurodegenerative disease. In some aspects, provided herein is an antibody or antigen-binding fragment thereof or pharmaceutical composition provided herein, for use in a method for the treatment of a neurodegenerative disease in a subject, comprising administering to the subject an effective amount of an antibody or antigen-binding fragment thereof or pharmaceutical composition provided herein.

5.5.2 Detection and Diagnostic Uses

An anti-human PILRA antibody or antigen-binding fragment thereof described herein (see, e.g., Section 5.2) can be used to assay PILRA protein (e.g., human PILRA protein) levels in a biological sample using classical methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin. Such labels can be used to label an antibody or antigen-binding fragment thereof described herein. Alternatively, a second antibody or antigen-binding fragment thereof that recognizes an anti-human PILRA antibody or antigen-binding fragment thereof described herein can be labeled and used in combination with an anti-human PILRA antibody or antigen-binding fragment thereof to detect PILRA protein (e.g., human PILRA protein) levels.

Assaying for the expression level of PILRA protein (e.g., human PILRA protein) is intended to include qualitatively or quantitatively measuring or estimating the level of a PILRA protein (e.g., human PILRA protein) in a first biological sample either directly (e.g., by determining or estimating absolute protein level) or relatively (e.g., by comparing to the disease associated protein level in a second biological sample). PILRA protein (e.g., human PILRA protein) expression level in the first biological sample can be measured or estimated and compared to a standard PILRA protein (e.g., human PILRA protein) level, the standard being taken from a second biological sample obtained from an individual not having the disorder or being determined by averaging levels from a population of individuals not having the disorder. As will be appreciated in the art, once the "standard" PILRA protein (e.g., human PILRA protein) level is known, it can be used repeatedly as a standard for comparison.

As used herein, the term "biological sample" refers to any biological sample obtained from a subject, cell line, tissue, or other source of cells potentially expressing PILRA protein (e.g., human PILRA protein). Methods for obtaining tissue biopsies and body fluids from animals (e.g., humans) are well known in the art.

An anti-human PILRA antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction, cancer or neurodegenerative disease, such as Alzheimer's disease.

Anti-human PILRA antibodies and antigen-binding fragments thereof described herein can carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-human PILRA antibodies or antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-human PILRA antibody can carry a radioactive label, such as the isotopes 3H, 14C, 32P, 35S, 36Cl, 51Cr, 57Co, 58Co, 59Fe, 67Cu, 90Y, 99Tc, 111In, 117Lu, 121I, 124I, 125I, 131I, 198Au, 211At, 213Bi, 225Ac and 186Re. When radioactive labels are used, currently available counting procedures known in the art may be utilized to identify and quantitate the specific binding of anti-human PILRA antibody or antigen-binding fragment to PILRA protein (e.g., human PILRA protein). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-human PILRA antibody or antigen-binding fragment thereof under conditions that allow for the formation of a complex between the antibody or antigen-binding fragment thereof and PILRA protein (e.g., human PILRA protein). Any complexes formed between the antibody or antigen-binding fragment thereof and PILRA protein (e.g., human PILRA protein) are detected and compared in the sample and the control. In light of the specific binding of the antibodies or antigen-binding fragments thereof described herein to human PILRA, the antibodies or antigen-binding fragments thereof can be used to specifically detect PILRA protein (e.g., human PILRA protein) expression on the surface of cells. The antibodies or antigen-binding fragments thereof described herein can also be used to purify PILRA protein (e.g., human PILRA protein) via immunoaffinity purification.

Also included herein is an assay system which may be prepared in the form of a test kit for the quantitative analysis of the extent of the presence of PILRA protein (e.g., human PILRA protein). The system or test kit may comprise a labeled component, e.g., a labeled antibody or antigen-binding fragment, and one or more additional immunochemical reagents. See, e.g., Section 5.6 below for more on kits.

In some aspects, methods for in vitro detection of PILRA protein (e.g., human PILRA protein) in a sample, comprising contacting said sample with an antibody or antigen-binding fragment thereof, are provided herein. In some aspects, provided herein is the use of an antibody or antigen-binding fragment thereof provided herein, for in vitro detection of PILRA protein (e.g., human PILRA protein) in a sample. In some aspects, provided herein is an antibody or antigen-binding fragment thereof or composition provided herein for use in the detection of PILRA protein (e.g., human PILRA protein) in a subject or a sample obtained from a subject. In some aspects, provided herein is an antibody or antigen-binding fragment thereof provided herein for use as a diagnostic. In some aspects, the antibody comprises a detectable label.

5.6 Kits

Provided herein are kits comprising one or more antibodies or antigen-binding fragments thereof described herein. In some aspects, provided herein is a pharmaceutical pack or kit comprising one or more containers filled with one or more of the ingredients of the pharmaceutical compositions described herein, such as one or more antibodies or antigen-binding fragments thereof provided herein. Optionally associated with such container(s) can be a notice in the form prescribed by a governmental agency regulating the manufacture, use, or sale of pharmaceuticals or biological products, which notice reflects approval by the agency of manufacture, use or sale for human administration.

Also provided herein are kits that can be used in detection methods. In some aspects, a kit comprises an antibody or antigen-binding fragment thereof described herein, preferably a purified antibody or antigen-binding fragment thereof, in one or more containers. In some aspects, kits described herein contain a substantially isolated PILRA protein (e.g., human PILRA protein) that can be used as a control. In some aspects, the kits described herein further comprise a control antibody or antigen-binding fragment thereof which does not react with PILRA protein (e.g., human PILRA protein). In some aspects, kits described herein contain one or more elements for detecting the binding of an antibody or antigen-binding fragment thereof to PILRA protein (e.g., human PILRA protein) (e.g., the antibody or antigen-binding fragment thereof can be conjugated to a detectable substrate such as a fluorescent compound, an enzymatic substrate, a radioactive compound or a luminescent compound, or a second antibody or antigen-binding fragment thereof which recognizes the first antibody or antigen-binding fragment thereof can be conjugated to a detectable substrate). In some aspects, a kit provided herein can include a recombinantly produced or chemically synthesized PILRA protein (e.g., human PILRA protein). The PILRA protein (e.g., human PILRA protein) provided in the kit can also be attached to a solid support. In some aspects, the detecting means of the above described kit includes a solid support to which a PILRA protein (e.g., human PILRA protein) is attached. Such a kit can also include a non-attached reporter-labeled anti-human antibody or antigen-binding fragment thereof or anti-mouse/rat antibody or antigen-binding fragment thereof. In this aspect, binding of the antibody or antigen-binding fragment thereof to the PILRA protein (e.g., human PILRA protein) can be detected by binding of the said reporter-labeled antibody or antigen-binding fragment thereof.

6. EXAMPLES

The examples in this Section (i.e., Section 6) are offered by way of illustration, and not by way of limitation.

Example 1: Anti-PILRA Antibodies Inhibit Binding of PILRA to T Cells

In order to test the ability of human PILRA to bind to T cells, a soluble human PILRA hIgG1 Fc construct ("PILRA Fc") was used. The amino acid sequence of PILRA Fc is provided in SEQ ID NO:74.

```
                                          (SEQ ID NO: 74)
QPSGSTGSGPSYLYGVTQPKHLSASMGGSVEIPFSFYYPWELATAPDVRI

SWRRGHFHGQSFYSTRPPSIHKDYVNRLFLNWTEGQKSGFLRISNLQKQD

QSVYFCRVELDTRSSGRQQWQSIEGTKLSITQGQQRTKATTPAREPFQNT

EEPYENIRNEGQNTDPKLNPKLHLTQSTSQPPSPQEPPERDPVLCLKGLT

NGQPSQDADDDDKEPKSSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

Figure 1A:
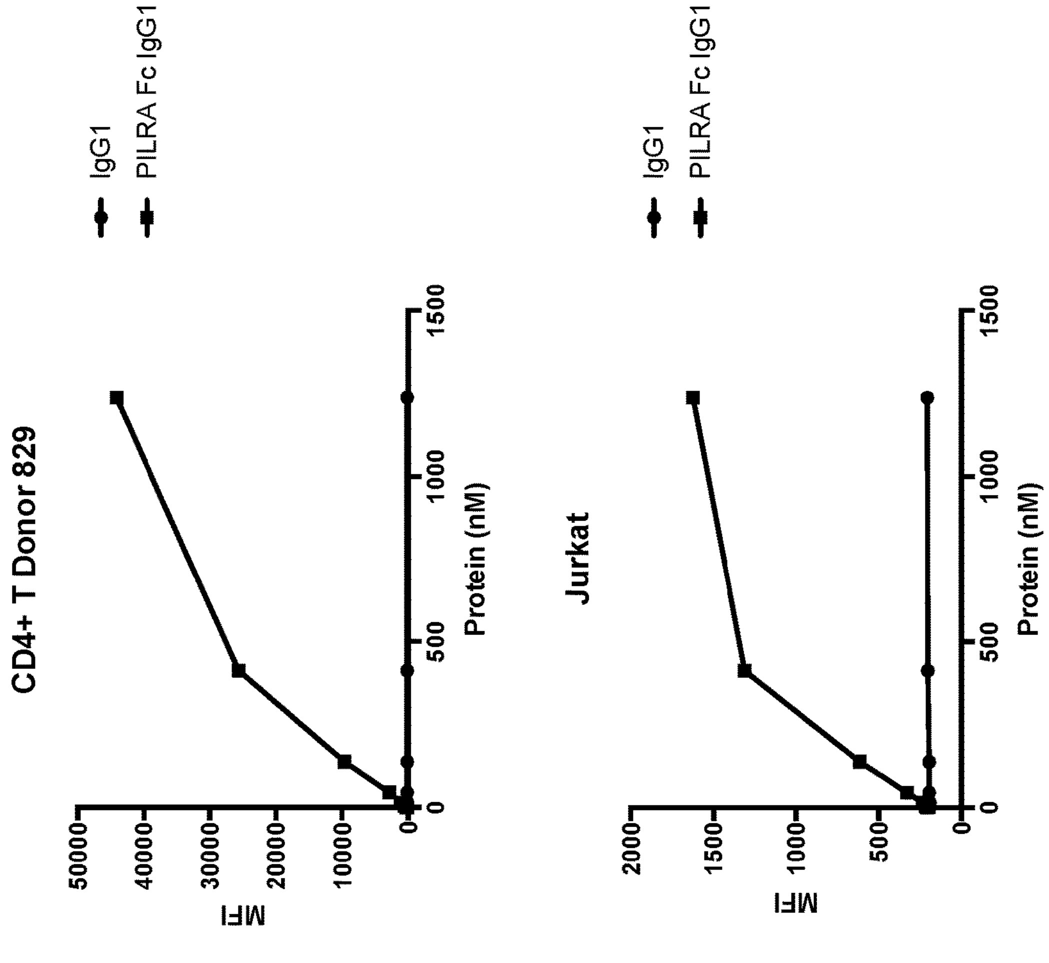
FIG. 1A shows the binding of primary CD4+ T cells or Jurkat cells to PILRA Fc or IgG1 isotype control. (See Example 1.)

PILRA Fc or hIgG1 isotype control was incubated with primary CD4+ T cells or Jurkat cells for 30 minutes at 4° C. Cells were washed twice, and then bound PILRA Fc or IgG1 isotype control was detected with anti-human IgG1 Alexa 647. Cells were acquired on a BD FACS Canto, and mean fluorescent intensity was calculated. As shown in FIG. 1A, binding of PILRA Fc was detected on CD4+ T cells and Jurkat cells.

The ability of anti-PILRA antibodies to inhibit binding of PILRA Fe to T cells was tested. An anti-PILRA antibody that binds to PILRA-Fc and blocks binding of PILRA-Fc to T cells is presumed to be blocking binding of PILRA-Fc to a PILRA ligand on T cells. An antibody with this activity would likewise be expected to function in blocking the binding of endogenous PILRA to its ligand on T cells, thereby suppressing the inhibitory signaling of endogenous PILRA.

Figure 1B:
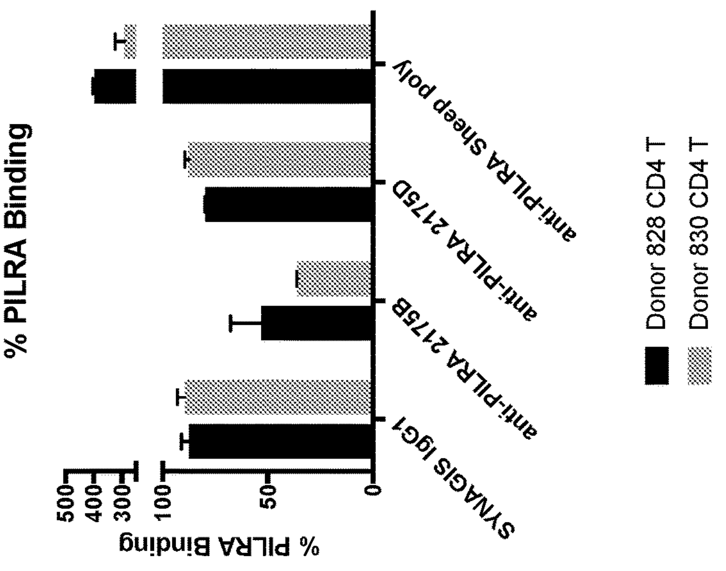
FIG. 1B shows that an anti-PILRA antibody inhibits binding of PILRA Fc to CD4+ T cells. (See Example 1.)

To test the ability of anti-PILRA antibodies to inhibit binding of PILRA Fc to T cells, PILRA Fc was first incubated with 10 ug/ml of anti-PILRA antibodies, isotype control IgG1, or FACS buffer only for 30 minutes at 4° C. $CD4^+$ T cells from 2 healthy donors were added and further incubated for additional 30 minutes. After washing two times, PILRA Fc bound to $CD4^+$ T cells was detected with anti-human IgG Alexa 647. The extent of PILRA Fc binding in the presence of anti-PILRA antibodies or isotype control was calculated relative to the extent of PILRA Fc binding in the presence of FACS buffer only. Anti-human PILRA antibody 2175B (R&D Systems) partially inhibited PILRA Fc binding (FIG. 1B). In contrast, the anti-human PILRA antibody 2175D (R&D Systems) had no effect on binding, and the anti-human PILRA sheep polyclonal antibody (R&D Systems) increased binding (FIG. 1B). In conclusion, binding of PILRA Fc to T cells may be inhibited or enhanced depending on the anti-human PILRA antibody that is used.

Example 2: PILRA Regulates Differentiation and Activation of Myeloid Derived Suppressor Cells To determine the role of PILRA in myeloid cell activation and differentiation, myeloid derived suppressor cells (MDSCs) were generated from monocytes of 3 healthy donors by culturing with 100 ng/ml GM-CSF and 100 ng/ml IL-6 for 5 days. Cells were then harvested and treated with vehicle or with increasing doses of mIgG1 isotype control or a human PILRA Fc (mIgG1) construct ("PILRA mFc"). The amino acid sequence PILRA mFc construct is provided in SEQ ID NO:75.

(SEQ ID NO: 75)

QPSGSTGSGPSYLYGVTQPKHLSASMGGSVEIPFSFYYPWELATAPDVRI

SWRRGHFHGQSFYSTRPPSIHKDYVNRLFLNWTEGQKSGFLRISNLQKQD

QSVYFCRVELDTRSSGRQQWQSIEGTKLSITQAVTTTTQRPSSMTTTWRL

SSTTTTTGLRVTQGKRRSDSWHISLETAGGSGVPRDCGCKPCICTVPEVS

SVFIFPPKPKDVLTITLTPKVTCVVVDISKDDPEVQFSWFVDDVEVHTAQ

TQPREEQFNSTFRSVSELPIMHQDWLNGKEFKCRVNSAAFPAPIEKTISK

TKGRPKAPQVYTIPPPKEQMAKDKVSLTCMITDFFPEDITVEWQWNGQPA

ENYKNTQPIMDTDGSYFIYSKLNVQKSNWEAGNTFTCSVLHEGLHNHHTE

KSLSHSPGK

PILRA mFc acts as a soluble antagonist, binding PILRA ligands expressed on these cells, and preventing their interaction with cell surface endogenous PILRA receptor. After 3 days of treatment, cells were harvested and activation of MDSCs was examined by staining for CD14 and CD86. CD14 is a myeloid marker that is downregulated upon differentiation from immature myeloid to a more mature myeloid cell type. CD86 is an activation marker on myeloid cells, a potent activator of the adaptive immune response, and a prototypic M1 gene.

Figure 2A:
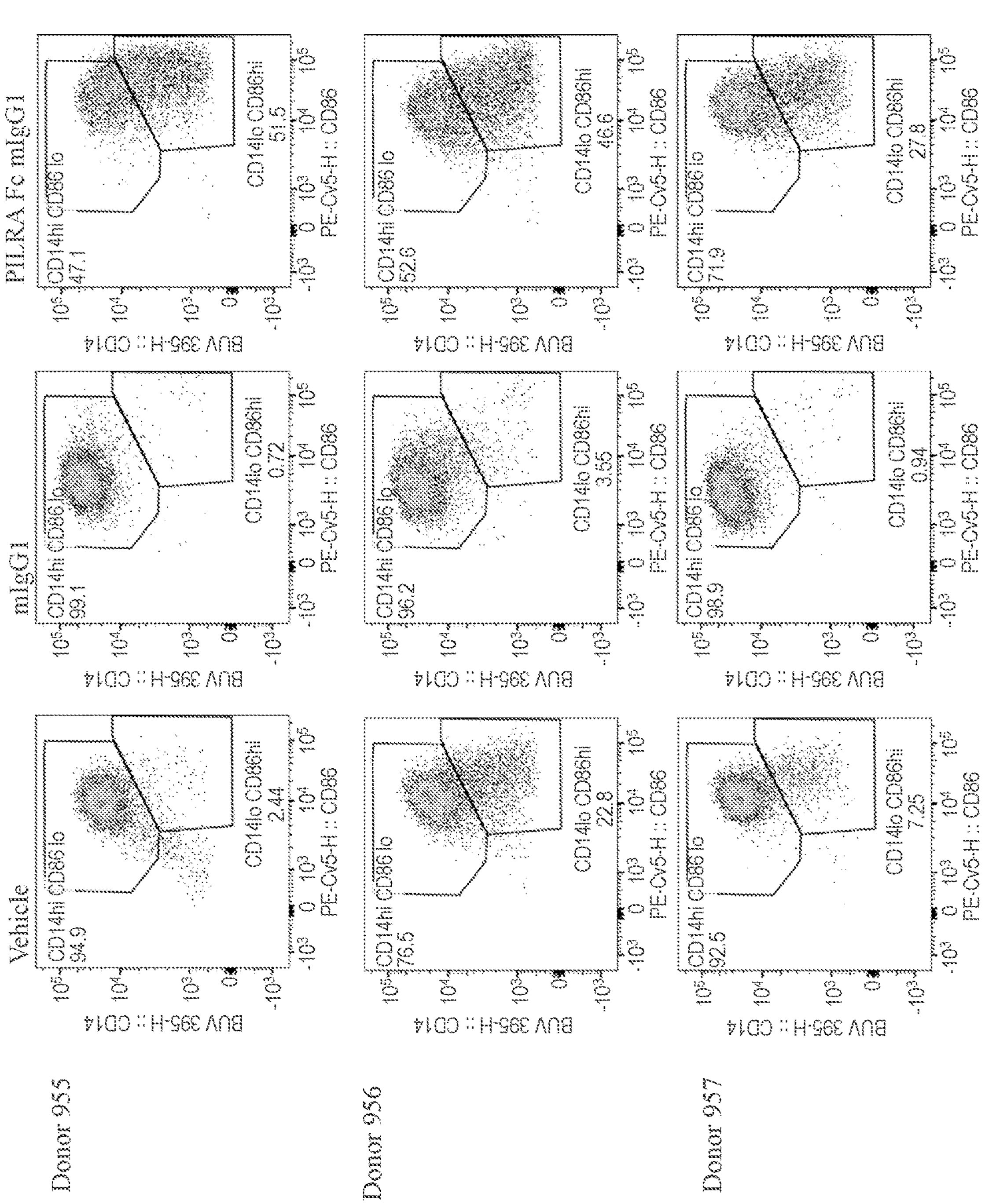
FIG. 2A shows representative FACS plots showing CD14 vs CD86 expression on myeloid derived suppressor cells (MDSCs) treated with vehicle, mIgG1, or PILRA Fc mIgG1. (See Example 2.)

FIG. 2A provides representative FACS plots showing CD14 vs CD86 expression on MDSCs treated with vehicle, mIgG1, or PILRA mFc. Treatment with PILRA mFc increased the percentages of $CD14^{lo}CD86^{hi}$ (activated) myeloid cells, indicating that blocking inhibitory signaling of PILRA enhanced the differentiation of these cells to a more mature and activated phenotype. Therefore, a blocking anti-PILRA antibody would be expected to have a comparable effect in promoting the activation and differentiation of myeloid cells.

Figure 2B:
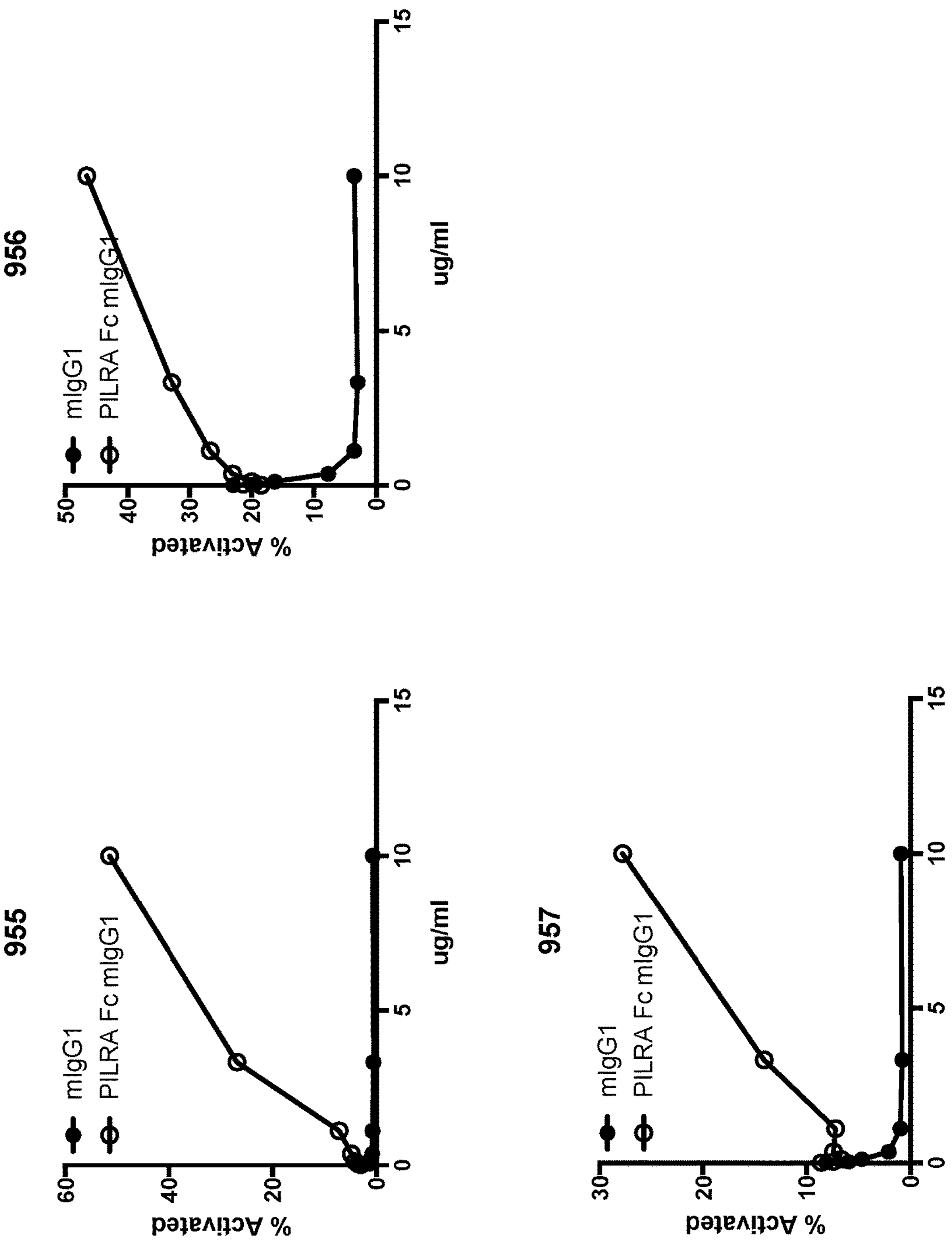
FIG. 2B shows the percentage of activated myeloid cells from three different donors after treatment with mIgG1 isotype control or PILRA Fc relative to vehicle treated cells. (See Example 2.)

FIG. 2B shows the percentage of activated myeloid cells after MDSCs from 3 donors (955, 956, and 957) were treated with mIgG1 isotype control or PILRA mFc relative to vehicle treated cells. PILRA mFc increased the activated myeloid cells, as measured by the percentage of $CD14^{lo}CD86^{hi}$ (activated) myeloid cells, in MDSC samples from all 3 donors.

Example 3: PILRA Fc Induces MDSC Production of MIP1b

Figure 3:
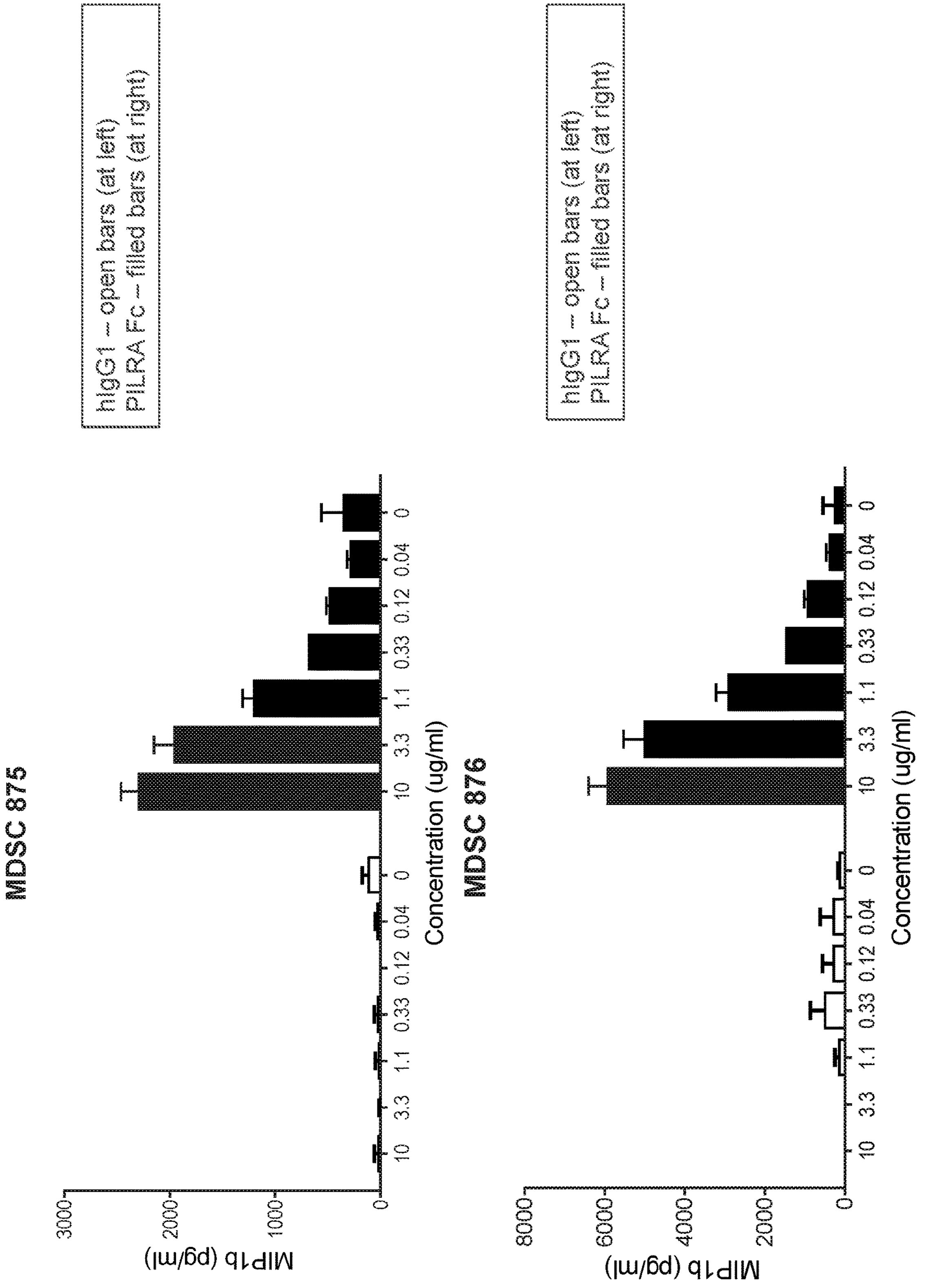
FIG. 3 shows the effect of PILRA Fc on production of MIP1b by MDSC. (See Example 3.)

To further explore the role of PILRA in myeloid cell activation, myeloid derived suppressor cells (MDSCs) were generated from 2 donors by culturing blood derived monocytes with 100 ng/ml GM-CSF and 100 ng/ml TL-6 for 5 days. Cells were then harvested and treated with vehicle or with increasing doses of hIgG1 isotype control or PILRA Fc (as in Example 1). PILRA Fc acts as a soluble antagonist, binding PILRA ligands expressed on these cells and preventing their interaction with cell surface endogenous PILRA. After 3 days of treatment, conditioned media was harvested and assayed for MIP1b (CCL4). MIP1b is a chemoattractant that promotes recruitment of myeloid cells and lymphocytes. Relative to hIgG1 isotype control, PILRA antagonism using PILRA Fc induced MIP1b production, which is consistent with increased myeloid cell activation (FIG. 3).

Example 4: Anti-Mouse PILRA Antibodies Do Not Bind Human PILRA

Antibodies against murine PILRA were generated as follows. C57BL/7 $PILRA^{-/-}$ $PILRB1^{-/-}$ $PILRB2^{-/-}$ mice were immunized with murine PILRA (mPILRA) protein, and hybridomas were prepared using standard methods. 135 conditioned media samples containing antibodies were assessed for binding to parental 293F cells or 293 cells ectopically expressing human PILRA (hPILRA), human PILRB (hPILRB), cynomolgus PILRA (cPILRA), mPILRA, or murine PILRB (mPILRB1) by FACS. Briefly, conditioned media containing antibodies were incubated with 293 cells for 30 min at 4° C., washed twice, and then detected with anti-mouse IgG Alexa 647. Cells were analyzed by flow cytometry on FACS Canto II, and for all cell lines, the MFI values relative to 293_parental cells were calculated for each conditioned media. The results are reported in Table 8. 15 antibodies were identified as mPILRA binders using a cutoff of greater than 5-fold binding. Of these binders, 10 antibodies also showed binding to murine PILRB (mPILRB)-expressing cells (>5 fold), and 1 antibody bound to cynomolgus monkey PILRA (cPILRA)-expressing cells (>5 fold). None of these 15 mPILRA binders bound hPILRA- or hPILRB-expressing cells.

TABLE 8

Binding of Anti-Murine Antibodies to PILRA and PILRB

| Clone | 293 Parental MFIr | 293 hPILRA MFIr | 293 hPILRB MFIr | 293 cPILRA MFIr | 293 mPILRA MFIr | 293 mPILRB MFIr |
|---|---|---|---|---|---|---|
| mPA-001 | 1.0 | 1.1 | 1.1 | 2.4 | 116.4 | 7.2 |
| mPA-002 | 1.0 | 1.1 | 1.2 | 2.4 | 111.4 | 8.0 |
| mPA-003 | 1.0 | 1.1 | 1.2 | 2.3 | 127.1 | 6.6 |

TABLE 8-continued

Binding of Anti-Murine Antibodies to PILRA and PILRB

| Clone | 293 Parental MFIr | 293 hPILRA MFIr | 293 hPILRB MFIr | 293 cPILRA MFIr | 293 mPILRA MFIr | 293 mPILRB MFIr |
|---|---|---|---|---|---|---|
| mPA-004 | 1.0 | 1.1 | 1.2 | 2.0 | 95.9 | 3.4 |
| mPA-005 | 1.0 | 1.1 | 1.2 | 2.1 | 102.7 | 5.4 |
| mPA-006 | 1.0 | 1.1 | 1.2 | 1.8 | 92.9 | 2.2 |
| mPA-007 | 1.0 | 1.1 | 1.2 | 237.3 | 87.5 | 3.3 |
| mPA-008 | 1.0 | 1.1 | 1.2 | 2.0 | 107.2 | 2.2 |
| mPA-009 | 1.0 | 1.1 | 1.2 | 2.1 | 153.5 | 4.2 |
| mPA-010 | 1.0 | 1.1 | 1.2 | 2.0 | 93.6 | 7.1 |
| mPA-011 | 1.0 | 1.1 | 1.2 | 2.0 | 71.2 | 8.7 |
| mPA-012 | 1.0 | 1.1 | 1.2 | 2.2 | 86.9 | 9.5 |
| mPA-013 | 1.0 | 1.1 | 1.2 | 1.9 | 70.0 | 6.2 |
| mPA-014 | 1.0 | 1.1 | 1.2 | 2.2 | 126.9 | 9.8 |
| mPA-015 | 1.0 | 1.1 | 1.2 | 1.9 | 93.3 | 6.6 |

Figure 4:
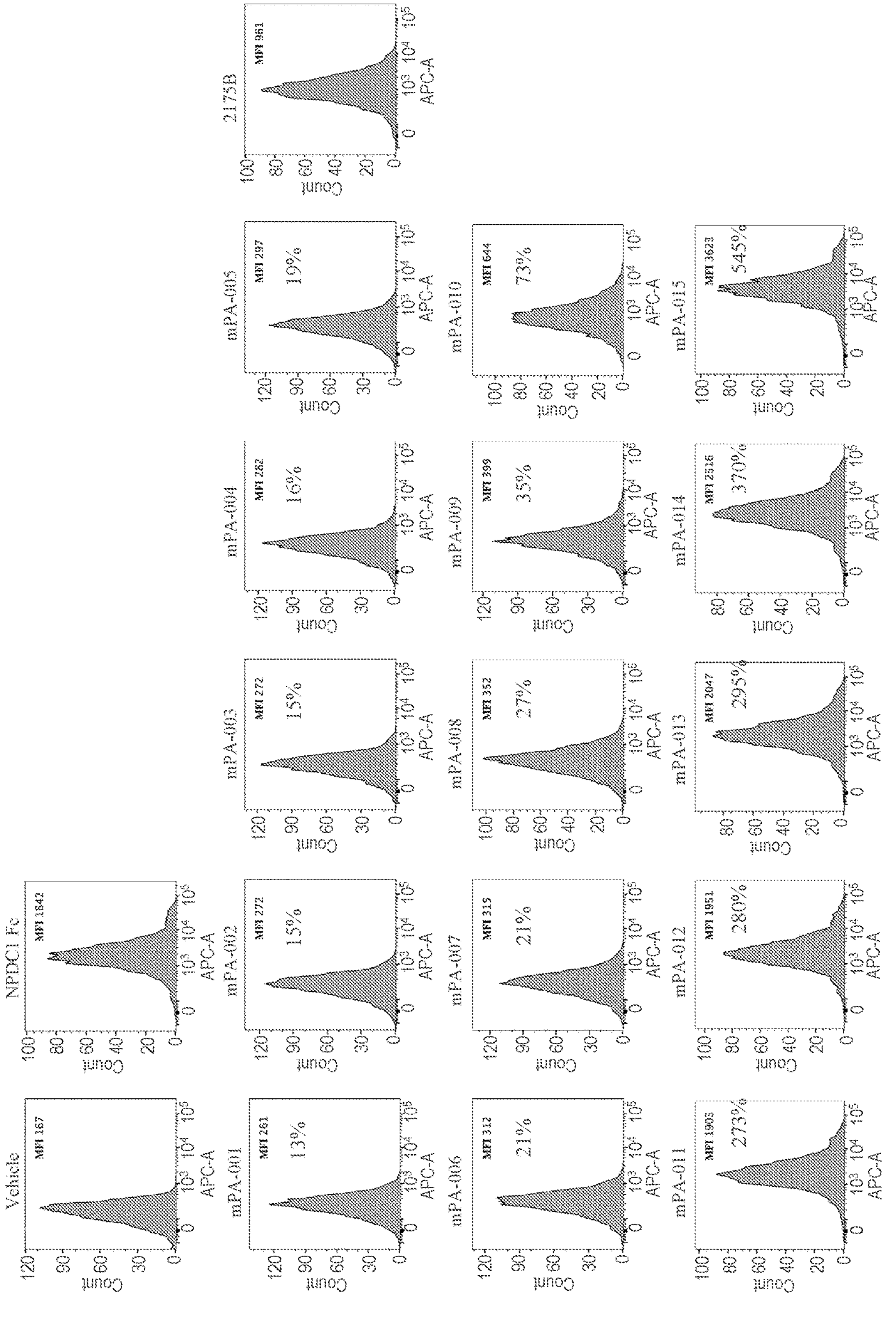
FIG. 4 shows the effect of anti-murine PILRA antibodies on binding of NPDC1 Fc to mouse PILRA. (See Example 5.)

Example 5: Anti-Mouse PILRA Antibodies can Increase or Decrease Binding of NPDC1 to PILRA-Expressing Cells 135 conditioned media samples containing antibodies as described in Example 4 above were assessed for modulating the binding of Neural Proliferation Differentiation and Control Protein 1 (NPDC1) Fe to 293 cells ectopically expressing mouse PILRA. Briefly, conditioned media samples containing antibodies were incubated with 293 cells expressing mouse PILRA for 30 minutes at 4° C., and then 5 ug/ml NPDC1 hIgG1 Fc ("NPDC Fc") was added to this mixture. After 30 minutes incubation at 4° C., cells were washed and cell-bound NPDC1 hIgG1 Fc was detected with anti-human IgG Alexa 647. Cells were analyzed by flow cytometry on FACS Canto II, and for all cell lines, the percentage of NPDC1 Fc binding in the presence of conditioned media relative to NPDC1 Fc binding alone was calculated. The results are shown in FIG. 4. 10 blocking anti-mouse PILRA antibodies that disrupted NPDC-1 were identified (mPA-001 through mPA-009). 5 anti-mouse PIRLA antibodies that increased NPDC1 Fc binding were identified (mPA-011 through mPA-015).

Example 6: Production of Anti-Human PILRA Antibodies

Antibodies against human PILRA were generated as follows. C57BL/7 PILRA$^{-/-}$ PILRB1$^{-/-}$ PILRB2$^{-/-}$ mice were immunized with human PILRA protein, and hybridomas prepared using standard methods. 300 conditioned media samples containing antibodies were assessed for binding to parental 293 cells or 293 cells ectopically expressing hPILRA, hPILRB, cPILRA, mPILRA, or mPILRB by FACS. Briefly, conditioned media containing antibodies were incubated with 293 cells for 30 minutes at 4° C., washed twice, and then detected with anti-mouse IgG Alexa 647. Cells were analyzed by flow cytometry on FACS Canto II, and for all cell lines, the MFI values relative to 293 parental cells were calculated for each conditioned media. The results are shown in Table 9. Six antibodies were identified as human PILRA binders using a cutoff of greater than 5-fold binding. Of these binders, one antibody also showed binding to 293 cells expressing human PILRB and cynomolgus PILRA. No antibody was identified that bound mouse PILRA.

TABLE 9

Binding of Anti-Human Antibodies to PILRA and PILRB

| IDs | 293 Parental | 293 human PILRA | 293 human PILRB | 293 cyno PILRA | 293 mouse PILRA | 293 mouse PILRB |
|---|---|---|---|---|---|---|
| hPA-001 | 1.0 | 131.4 | 1.3 | 0.5 | 0.5 | 0.5 |
| hPA-002 | 1.0 | 133.1 | 1.2 | 0.3 | 0.3 | 0.3 |
| hPA-003 | 1.0 | 104.7 | 1.3 | 0.5 | 0.4 | 0.5 |
| hPA-004 | 1.0 | 83.9 | 1.3 | 0.6 | 0.6 | 0.6 |
| hPA-005 | 1.0 | 103.9 | 1.3 | 0.5 | 0.4 | 0.5 |
| hPA-006 | 1.0 | 152.5 | 4.5 | 3.3 | 0.4 | 0.4 |

Example 7: Anti-Human PILRA Antibodies Inhibit Binding of PILRA to T Cells

Figure 5:
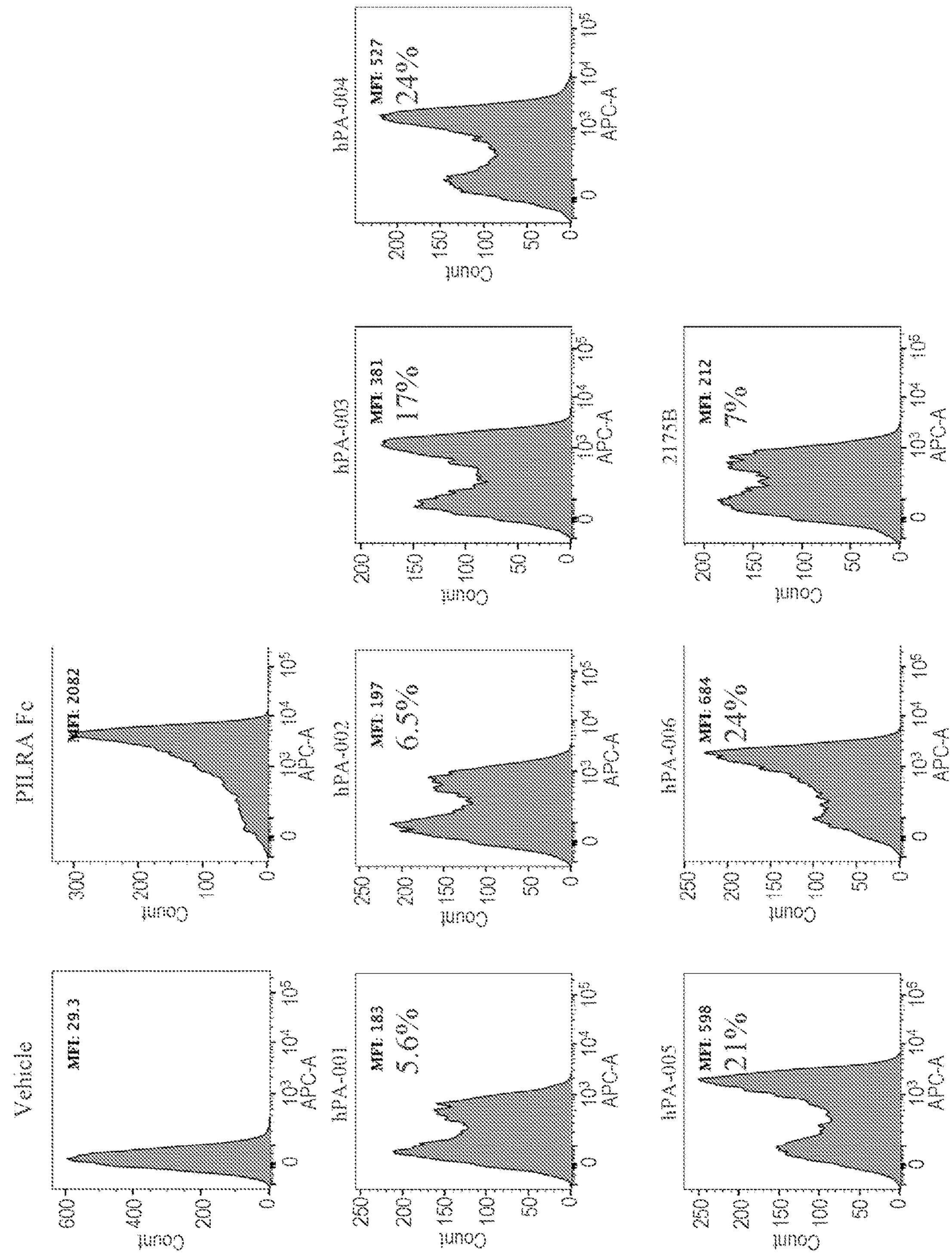
FIG. 5 shows the effect of anti-human PILRA antibodies on binding of PILRA Fc to human T cells. (See Example 7.)

The ability of the 300 conditioned media samples containing antibodies as described in Example 6 above to inhibit the binding of PILRA Fe to human CD3+ T cells was assessed. Briefly, conditioned media samples containing antibodies were incubated with 1.25 ug/ml PILRA Fc for 30 min at 4° C. and then added to human T cells. After 30 minutes incubation at 4° C., cells were washed, and bound PILRA Fc was detected with anti-human IgG Alexa 647. Cells were analyzed by flow cytometry on FACS Canto II, and for all cell lines, the amount of PILRA Fc binding (MFI) and the percentage of PILRA Fc binding in the presence of conditioned media relative to PILRA Fc binding alone was calculated. Six blocking anti-human PILRA antibodies were identified (FIG. 5).

Example 8: Anti-Human PILRA Antibodies Downregulate Cell Surface PILRA

Figure 6:
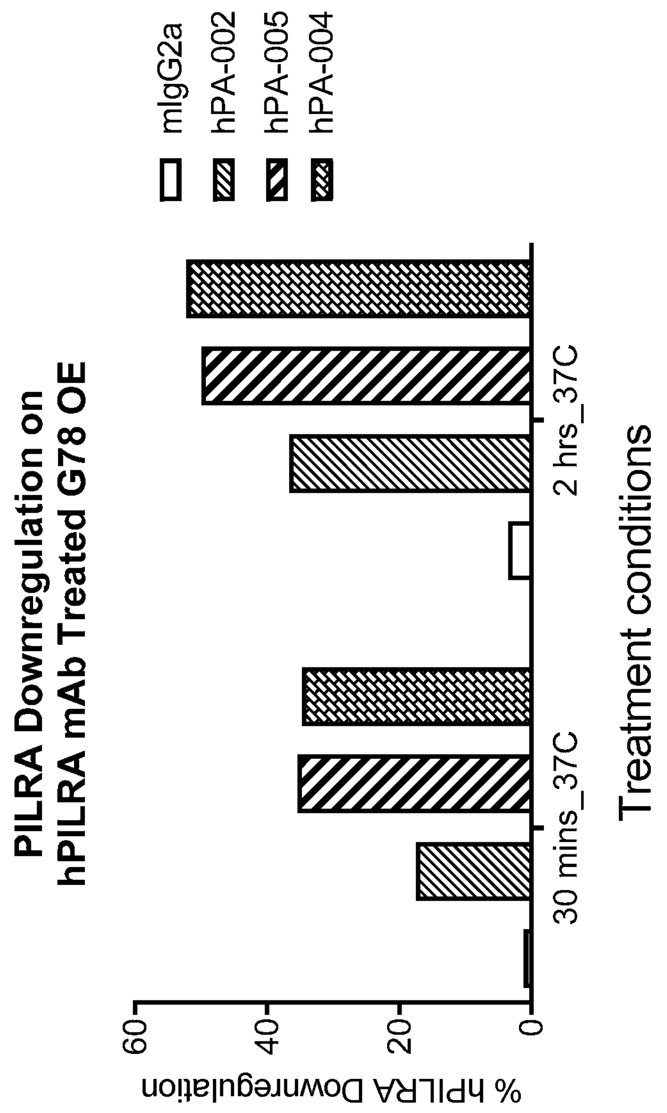
FIG. 6 shows the effect of anti-human PILRA antibodies on cell surface PILRA. (See Example 8.)

Anti-human PILRA antibodies were tested for the ability to downregulate cell surface PILRA. Purified antibodies (10 μg/ml) from the hybridoma campaign disclosed in Example 6 above were incubated with sialidase-treated 293 cells ectopically expressing the G78 variant of human PILRA for 30 minutes or 2 hours on ice or at 37° C. Surface PILRA was then detected with fluorescently-labeled sheep anti-human PILRA (1 μg/ml, R&D Systems) and analyzed using flow cytometry on a FACS Canto II. The percentage of human PILRA downregulation was calculated by normalizing for the levels of surface PILRA detected after incubation for the indicated time points on ice compared to 37° C. The results, shown in FIG. 6, demonstrate that anti-human PILRA antibodies can downregulate cell-surface human PILRA.

Example 9: Expression of PILRA in Tumors

Figure 7:
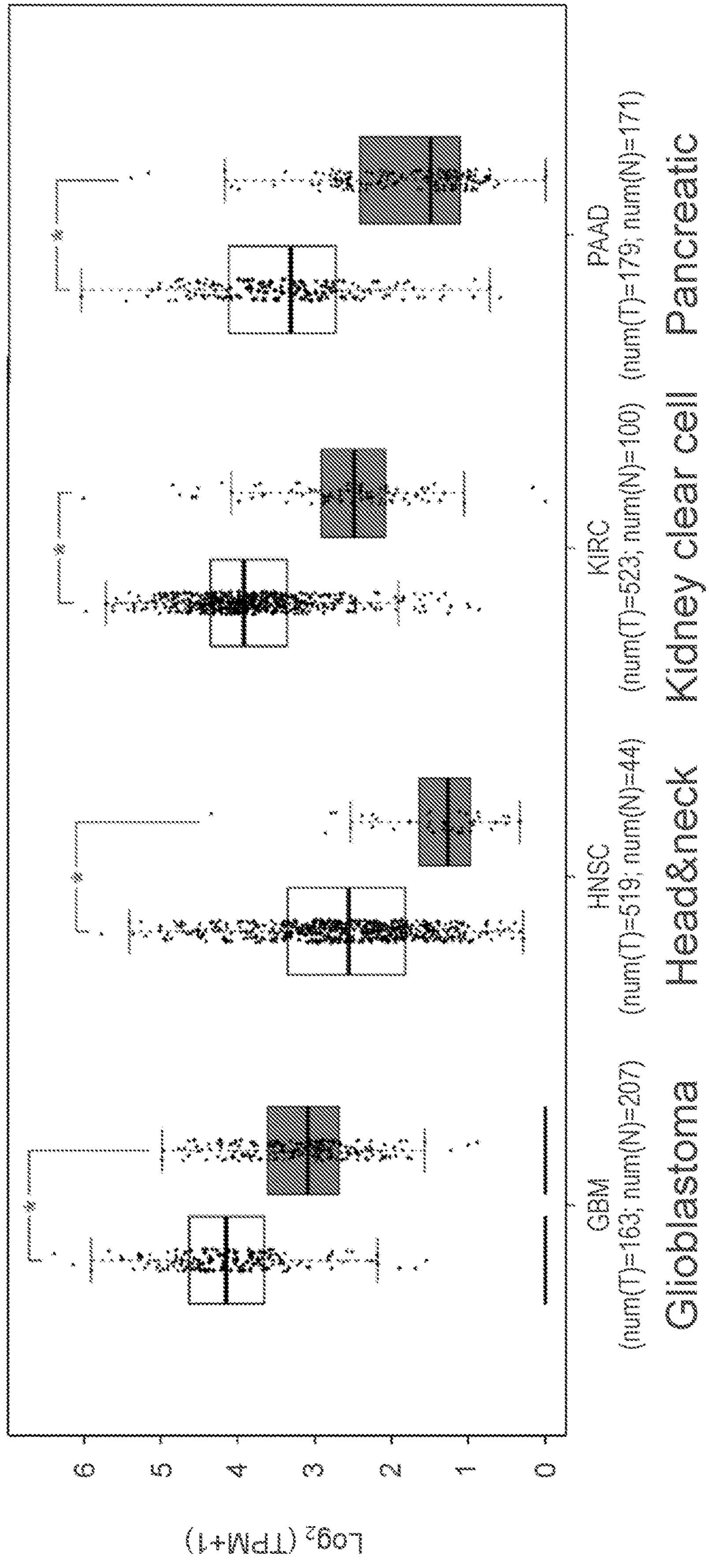
FIG. 7 shows the PILRA mRNA expression levels of tumor (dots and unfilled boxes on left side of each column) and matched healthy samples (dots and filled boxes on right side of each column). * designates $p<0.01$. (See Example 9.)

In order to compare the expression of PILRA in tumors as compared to healthy tissue, RNAseq data from cancer samples from TCGA and normal samples from GTEX were analyzed for PILRA expression. The results are shown in FIG. 7, wherein each dot represents an individual sample. These results demonstrates that glioblastoma, head and neck cancer, kidney cancer, and pancreatic cancer (left side of each column, showing dots and unfilled boxes) have increased PILRA expression compared to corresponding healthy tissues (right side of each column, showing dots and filled boxes). Without being bound by theory, increased expression is attributed at least to infiltration of PILRA-expressing myeloid cells.

Example 10: Blocking PILRA Signaling Reduces Tumor Growth in Combination with an Anti-PD-L1 Antibody The effect of blocking PILRA signaling on tumor growth was examined using PILRA-Fc in combination with an anti-PD-L1 antibody. mPILRA mIgG1 Fc can bind to PILRA ligands and prevent signaling by cell surface PILRA, therefore acting as an antagonist for the PILRA pathway. In these assays, C57BL/6 mice were inoculated with MC38 colon carcinoma cells subcutaneously. Mice were dosed with antibody isotype control (13 mg/kg), with anti-PD-L1 (3 mg/kg), or with a combination of mPILRA mIgG1 Fc (10 mg/kg) and anti-PD-L1 antibody (3 mg/kg) twice a week for 3 weeks.

Figure 8:
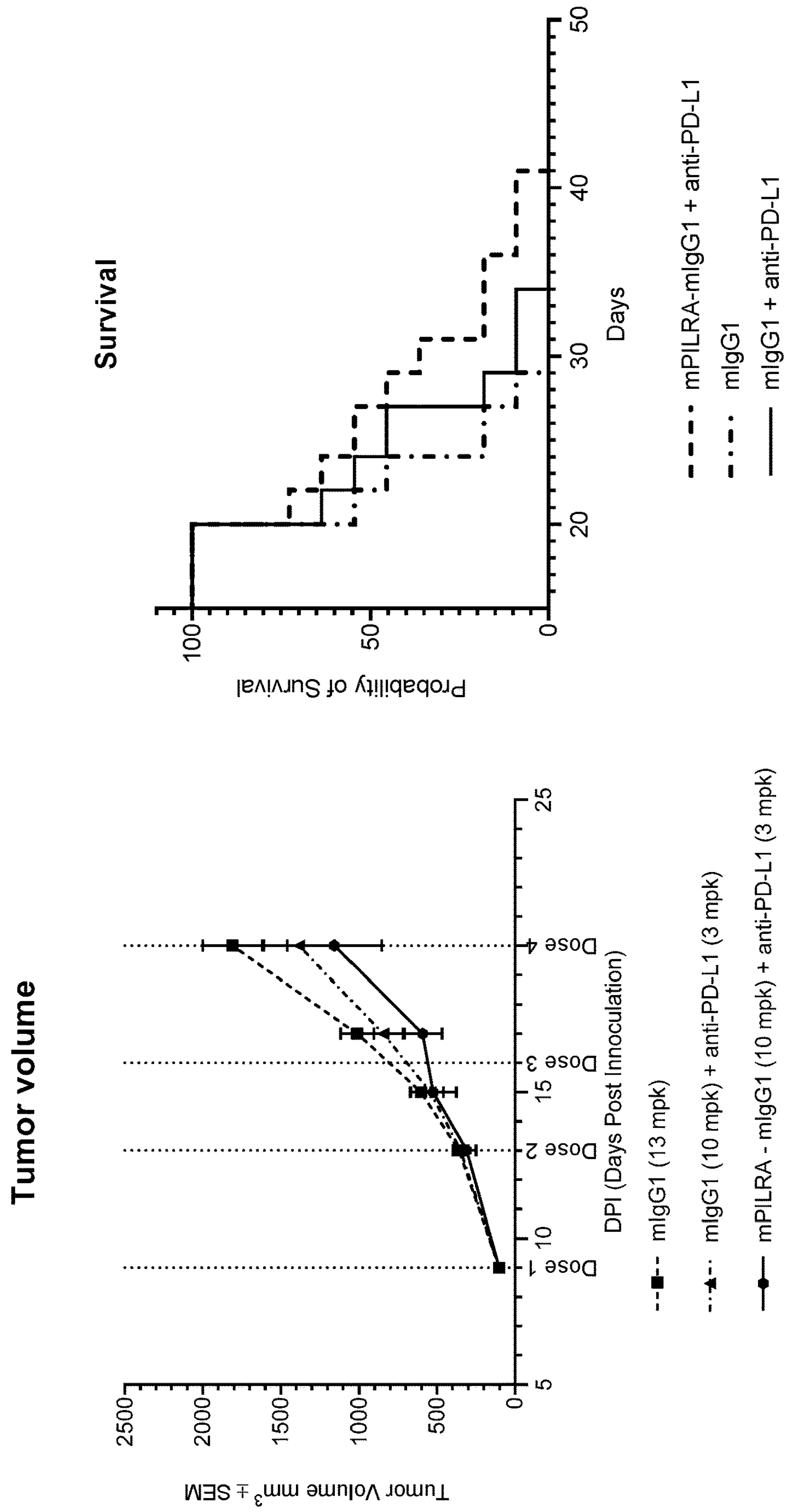
FIG. 8 shows the effect of a PILRA Fc in combination with anti-PD-L1 in the syngeneic MC38 tumor model. (See Example 10.)

FIG. 8 shows the resulting tumor volumes (left graph) and survival (right graph). A trend towards decreased tumor growth was observed on Day 17 and 20 in the group of mice that received mPILRA mIgG1 Fc in combination with the anti-PD-L1 antibody as compared to the group of mice that received only the anti-PD-L1 antibody. Furthermore, a trend towards increased surival was observed in the group of mice that received mPILRA mIgG1 Fc in combination with the anti-PD-L1 antibody as compared to the group of mice that received only the anti-PD-L1 antibody. These data demonstrate that blocking PILRA signaling can decrease tumor growth and increase survival in combination with an anti-PD-L1 antibody.

Example 11: hPA-002 is a Highly Potent Ligand Blocker

Purified anti-hPILRA antibodies were evaluated for their ability to block binding of PILRA Fc to human CD3+ T cells from 3 separate donors in order to calculate the ligand blocking potency of these antibodies. IC50 values were calculated (average+standard error) for each antibody, and they are shown in Table 10.

TABLE 10

Antibody IC50 Values for Blocking Ligand Binding

| Antibody | IC50 ± SEM (nM) |
|---|---|
| 2175B | 1.7 ± 0.47 |
| hPA-002 | 0.75 ± 0.08 |
| hPA-005 | 1.9 ± 0.2 |
| hPA-004 | 1.7 ± 0.6 |

The hPA-002 antibody blocks binding of PILRA Fc more potently than the 2175B antibody. hPA-005 and hPA-004 have a similar potency to 2175B.

Figure 9:
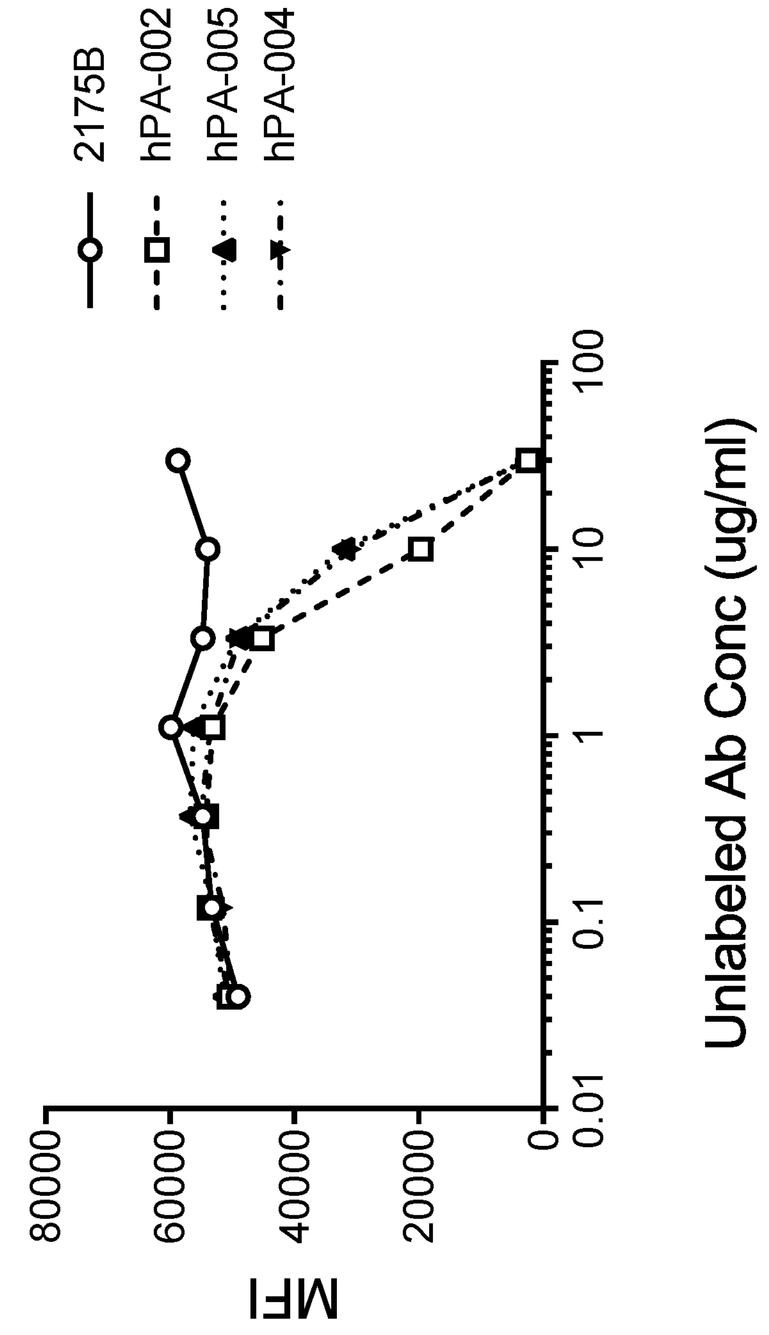
FIG. 9 shows that hPA-002, hPA-005 and hPA-004 show competitive binding to PILRA-expressing cells, whereas Ab 2175B does not. (See Example 12.)

Example 12: hPA-002, hPA-005 and hPA-004, But Not 2175B, Competitively Bind PILRA To examine whether hPA-002, hPA-005, hPA-004 and/or 2175B competitively bind to PILRA, 293FS hPILRA expressing cells were incubated with unlabeled 2175B, hPA-002, hPA-005, or hPA-004 for 30 minutes on ice. Then, Alexa 647 conjugated hPA-002 was added at a concentration of 5 μg/ml and further incubated for 30 minutes. After washing, the amount of bound A647-conjugated hPA-002 was assessed by flow cytometry. The results, shown in FIG. 9, demonstrate that unlabeled hPA-002, hPA-005, and hPA-004 blocked binding of hPA-002 A647, whereas 2175B did not block binding of hPA-002 A647. These data demonstrate that hPA-005 and hPA-004 competitively inhibit binding of hPA-002 to hPILRA, but 2175B does not competitively inhibit binding of hPA-002 to hPILRA.

Figure 10A:
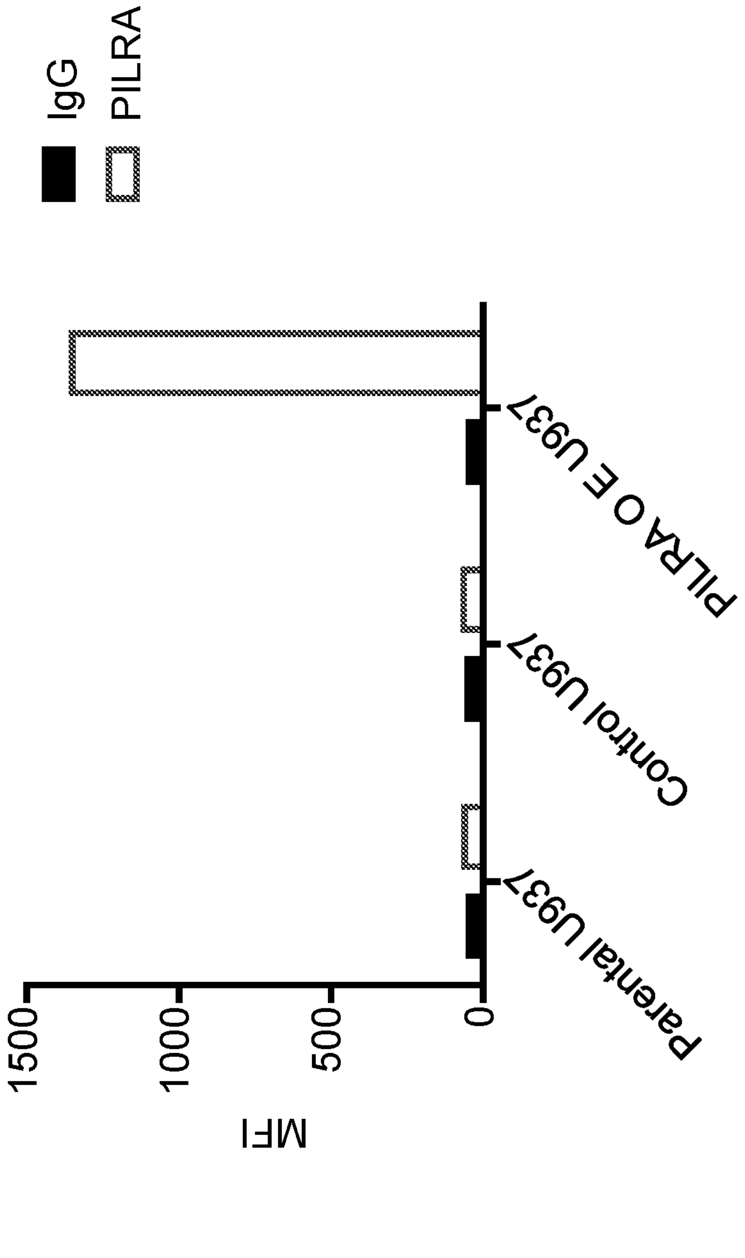
FIG. 10A shows a graph showing relative amounts of PILRA in U937 parental cells, U937 control cells, and U937 PILRA OE cells. (See Example 13.)

Example 13: hPA-002, hPA-005, and hPA-004 Enhance Activation of Myeloid Cells by Fc Receptors The effect of anti-PILRA antibodies on Fc receptor-mediated activation was assessed using the U937 myeloid cell line and derivatives as described in this Example. U937 parental cells, U937 cells expressing a control (scrambled) vector (U937 control cells), and U937 cells ectopically expressing human PILRA (PILRA OE cells) were generated. FACS analysis was performed on the cells to determine relative amounts of PILRA expression. The FACS analysis showed that PILRA OE cells express high levels of PILRA, about 17 fold higher than U937 parental cells or U937 control cells, whereas U937 parental cells and U937 control cells express minimal amounts of PILRA. (See also FIG. 10A.)

To determine the effect of hPA-002, hPA-005, and hPA-004 on activation of myeloid cells by Fc receptors, 96-well plates were coated overnight with 30 μg/mL murine IgG2a (mIgG2a) in PBS, then washed with PBS. U937 parental cells, U937 control cells, and PILRA OE cells were added to the mIgG2a-coated wells or to the untreated wells. Soluble IgG (negative control), hPA-002, hPA-005, and hPA-004 were added to the wells at 10 μg/mL. After 48 hours, the conditioned media was assessed for chemokine production (MCP-1, FIG. 10B; RANTES, FIG. 10C).

Figure 10B:
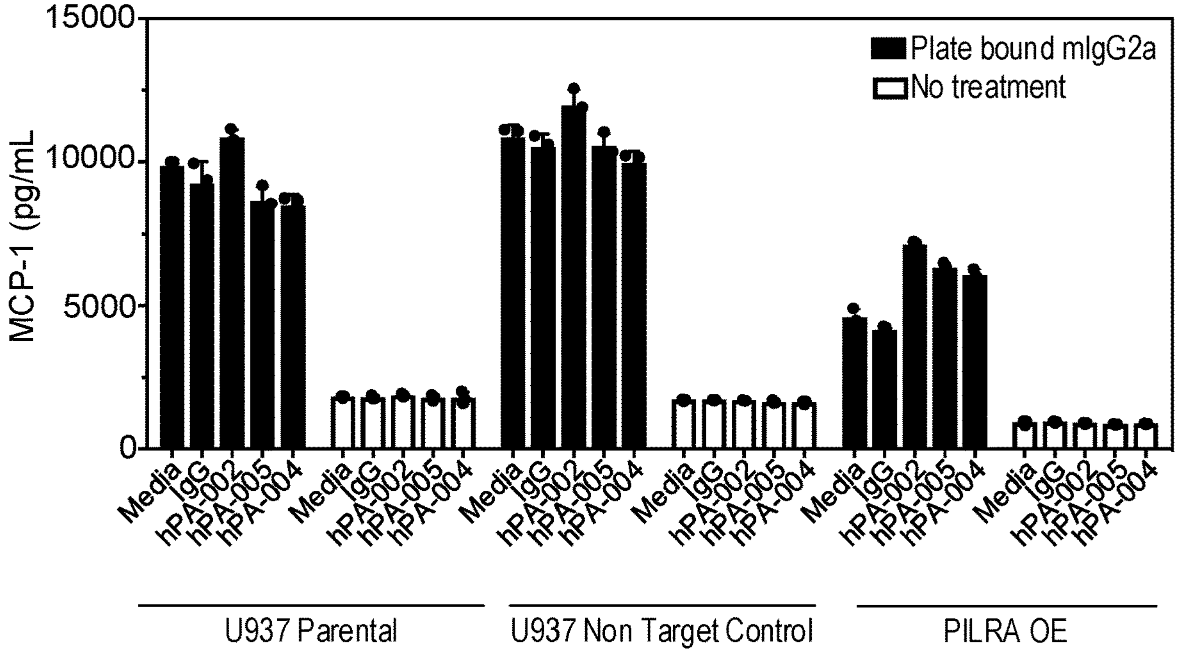
FIG. 10B shows MCP-1 production in U937 parental cells, U937 control cells, and U937 PILRA OE cells treated with IgG, hPA-002, hPA-005, and hPA-004. (See Example 13.)
Figure 10C:
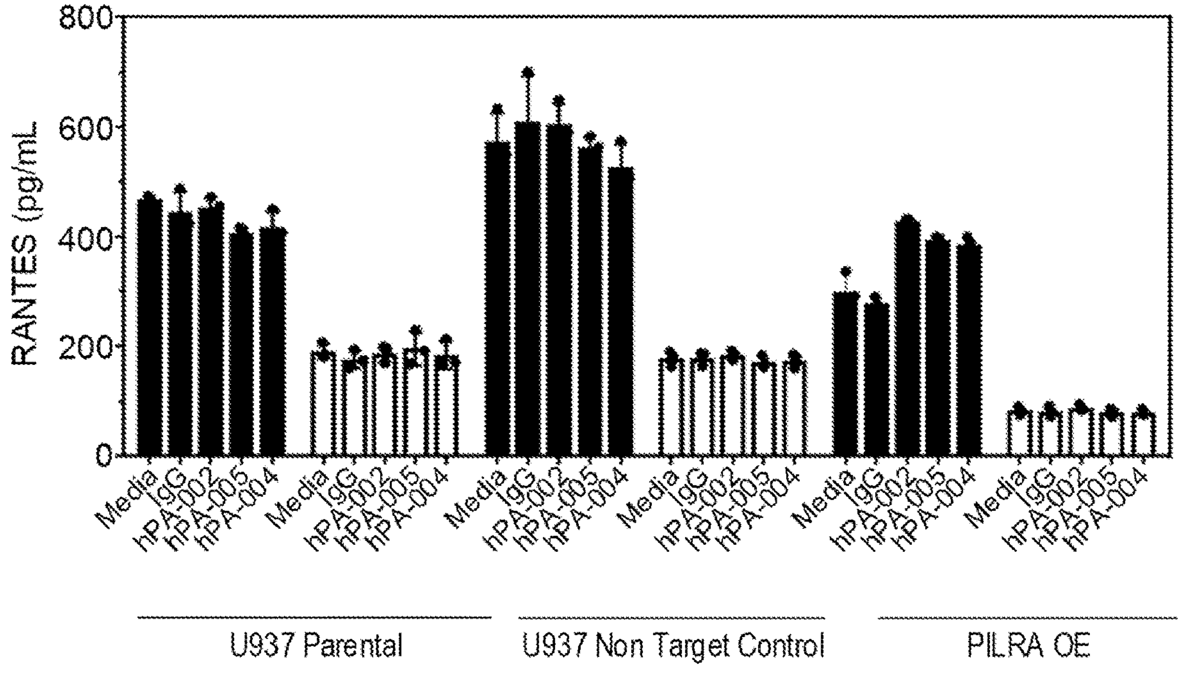
FIG. 10C shows RANTES production in U937 parental cells, U937 control cells, and U937 PILRA OE cells treated with IgG, hPA-002, hPA-005, and hPA-004. (See Example 13.)

U937 parental cells, U937 control cells, and PILRA OE cells in wells coated with mIgG2a showed increased MCP-1 and RANTES production compared to cells in untreated wells (compare black bars with white bars in FIG. 10B and FIG. 10C), indicating that plate bound mIgG2a, which behaves similarly to hIgG1, binds to the cells and activates them via Fc receptors. PILRA OE cells in wells coated with mIgG2a showed less of an increase in MCP-1 and RANTES production compared to U937 parental and U937 control cells in wells coated with mIgG2a, indicating that overexpression of PILRA inhibits Fc-mediated activation of myeloid cells (FIG. 10B and FIG. 10C). FIG. 10B and FIG. 10C also demonstrate that anti-PILRA antibodies (hPA-002, hPA-005, and hPA-004) increased MCP-1 and RANTES production in PILRA OE cells with Fc receptor activation (in wells coated with mIgG2a), compared to PILRA OE cells with Fc receptor activation in the presence of control IgG or media only. Anti-PILRA antibodies (hPA-002, hPA-005, and hPA-004) also increased MCP-1 and RANTES production in PILRA OE cells with Fc receptor activation (in wells coated with mIgG2a), compared to PILRA OE cells without Fc receptor activation (in wells not treated with mIgG2a). Anti-PILRA antibodies showed no consistent effects on U937 parental or U937 control cells, with or without mIgG2a treatment. Thus, these data demonstrate that PILRA overexpression inhibits Fc receptor-mediated activation of myeloid cells, and anti-PILRA blocking antibodies such as hPA-002, hPA-005, and hPA-004 can enhance Fc receptor-mediated activation of myeloid cells.

Example 14: Dose Response Effect of Anti-PILRA Antibodies on MCP-1 Production

Figure 11:
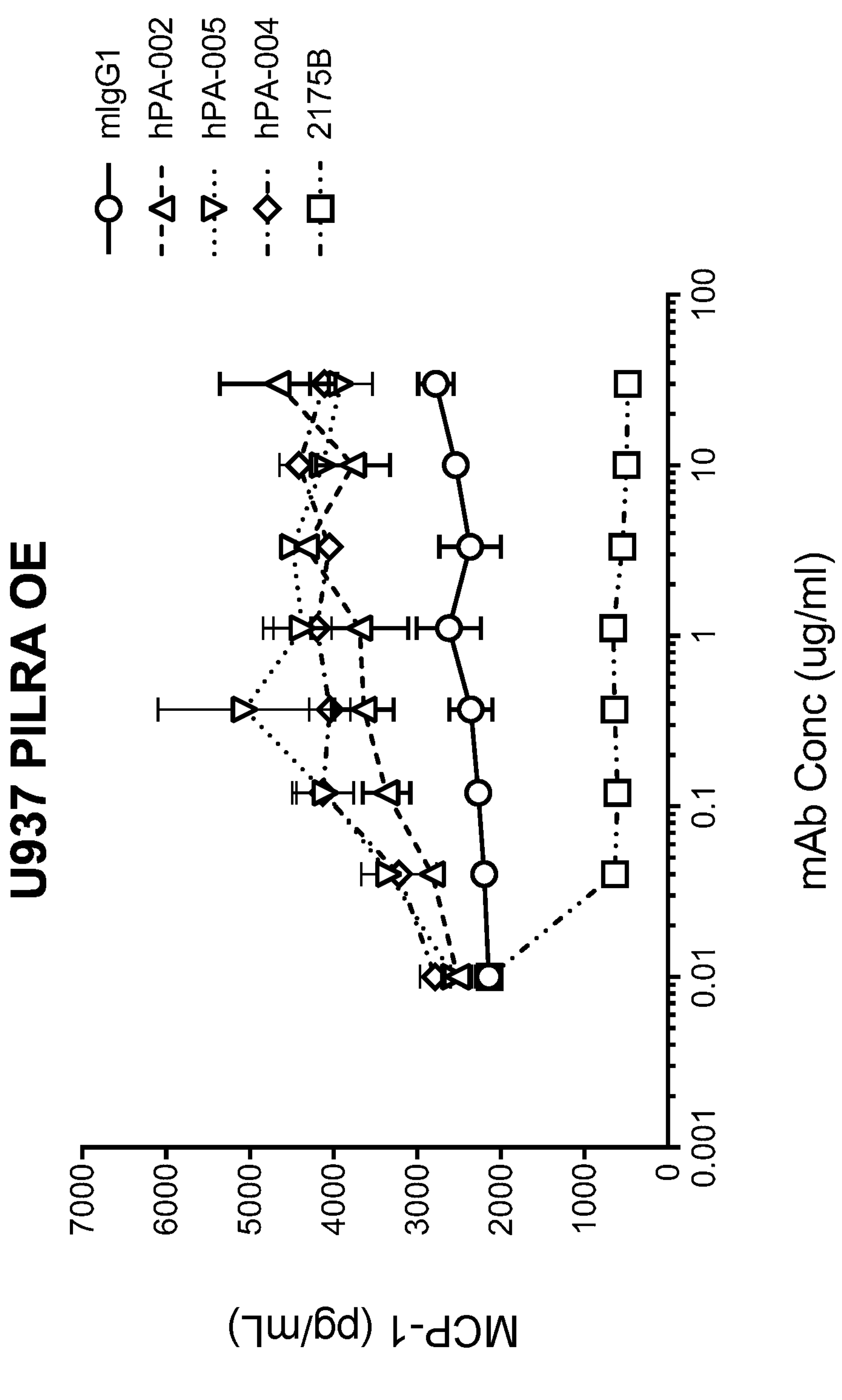
FIG. 11 shows the effect of varying concentrations of anti-PILRA antibodies on MCP-1 production in U937 PILRA OE cells. (See Example 14.)

To examine the dose response effect of different concentrations of anti-PILRA antibodies on MCP-1 production in U937 PILRA OE cells, 96-well plates were coated overnight with 30 μg/mL mIgG2a in PBS, then washed with PBS. U937 PILRA OE cells were added to the mIgG2a-coated wells, and soluble IgG (negative control), hPA-002, hPA-005, hPA-004, and 2175B antibodies were added to the wells at varying concentrations (FIG. 11). After 48 hours, the conditioned media was assessed for MCP-1 production.

FIG. 11 shows that anti-PILRA antibodies hPA-002, hPA-005, and hPA-004 dose dependently increase MCP-1 production, but anti-PILRA antibody 2175B inhibited MCP-1 production. These data suggest that hPA-002, hPA-005, and hPA-004 are PILRA antagonists, while 2175B is a PILRA agonist. The different functional activity is consistent with data in Example 12 (FIG. 9), which show that hPA-002, hPA-005, and hPA-004, but not 2175B, demonstrate competitive binding, suggesting that hPA-002, hPA-005, and hPA-004 bind to a different region of PILRA than 2175B.

Example 15: hPA-002, hPA-005, and hPA-004 Enhance Fc Receptor Activation in Primary Human Monocytes To determine the effect of anti-PILRA antibodies (hPA-002, hPA-005, and hPA-004) on Fc receptor-mediated activation in primary human monocytes, 96-well plates were coated overnight with 30 μg/mL mIgG2a in PBS, then washed with PBS. Primary human monocytes from two different donors were added to mIgG2a-coated wells or untreated wells. Soluble IgG (negative control), hPA-002, hPA-005, and hPA-004 antibodies were added to the wells at 10 μg/mL. After 48 hours, the conditioned media was assessed for MCP-1 production (FIG. 12).

Figure 12:
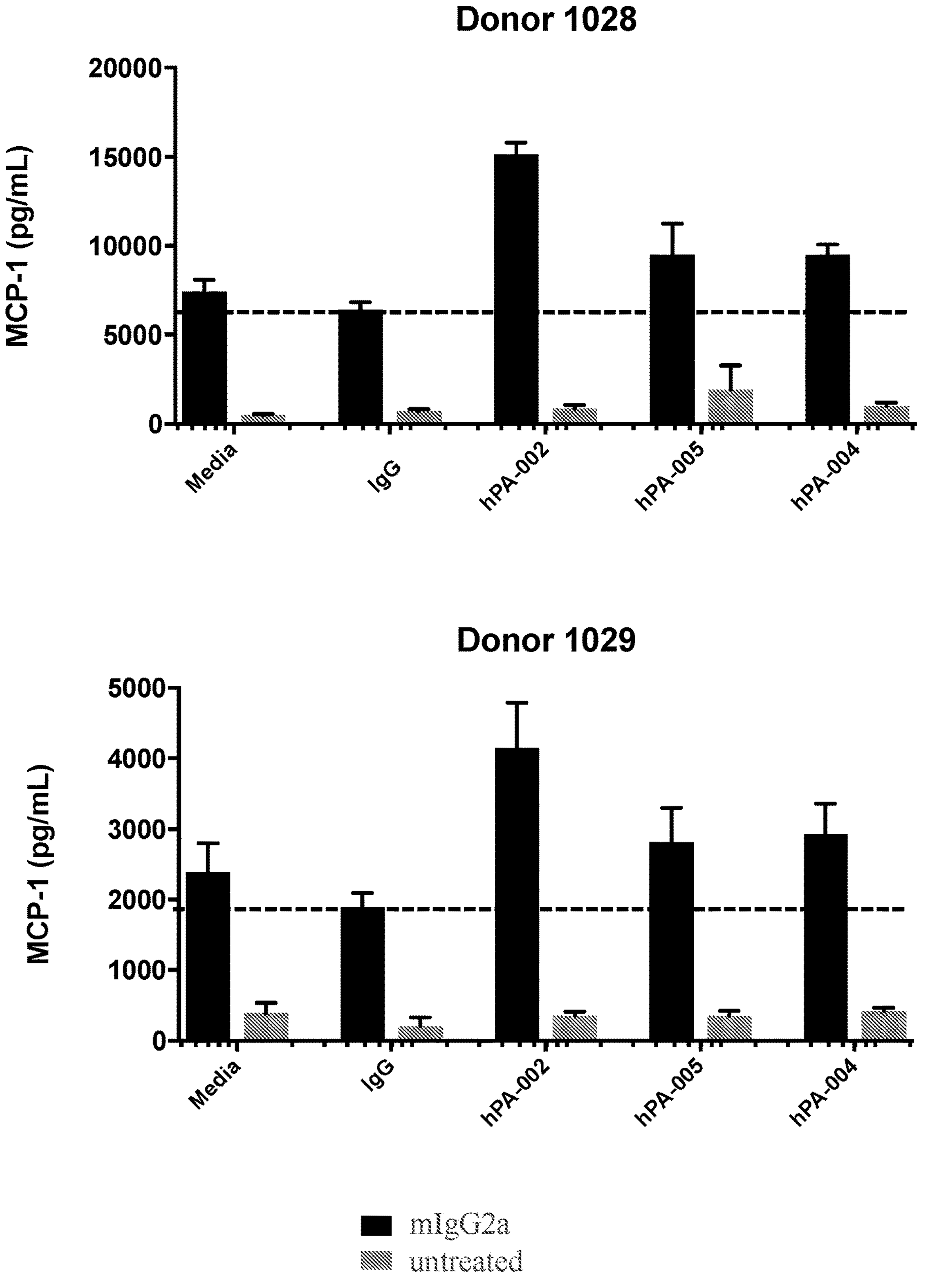
FIG. 12 shows that hPA-002, hPA-005, and hPA-004 enhance Fc receptor activation in primary human monocytes. (See Example 15.)

In FIG. 12, primary human monocytes in wells coated with mIgG2a showed increased MCP-1 production compared to primary human monocytes in untreated wells, indicating that plate bound mIgG2a activated primary human monocytes via Fc receptors. Anti-PILRA antibodies hPA-002, hPA-005, and hPA-004 increased MCP-1 production in primary human monocytes with Fc receptor-mediated activation, with hPA-002 showing the strongest effect. These data demonstrate that anti-PILRA antibodies can enhance Fc receptor-mediated activation in primary human monocytes.

The invention is not to be limited in scope by the specific aspects described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody or antigen-binding fragment thereof that specifically binds to human PILRA and comprises the heavy chain variable region (VH) complementarity determining region (CDR) 1, VH CDR2, VH CDR3 and light chain variable region (VL) CDR1, CDR2, and CDR3 sequences of:

(a) SEQ ID NOs: 4-9, respectively;

(b) SEQ ID NOs: 10-15, respectively;

(c) SEQ ID NOs: 16-21, respectively; or (d) SEQ ID NOs: 22-27, respectively.

2. The antibody or antigen-binding fragment thereof of claim 1, wherein the antibody or antigen-binding fragment comprises a heavy chain variable region and a light chain variable region comprising the amino acid sequences of:

(a) SEQ ID NOs: 28 and 29, respectively;

(b) SEQ ID NOs: 30 and 31, respectively;

(c) SEQ ID NOs: 32 and 33, respectively; or (d) SEQ ID NOs: 34 and 35, respectively.

3. The antibody or antigen-binding fragment thereof of claim 1, wherein the antibody or antigen-binding fragment thereof blocks binding of PILRA to one or more of its ligands and downregulates cell surface PILRA.

4. The antibody or antigen-binding fragment thereof of claim 3, wherein the antibody or antigen-binding fragment thereof blocks binding of PILRA-Fc to human T-cells by at least 70%, at least 75%, at least 80%, at least 85%, or at least 90% and/or wherein the antibody or antigen-binding fragment thereof downregulates cell surface PILRA by at least 10%, at least 20%, or at least 30% after 30 minutes at 37° C.

5. The antibody or antigen-binding fragment thereof of claim 1, wherein the antibody or antigen-binding fragment thereof activates myeloid cells.

6. The antibody or antigen-binding fragment thereof of claim 1, wherein the antibody or antigen-binding fragment thereof promotes myeloid cell differentiation.

7. The antibody or antigen-binding fragment thereof of claim 1, wherein the antibody or antigen-binding fragment thereof does not bind to human PILRB.

8. The antibody or antigen-binding fragment thereof of claim 1, wherein the antibody or antigen-binding fragment thereof binds to an epitope in amino acids 20-197 of SEQ ID NO: 1 and/or wherein antibody 2175B does not competitively inhibit binding of the antibody or antigen-binding fragment thereof to human PILRA.

9. The antibody or antigen-binding fragment thereof of claim 1, wherein the antibody or antigen-binding fragment comprises a heavy chain constant region and a light chain constant region, wherein the heavy chain constant region is an isotype selected from the group consisting of human IgG1, IgG2, IgG3, and IgG4 isotypes.

10. The antibody or antigen-binding fragment of claim 9, wherein the antibody or antigen-binding fragment comprises an Fc domain that is engineered to reduce effector function.

11. The antibody or antigen-binding fragment thereof of claim 1, wherein the antibody or antigen-binding fragment comprises a heavy chain constant region and a light chain constant region, wherein the heavy chain constant region is a human IgG1 heavy chain constant region, and wherein the light chain constant region is a human IgGκ light chain constant region.

12. The antibody or antigen-binding fragment thereof of claim 1, wherein the antibody or antigen-binding fragment is a monoclonal antibody.

13. The antibody or antigen-binding fragment thereof of claim 1 wherein the antibody or antigen-binding fragment thereof is a murine, chimeric, or humanized antibody or antigen-binding fragment thereof.

14. The antibody or antigen binding fragment thereof of claim 1, which is an antigen binding fragment, wherein said antigen binding fragment is a Fab, Fab', F(ab')2, single chain Fv (scFv), disulfide linked Fv, intrabody, IgGΔCH2, minibody, F(ab')3, tetrabody, triabody, DVD-Ig, Fcab, mAb2, (scFv)2, or scFv-Fc.

15. An isolated polynucleotide comprising a nucleic acid molecule encoding the heavy chain variable region or heavy chain of the antibody or antigen-binding fragment thereof of and the light chain variable region or light chain of the antibody or antigen-binding fragment thereof of claim 1.

16. An isolated vector comprising the polynucleotide of claim 15.

17. A host cell comprising (a) the polynucleotide of claim 15.

18. A method of producing an antibody or antigen-binding fragment thereof that binds to human PILRA comprising culturing the host cell of claim 17 so that the nucleic acid molecule is expressed and the antibody or antigen-binding fragment thereof is produced, wherein the method further comprises isolating the antibody or antigen-binding fragment thereof from the culture.

19. An isolated antibody or antigen-binding fragment thereof that specifically binds to human PILRA and is produced by the method of claim 18.

20. A pharmaceutical composition comprising the antibody or antigen-binding fragment thereof of claim 1 and a pharmaceutically acceptable excipient.

21. A method for downregulating cell surface PILRA comprising contacting a cell expressing PILRA on its surface with the antibody or antigen-binding fragment thereof of claim 1.

22. A method for inhibiting binding of PILRA to a PILRA ligand comprising contacting PILRA with the antibody or antigen-binding fragment thereof of claim 1 in the presence of the PILRA ligand.

23. The method of claim 22, wherein the PILRA and/or the PILRA ligand is expressed on a cell.

24. A method for increasing myeloid cell activation comprising contacting the myeloid cell with the antibody or antigen-binding fragment thereof of claim 1.

25. A method for promoting myeloid cell differentiation comprising contacting the myeloid cell with the antibody or antigen-binding fragment thereof of claim 1.

26. A method for increasing myeloid cell production of MIP1b comprising contacting the myeloid cell with the antibody or antigen-binding fragment thereof of claim 1.

27. A method of treating cancer in a patient, the method comprising administering to the patient a therapeutically effective amount of the antibody or antigen binding fragment thereof of claim 1.

28. The method of claim 27, wherein the cancer is selected from glioblastoma, head and neck cancer, kidney cancer, pancreatic cancer, and breast cancer.

29. The method of claim 27, further comprising administering an antagonist of an inhibitory immune checkpoint molecule.

30. The method of claim 29, wherein the immune checkpoint molecule is PD-1 or PD-L1.

31. The method of claim 29, wherein the antibody or antigen-binding fragment thereof that specifically binds to human PILRA and the antagonist of the inhibitory immune checkpoint molecule are administered sequentially.

32. A method of treating a disease or condition in which myeloid cells are dysfunctional or deficient in a patient, the method comprising administering to the patient a therapeutically effective amount of the antibody or antigen binding fragment thereof of claim 1.

33. A method of activating the innate immune system in a patient, the method comprising administering to the patient an effective amount of the antibody or antigen binding fragment thereof of claim 1.

34. A method for detecting PILRA in a sample comprising contacting the sample with the antibody or antigen-binding fragment thereof of claim 1.

* * * * *